United States Patent
Han et al.

(10) Patent No.: US 7,344,845 B2
(45) Date of Patent: Mar. 18, 2008

(54) OLFACTORY RECEPTOR FOR ISOVALERIC ACID AND RELATED MALODORANTS AND USE THEREOF IN ASSAYS FOR IDENTIFICATION OF BLOCKERS OF MALODOR

(75) Inventors: Yi Han, San Diego, CA (US); Sergey Zozulya, San Diego, CA (US); Fernando Echeverri, Chula Vista, CA (US); Kun Wang, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 442 days.

(21) Appl. No.: 10/300,846

(22) Filed: Nov. 21, 2002

(65) Prior Publication Data

US 2003/0207337 A1 Nov. 6, 2003

Related U.S. Application Data

(60) Provisional application No. 60/341,872, filed on Dec. 21, 2001, provisional application No. 60/348,371, filed on Jan. 16, 2002.

(51) Int. Cl.
*G01N 33/566* (2006.01)
(52) U.S. Cl. ..................... 435/7.21; 436/501
(58) Field of Classification Search ............... None
See application file for complete search history.

(56) References Cited

OTHER PUBLICATIONS

Lane et al. Genomic Analysis of Orthologous Mouse and Human Olfactory Receptor Loci, Jun. 19, 2001, P.N.A.S. vol. 98, No. 13, pp. 7390-7395.*

* cited by examiner

*Primary Examiner*—John Ulm
(74) *Attorney, Agent, or Firm*—Hunton & Williams LLP

(57) ABSTRACT

A subgenus of olfactory receptors (ORs) that are activated by isovaleric acid (IVA) are identified as well as assays that utilize one or more of these ORs. These assays are useful for identifying potential anti-odorants which may be used in deodorants, air and carpet fresheners, fabric deodorizers, and other compositions for camouflaging odor attributable to IVA and related carboxylic acids.

26 Claims, 6 Drawing Sheets

```
                      ....|....280 ....|....290 ....|....300 ....|....310 ....|....320
mORIVAA       268    SQGSTIASVM YTMWTIPMINP FIYSLRNKDV KGALVRIL-K VYSCP----- -----
OR19.04.05    268    SQSSSTASVM YIAMWTPMINP ETYSLRNKDV KGALERLLSR ADSCP----- -----
mORIVAB       268    DDNDKVSSIF VTLIVIPMINP LIYSLRNKDV KFALHRTWRN ICKIFP---- -----
OR11.39.06    267    FDIDKVASLF VTLIVIPMLNP LIYSLRNKDV KYALRRTWNN LCNIFV---- -----
mORIVAC       268    GYKDIPVAIF YTLIVIPIINP FIYSLRNKEV INVMKRAMK- -KRL------ -----
OR03.01.01    268    GDKDIPAAIL FIHWPILINP IYSLRNREV ISVDRKILM- -KEIISRRWK Q----
mORIVAD       268    NEKDKVISVE YSIVIVSMMNP FIYSLRNKDV KGALKKVLKR EIR------- -----
OR11.22.02    268    KELDKMISVF VTIAVIPMLNP ETYSLRNKDI KGALRRKLVGR KCFSHRQ--- -----
mORIVAE       269    SHATATASLM YTLIVIPMLAP IIYSLRNKDI KTAIIKILLGS VTRSRSMDSP S----
OR19.04.11    268    SHTGAAASVM YTLIVIPMLNP EIYSLRNKGHI KGAMKTFFRG KQ-------- -----
mORIVAF       268    KDRGKMVSLF YGLIPQPMINP ETYSLRNKEV KGAFKRLVTR IILSRK---- -----
OR06.02.04    268    KDRGKMVSLF CGIIAPMLNE LIYSLRNKEV KEAFRKLVAK SLL------- -----
mORIVAG       268    MDQRKVSSVF YTLIWPMINP LIYSLRNKDV KVALNKFL-- -ERIFSCEQN -----
OR11.38.05    268    MDQGKVSSVF YTLIVIPMANP LIYSLRNKDI HVALKKTLG- -KRTFL---- -----
mORIVAI       259    NDKDVIVAVL YTMVIIPMNP ETYSLRNRDI NGAIRKTLSR R-LCSH---- -----
OR09.05.02    268    SDKDVIASVM YIVIIIPIINP FIYSLRNRDI KGAIERLFNR ATVLSQ---- -----
mORIVAJ       269    TLKDTVMSMM YTMVIIPMSNP ETYSLRNRDM KEALKRVLQK KTIF------ -----
OR17.03.01    268    TLKDTVMAMM YTMVIIPMLAP LIYSLRNRDM KGAISRVIHQ KKTFFSL--- -----
mORIVAK       265    --FEKNTLIF ASVIIPLFNP MVYTERNKEM KNALRKMCRK MLVDSD---N F----
OR11.49.11    265    --LDKMAAIF YILLNPIINP LIIYTERNKEV KQAMRRIWNR LMVVSDEKEN IKL--
mORIVAL       264    ---VDKYTAVF YTMVWSPMINP LIYTLRNSEM RNSIKKLWCK TLTT------ -----
OR11.49.10    263    ---TDKFMIVF YTITHMLSP LIYTLRNSEM RNVIEKLLGK KLTIFIIGGV SVLM
```

FIG. 1D

| | | |
|---|---|---|
| mOR IVA A | 1 | V M A G N M I V F H   L L A T L C F |
| OR 19.04.05 | 1 | V M A G T A I F V H   L L A T L G F |
| mOR IVA B | 1 | L L I G L M Y V L I   K V F A D L V |
| OR 11.39.06 | 1 | L L I G L I Y I L V   K I F A D L S |
| mOR IVA C | 1 | F C E T C G A H I H   F I F S V Q F |
| OR 03.01.01 | 1 | F C E T C G A H I H   L L F S V Q F |
| mOR IVA D | 1 | M L G C S G S V V D   F I M G I L G |
| OR 11.22.02 | 1 | I L G C C R S V V D   F I M G I L A |
| mOR IVA E | 1 | M L S G I A I N L H   L I T A L A G |
| OR 19.04.11 | 1 | M L V G N A M N L Q   M M A V L G G |
| mOR IVA F | 1 | L L G S C A S N L Q   W L I S F L I |
| OR 06.02.04 | 1 | L L G S C A S N L Q   W L I S F L I |
| mOR IVA G | 1 | F L T I C G M G T Q   F A F S N I I |
| OR 11.38.05 | 1 | L L A I C V I C A H   C I F S N I V |
| mOR IVA I | 1 | I L G C N V F N V H   L I L A V I V |
| OR 09.05.02 | 1 | M I T D N V L N S H   L I V G V I L |
| mOR IVA J | 1 | M L G D S L L H L H   L I I G V V L |
| OR 17.03.01 | 1 | M L G D S L L H L H   L I M G I L I |
| mOR IVA K | 1 | L H A G V V G H T Q   F V N S F C I |
| OR 11.49.11 | 1 | L H A G V V G H I Q   F V N S I C I |
| mOR IVA L | 1 | L H G G V I G H I Q   T V N G I C G |
| OR 11.49.10 | 1 | L H G G V V G H F Q   V V N S I C V |

FIG. 2

OLFACTORY RECEPTOR FOR ISOVALERIC ACID AND RELATED MALODORANTS AND USE THEREOF IN ASSAYS FOR IDENTIFICATION OF BLOCKERS OF MALODOR

CROSS-REFERENCE TO RELATED APPLICATIONS

This application relates to PCT WO 01/68805 A2 and U.S. Ser. No. 09/809,291, both by Zozulya et al., having a filing date of Mar. 13, 2001, and both entitled "Human Olfactory Receptors and Genes Encoding Same." These applications disclose the amino acid and nucleic acid sequences for a genus of human olfactory receptors which includes some of the isovaleric acid olfactory receptors which are the subject of this application. This application claims priority to U.S. Provisional Application Ser. No. 60/341,872 filed Dec. 21, 2001 and U.S. Provisional Application Ser. No. 60/348,371 filed Jan. 16, 2002 both of which are incorporated by reference in their entirety herein.

FIELD OF INVENTION

The present invention relates to the elucidation of the isovaleric acid odorant specificity of a number of previously reported odorant receptors, the specificity of which were previously not known, and the use of this information in the design of assays for identifying compounds that mimic, block, modulate and/or enhance the activity of isovaleric acid odorant receptors. More specifically the invention relates to the discovery that a group of murine olfactory receptors (identified as mOR IVA A through mOR IVA L infra) are activated by isovaleric acid and that these murine olfactory receptors have counterparts in the human olfactory receptor repertoire (identified as OR19-04.05 (AOLFR262), OR19.04.11 (AOLF284), OR09.05.02 (AOLFR297), OR17.03.01 (AOLFR252), OR11.22.02 (AOLFR108), OR06.02.04 (AOLFR269), OR11.49.11 (AOLFR058), OR11.49.10 (AOLFR022), OR11.39.06 (AOLFR074), OR11.38.05 (AOLFR346), and OR03.01.01 (AOLFR340) infra. These receptors and cell lines expressing these receptors or chimeras, variants, and fragments thereof have application in assays, especially high throughput assays, for identifying compounds that activate, block, mimic and/or modulate the activity of isovaleric acid receptors.

BACKGROUND OF INVENTION

Description of the Related Art

The olfactory system provides sensory information about the chemical composition of the external world. Olfactory sensation is thought to involve distinct signaling pathways. These pathways are believed to be mediated by olfactory receptors (ORs). Cells which express olfactory receptors, when exposed to certain chemical stimuli, elicit olfactory sensation by depolarizing to generate an action potential, which is believed to trigger the sensation.

As such, olfactory receptors specifically recognize molecules that elicit specific olfactory sensation. These molecules are also referred to herein as "odorants." Olfactory receptors belong to the 7-transmembrane receptor superfamily (Buck et al., Cell 65:175–87 (1991)), which are also known as G protein-coupled receptors (GPCRs). G protein-coupled receptors mediate transmembrane signaling which controls many physiological functions, such as endocrine function, exocrine function, heart rate, lipolysis, carbohydrate metabolism, neurotransmission, vision and taste perception. The biochemical analysis and molecular cloning of a number of such receptors has revealed many basic principles regarding the function of these receptors.

Genes encoding the olfactory receptors are active primarily in olfactory neurons (Axel, *Sci. Amer.*, 273:154–59 (1995)). Individual olfactory receptor types are expressed in subsets of cells distributed in distinct zones of the olfactory epithelium (Breer, *Semin. Cell Biol.*, 5:25–32 (1994)). The human genome contains approximately one thousand genes and pseudogenes that encode a diverse repertoire of olfactory receptors (Mombaerts, Annu. Rev. Genomics Hum. Genet., 2:493–510 (2001), Glusman et al., Genome Res., 11(5):685–702 (2001); Zozulya et al., Genome Biol., 2(6): 0018 (2001)). It has been demonstrated that members of the OR gene family are distributed on all but a few human chromosomes. Through fluorescence in situ hybridization analysis, Rouquier showed that OR sequences reside at more than 25 locations in the human genome. Rouquier also determined that the human genome has accumulated a striking number of dysfunctional OR copies: 72% of the analyzed sequences were found to be pseudogenes. An understanding of an animal's ability to detect and discriminate among the thousands of distinct odorants or tastants, and more particularly to distinguish, for example beneficial tastants or odorants from toxic tastants or odorants, is complicated by the fact that chemosensory receptors belong to a multigene family with over a thousand members. For instance, there are up to 1,000 odorant receptors in mammals.

Moreover, each chemosensory receptor neuron may express only one or a few of these receptors. With respect to odorant receptors, any given olfactory neuron can respond to a small set of odorant ligands. In addition, odorant discrimination for a given neuron may depend on the ligand specificity of the one or few receptors it expresses. To analyze odorant-receptor interactions and their effects on olfactory cells, specific ligands and the olfactory receptors to which they bind are identified. This analysis requires isolation and expression of olfactory polypeptides, followed by binding assays.

Some studies suggest that OR genes can be expressed in tissues other that the olfactory epithelium, indicating potential alternative biological roles for this class of chemosensory receptors. Expression of various ORs has been reported in human and murine erythroid cells (Feingold 1999), developing rat heart (Drutel, *Receptor Channels*, 3(1):33–40 (1995)), avian notochord (Nef, *PNAS*, 94(9):4766–71 (1997)) and lingual epithelium (Abe, *FES Letl.*, 316(3): 253–56 (1993)). One well experimentally documented case also established the existence of a large subset of mammalian ORs transcribed in testes and expressed on the surface of mature spermatozoa, thereby suggesting a possible role of ORs in sperm chemotaxis (Parmenthier, *Nature*, 355:453–55 (1992); Walensky, *Mol. Med.*, 1(2):130–41 (1998); Branscomb, *Genetics*, 156(2):785–97 (2000)). It was also hypothesized that olfactory receptors might provide molecular codes for highly specific cell-cell recognition functions in development and embryogenesis (Dreyer, *PNAS*, 95(11): 9072–77 (1998)).

The elucidation of a family of receptors encoded in the human genome which comprise over two hundred and fifty G-protein coupled receptors that are involved in the perception of odorants and human smell is disclosed in Senomyx PCT WO 01/68805 A2, having an international filing date of Mar. 13, 2001, entitled "Human Olfactory Receptors and Genes Encoding Same" by Zozulya, S., and U.S. Ser. No. 09/809,291 also by Zozulya, Sergey also filed on Mar. 13, 2001. Additionally, Zozulya et al. recently disclosed in *Genome Biology* a repertoire of human olfactory receptors (Zozulya et al., "The Human Olfactory Receptor Repertoire", *Genome Biology* 2(6):research 0018.1–0018.12 (2001)). Both of these patent applications and this publication by Zozulya are incorporated by reference in their entirety herein.

The discovery encompassed by these patent applications and publication is enormous as it provides a large genus of olfactory receptors that may be utilized in screens to identify odorant molecules that activate one or more of these receptors. These molecules have application, e.g. in cosmetics and compositions for consumptions. However, these patent applications fail to provide the odorant specificity of many of these receptors. Particularly, these patent applications fail to identify whether the genus of odorant receptors disclosed therein includes receptors having specificity for isovaleric acid or related carboxylic acid odorants.

With respect thereto, it is generally known that the malodor of human and animal bodily secretions, particularly sweat, is partially attributable to the production of several unpleasant smelling organic acids, including particularly isovaleric acid and 3-methyl-2-hexenoic acid (constituents of human sweat), propionic acid (constituent of foul malodor) and hexenoic acid (a constituent of pet malodor).

In order to alleviate such odors, numerous types of anti-odorant compositions have been developed, and are available in various forms including deodorants, air fresheners, fabric fresheners, carpet fresheners, among others. These compositions contain a variety of active ingredients intended to alleviate malodor. Some of these constituents function by camouflaging the malodor by substituting a more pleasant smell, e.g. a perfume. Some others function by blocking the malodor by a phenomenon known as cross adaptation with the malodorance constituent.

The existing technology for developing anti-odorants is based on psychophysical testing of chemical compounds in order to identify either specific or general odor blockers or maskants. The screening strategies based on psychophysical testing of human subjects, however, have intrinsically very low throughput and can be subjective and error prone. Additionally, the identification of some anti-odorants has been accomplished to a limited effect by applying the conventional principles and strategies of medicinal chemistry by relying on the structure-activity (SAR) studies of malodorants and potential malodor-blocking compounds in order to identify best candidates for psychophysical testing. However, this approach is generally tedious and is generally only applicable for a malodorant of interest, especially for refining existing leads from primary screens of chemical libraries.

Therefore, it would be beneficial if more broadly applicable assays could be developed that enable the rapid identification of anti-odorants that effectively inhibit or block the odor of isovaleric acid and structurally related malodorants. Ideally, it would be beneficial if compounds could be identified that totally and selectively block the perception of the odor of isovaleric acid and/or related malodorants by mammalian subjects, preferably human subjects. This goal would ideally be achieved by developing a greater understanding of the biology of isovaleric acid odor perception, particularly by elucidating the particular receptors that are involved in the odor perception of isovaleric acid and related compounds.

BRIEF DESCRIPTION OF THE FIGURES

Figure 1A:
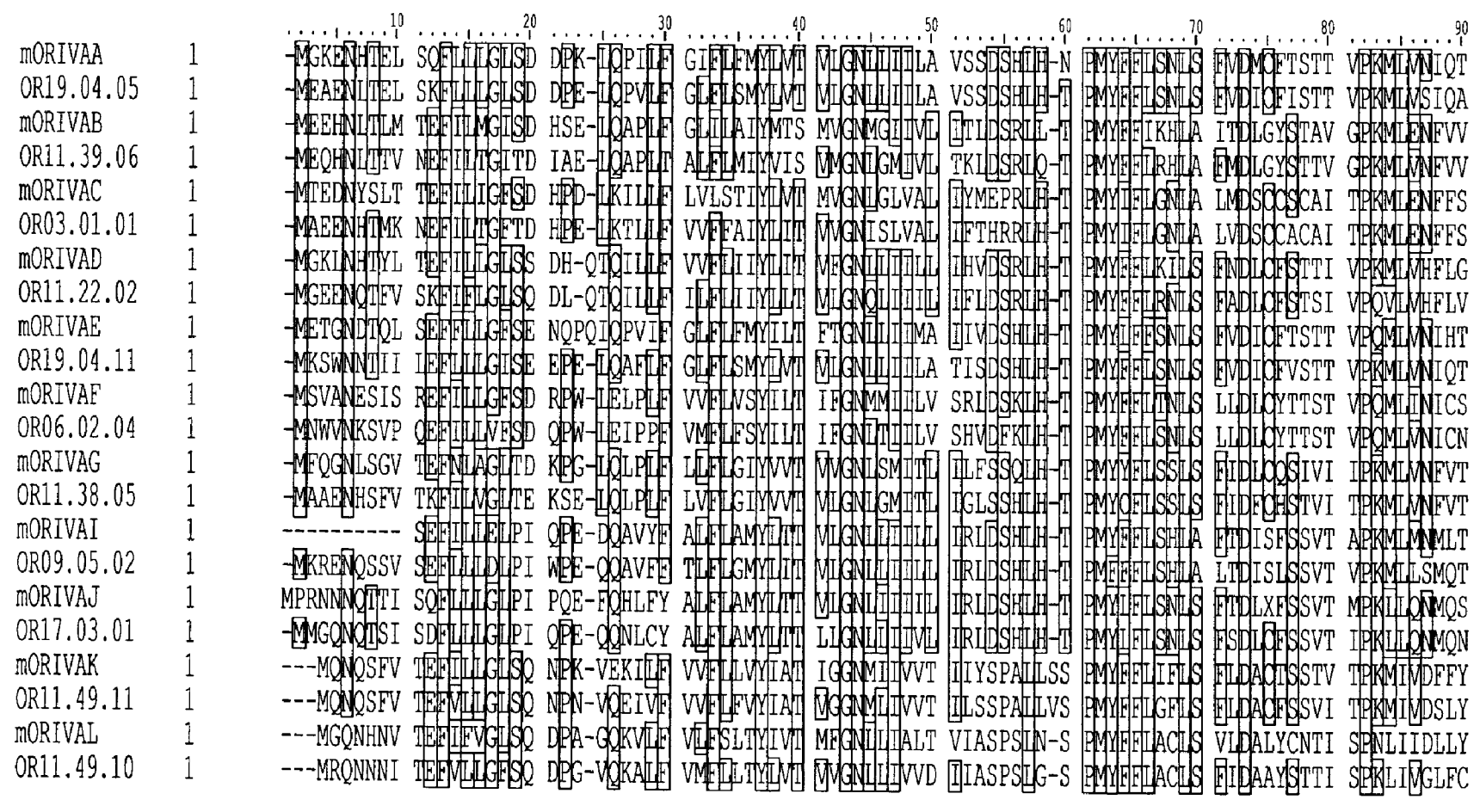
Figure 1B:
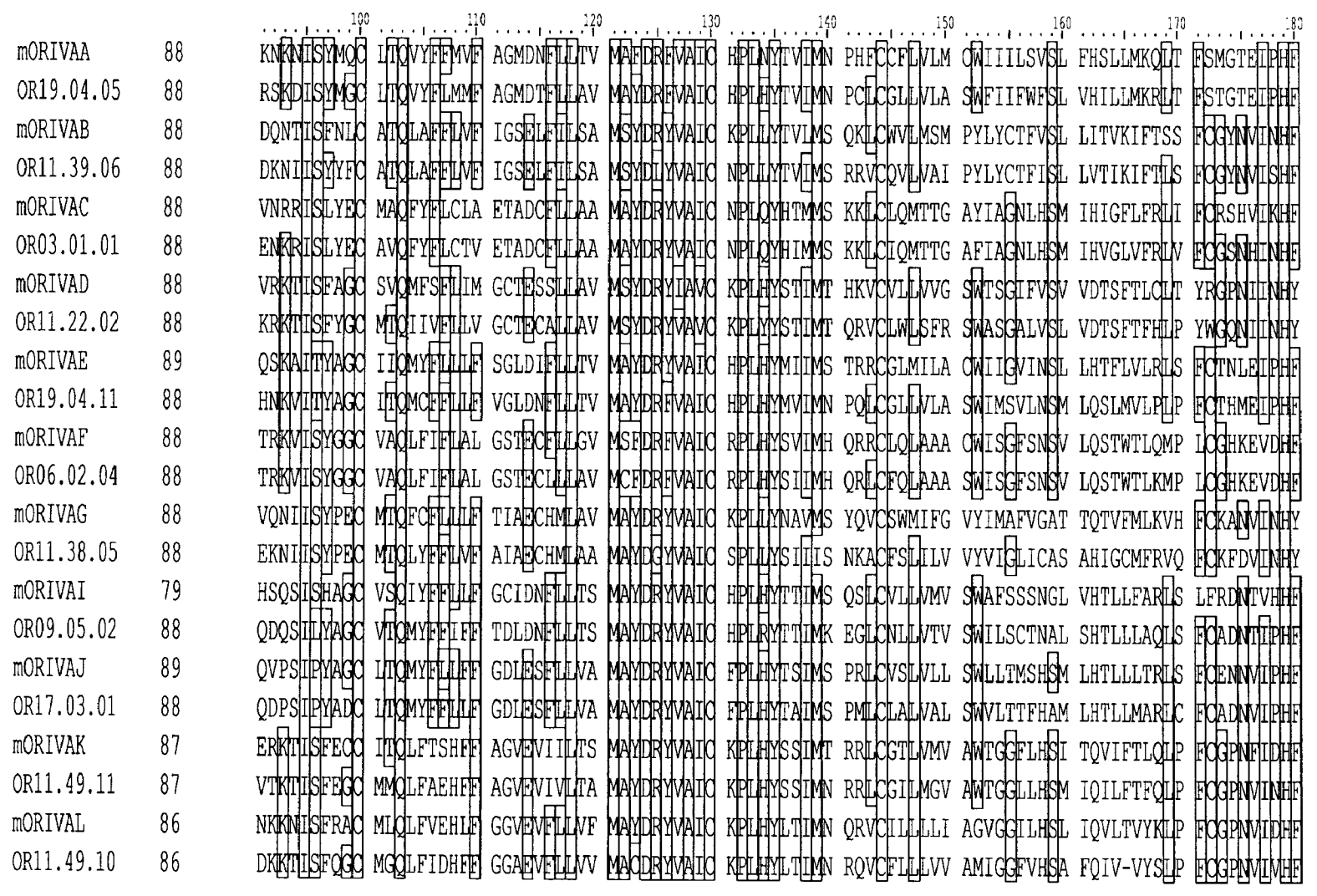
Figure 1C:
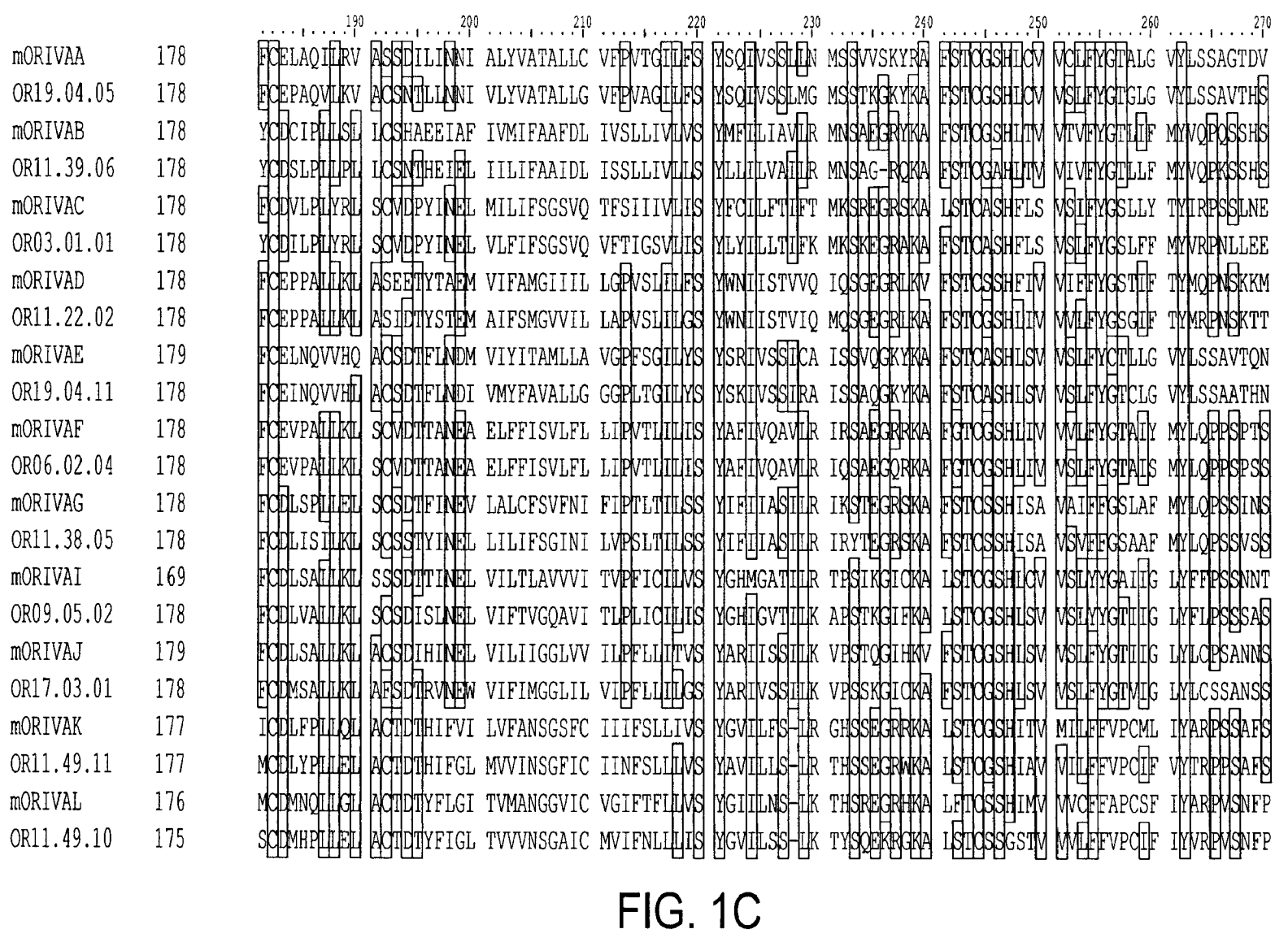

FIG. 1 depicts the multiple full-length sequence alignment for all murine IVA receptors (SEQ ID NOS 2, 4, 6, 8, 33, 12, 14, 16, 18, 20 & 22) and their predicted human counterparts (SEQ ID NOS 31, 30, 44, 32, 35, 34, 42, 36, 37, 38 & 39). Conserved amino acid positions are highlighted by black (>50% identity) or grey (>50% homology) background.

FIG. 2 depicts the multiple CDR protein sequence alignment for all murine IVA receptors (SEQ ID NOS 40, 43, 68, 70, 72, 74, 76, 78, 80, 82 & 84) and their predicted human counterparts (SEQ ID NOS 41, 67, 69, 71, 73, 75, 77, 79, 81, 83 & 85). Conserved amino acid positions are highlighted by black (>50% identity) or grey (>50% homology) background.

BRIEF DESCRIPTION AND OBJECTS OF THE INVENTION

Figure 3:
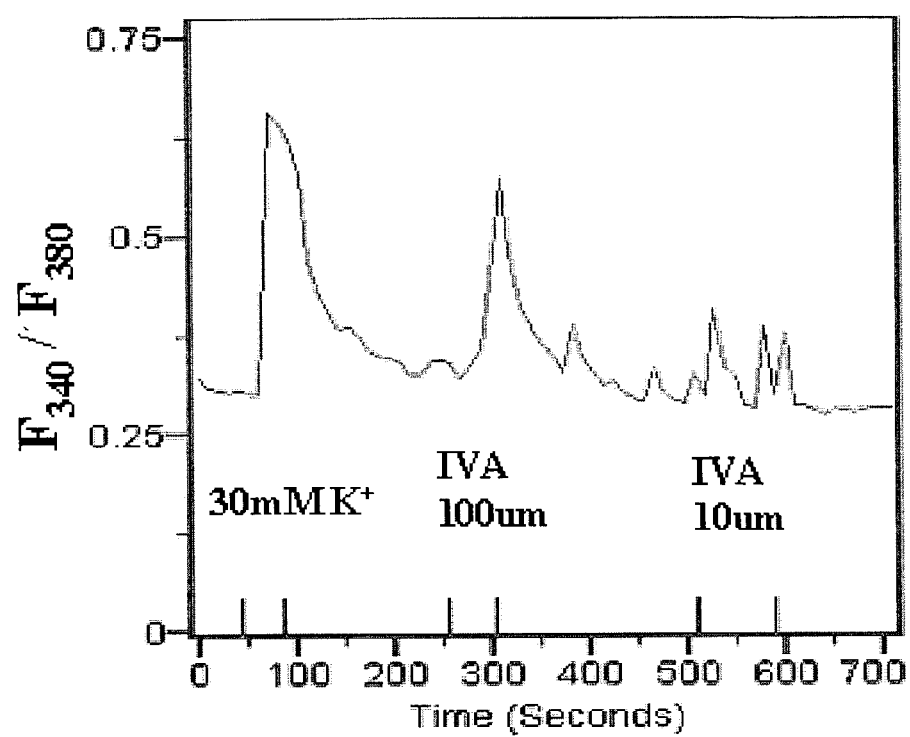
FIG. 3 depicts the response of a single olfactory neuron to IVA indicated by changes in fura-2 fluorescence intensity ratios (340/380 nm). Either high $K^+$ solution or IVA at either 100 μM or 10 μM were applied. The neuron was washed continuously between applications of high $K^+$ and IVA.

Thus, one object of the invention is to develop a greater understanding of the biological processes involved in the perception of malodor by isovaleric acid and related compounds.

It is a more specific object of the invention to identify a subgenus of mammalian olfactory receptors that specifically respond to isovaleric acid and structurally related odorants.

More specifically, it is an object of the invention to identify a subgenus of human olfactory receptors that specifically respond to isovaleric acid and structurally related compounds.

It is another specific object of the invention to develop assays, particularly high throughput screening assays, to identify compounds that block, inhibit, enhance and/or modulate specific receptor(s) that are activated by isovaleric acid and structurally related compounds.

It is a more specific object of the invention to develop assays, particularly high throughput screening assays, to identify compounds that block inhibit, enhance and/or modulate one or more of a subgenus of mammalian olfactory receptors, preferably human or murine olfactory receptors, that are activated by isovaleric acid. These assays are especially to be used for identifying compound(s) that block the malodor of isovaleric acid, a malodorous compound found in human axillary secretions.

It is another specific object of the invention to provide cell lines that stably or transiently express at least one isovaleric acid olfactory receptor according to the invention or a fragment, variant or chimera thereof and to use same in assays for identifying compounds that block, inhibit, modulate and/or enhance the activation of isovaleric acid receptors by isovaleric acid and/or structurally related malodorant compounds.

It is another object of the invention to provide a microarray of olfactory receptors that respond to isovaleric acid and/or structurally related malodorant compounds.

It is another object of the invention to use compounds that block, inhibit, modulate and/or enhance the activation of isovaleric acid receptors in compositions intended to camouflage or block the odor of isovaleric acid and structurally related compounds, e.g. deodorants, carpet fresheners, air fresheners, fabric fresheners, et al.

DETAILED DESCRIPTION OF THE INVENTION

As discussed supra, the present invention hinges on the elucidation of the odorant specifically of a specific subgenus of olfactory receptors that respond to isovaleric acid and potentially to structurally related compounds (such as other aliphatic carboxylic acids that elicit malodor such as 3-methyl-2-hexanoic acid, propionic acid, and hexenoic acid.) This goal was achieved by performing receptor activity assay experiments using a family of murine olfactory receptors in vitro to identify a subgenus of murine olfactory receptors that specifically respond to isovaleric acid. Using these sequences, the human homologs of these murine olfactory receptors were identified based on sequence similarity of the amino acid sequences of the murine olfactory IVA receptors to that of previously reported human olfactory sequences. Particularly, the present inventors compared the amino acid sequences of the identified murine isovaleric acid ORs to that of the amino acid sequences of the repertoire of human ORs disclosed in Zozulya et al., *Genome Biology* 2(6):research 0018.1–0018.12 (2001) and Zozulya, S. PCT WO 01/68805 A2, and U.S. Ser. No. 09/809,291 both having an international filing date of Mar. 13, 2001, and all of which are incorporated by reference herein in their entirety.

In particular, the murine olfactory receptors for isovaleric acid were identified using experimental techniques and procedures similar to those reported by other groups for elucidating the specificity ("de-orphan") of rodent olfactory receptors. (Touhara et al., *Proc. Natl. Acad. Sci., USA* 96(7):4040–5 (1999); Malnic et al., *Cell*, 96(5):713–23 (1999); and Dulac, C. and Axel, R., *Cell* 83(2):195–206 (1995).

Essentially, individual murine olfactory neurons isolated from an enzymatically and mechanically dissociated preparations of murine olfactory epithelium. A very mild trypsin dissociation allows to obtain a single cell suspension in which neurons still bear their axon and dendrites and can therefore be picked based on their morphology. The neurons were loaded with a $Ca^{2+}$-sensing fluorescent dye (fura-2) and contacted with isovaleric acid (at 10–100 µM). Single neurons that responded to the isovaleric acid stimulus, as indicated by transient increases in the concentration of intracellular Ca2+ were identified in a microscope field and collected using a suction microcapillary. The identified single IVA-responding neurons were then subjected to reverse transcription with $(dT)_{24}$ containing oligo primers to synthesize cDNA from poly(A) fraction of cellular mRNA.

The cDNA was then subjected to polymerase chain reaction (PCR) using degenerate oligonucleotide primers corresponding to the highly conserved regions of mammalian olfactory receptors (disclosed in Zozulya patent application and publication incorporated by reference) to amplify a fragment of a unique olfactory receptor expressed in each particular neuron. The amplified OR fragments were then cloned in a plasmid vector and their nucleotide sequences elucidated. The experimental procedures mentioned above are described in more detail in the EXAMPLES section of this application. The partial OR sequences were extended to the corresponding predicted full-length or near full-length open reading frame sequence of the corresponding OR gene by murine genomic sequence database mining. The extended sequences were conceptually translated to obtain protein sequences of murine isovaleric acid receptors. These protein sequences were then used to query the protein sequence database of human ORs using the BLAST algorithm to identify the predicted human counterparts of the murine isovaleric acid receptors based on sequence similarity.

Additionally, instead of the full-length sequences, the ligand-binding regions "complementarity determining regions (CDRs)" (as determined according to Pilpel, Y., and Lanar, D., *Protein Sci.* 8(5):969–77 (1999)) of the identified murine IVA acid ORs were to identify the human counterpart ORs based on sequence similarity. Based on this sequence comparison and analysis, the present inventors have identified a subgenus of OR genes that should bind the same or similar compounds, as the identified subgenus of murine IVA olfactory receptors, namely, these human ORs should be activated by isovaleric acid and/or structurally related compounds, e.g. other carboxylic acid odorants.

In particular, based on the results of the above-described experiments and sequence analysis, the present inventors have identified eleven (11) murine olfactory receptors that are activated by isovaleric acid and eleven predicted human homologs thereof that should respond similarly to isovaleric acid and/or structurally related compounds.

Based on the particular human and murine olfactory receptor libraries that were screened, the current understanding of this family of receptors, and using available screening methods it is believed that the present inventors have identified the full repertoire of murine and olfactory receptors that are activated by isovaleric acid. It is anticipated that these receptors, as well as fragments, chimeras and variants thereof will be well suited for identifying compounds that block, inhibit modulate and/or enhance the activation of these receptors. In particular, it is anticipated that these receptors alone or in combination may be utilized to screen libraries for compounds that bind these receptors. It is especially anticipated that these assays may yield commercially significant malodorants.

A particular advantage of the subject invention is that it provides a repertoire of isovaleric acid receptors that likely recognize isovaleric acid with different affinities and/or recognize different structural determinants of the isovaleric acid molecule. Therefore, the subject receptors in combination should be useful in assays for identifying compounds that are structurally related to isovaleric acid, some of which may yield effective malodorants, especially for blocking the malodor of isovaleric acid and related chemical compounds.

The predicted DNA and amino acid sequences of the eleven isovaleric acid murine olfactory receptors expressed in isovaleric acid-responding olfactory neurons are set forth below:

mOR IVA A (DNA Sequence)

SEQ ID NO:1
ATGGGAAAAGAAAATCACACAGAACTATCACAATTCCTGCTACTGGGTCT

CTCAGATGATCCTAAATTGCAGCCTATTCTTTTCGGGATATTCTTATTTA

TGTACCTGGTCACAGTGCTTGGTAACCTGCTCATCATCCTGGCTGTCAGT

TCTGATTCCCATCTCCACAACCCCATGTACTTCTTCCTCTCCAACCTCTC

ATTTGTAGACATGTGTTTCACTTCTACCACTGTCCCAAAGATGCTGGTGA

ACATCCAGACAAAGAACAAAAATATCTCCTACATGCAGTGCCTCACTCAA

GTCTATTTTTTTATGGTGTTTGCTGGAATGGATAATTTCTTACTGACTGT

```
AATGGCCTTTGACCGCTTTGTGGCTATTTGTCACCCCTTAAACTACACAG
TCATCATGAACCCTCACTTCTGTTGCTTCCTTGTGCTAATGTGCTGGATT
ATCATTTTATCAGTCTCCCTGTTTCATAGTCTATTAATGAAGCAATTAAC
TTTTTCCATGGGTACTGAAATCCCACATTTCTTCTGTGAGTTGGCTCAAA
TTCTCAGAGTAGCAAGCTCTGATATTCTCATCAATAATATCGCATTATAT
GTGGCTACTGCCCTGTTATGTGTGTTTCCTGTCACTGGAATTCTCTTCTC
TTACTCGCAGATTGTCTCCTCCTTATTGAATATGTCTTCAGTAGTCAGCA
AGTATAGAGCCTTTTCCACCTGTGGATCTCACCTCTGTGGTCTGTTTG
TTTTATGGTACAGCACTGGGGGTTTACCTCAGTTCAGCTGGGACTGATGT
TTCTCAAGGAAGCACTATAGCCTCAGTGATGTATACTGTGGTCACTCCTA
TGCTCAACCCATTCATCTACAGCCTGAGGAATAAAGATGTGAAGGGGCT
CTGGTAAGAATCCTTAAAGTATATTCTTGTCCCTGA
``` mOR IVA A (Amino Acid Sequence)

SEQ ID NO:2

```
MGKENHTELSQFLLLGLSDDPKLQPILFGIFLFMYLVTVLGNLLIILAVS
SDSHLHNPMYFFLSNLSFVDMCFTSTTVPKMLVNIQTKNKNISYMQCLTQ
VYFFMVFAGMDNFLLTVMAFDRFVAICHPLNYTVIMNPHFCCFLVLMCWI
IILSVSLFHSLLMKQLTFSMGTEIPHFFCELAQILRVASSDILINNIALY
VATALLCVFPVTGILFSYSQIVSSLLNMSSVVSKYRAFSTCGSHLCVVCL
FYGTALGVYLSSAGTDVSQGSTIASVMYTVVTPMLNPFIYSLRNKDVKGA
LVRILKVYSCP
``` mOR IVA B (DNA Sequence)

SEQ ID NO:3

```
ATGGAAGAACACAATCTTACATTAATGACTGAATTCATCCTAATGGGTAT
CAGTGACCACTCTGAATTGCAGGCCCGATTATTTGGGCTGATCCTTGCCA
TATACATGACCTCAATGGTAGGTAATATGGGAATCATTGTTTTAATCACT
TTGGACTCACGCCTGCTAACACCCATGTACTTCTTTATAAAACACCTGGC
TATTACAGATCTTGGATATTCTACAGCTGTGGGACCCAAAATGTTGGAAA
ATTTTGTTGTAGATCAAAATACAATTTCATTTAATCTTTGTGCCACACAA
CTAGCTTTCTTTCTTGTATTCATTGGTAGTGAGCTATTCATTCTCTCTGC
GATGTCCTATGACCGCTATGTGGCCATCTGTAAGCCTCTGCTCTACACTG
TCCTCATGTCCCAAAAACTATGTTGGGTTCTTATGTCAATGCCTTATCTC
TACTGCACATTTGTGTCTCTTCTCATCACAGTGAAGATTTTTACTTCATC
CTTCTGTGGCTACAATGTCATTAACCATTTCTACTGTGACTGTATCCCCT
TGCTGTCTCTACTCTGTTCACATGCGAGAGGAAATCGCATTTATTGTTATG
ATCTTTGCAGCTTTTGATTTGATTGTGTCTCTTCTTATTGTTCTGGTATC
CTACATGTTTATCCTCATAGCAGTTCTCAGGATGAACTCTGCAGAGGGCA
GGTACAAGGCTTTCTCCACATGTGGGTCCCACCTGACAGTGGTGACAGTG
TTCTATGGTACTTTAATATTTATGTATGTACAACCTCAGTCCAGTCATTC
TGATGACAATGATAAGGTGTCTTCAATTTTTTACACCCTCGTTATACCCA
TGCTGAATCCTTTGATCTATAGTTTGAGGAACAAGGATGTAAAATTTGCC
CTACATAGGACTTGGAGAAATATTTGTAAGATCTTCCCTTAG
``` mOR IVA B (Amino Acid Sequence)

SEQ ID NO:4

```
MEEHNLTLMTEFILMGISDHSELQAPLFGLILAIYMTSMVGNMGIIVLIT
LDSRLLTPMYFFIKHLAITDLGYSTAVGPKMLENFVVDQNTISFNLCATQ
LAFFLVFIGSELFILSAMSYDRYVAICKPLLYTVLMSQKLCWVLMSMPYL
YCTFVSLLITVKIFTSSFCGYNVINHFYCDCIPLLSLLCSHAEEIAFIVM
IFAAFDLIVSLLIVLVSYMFILIAVLRMNSAEGRYKAFSTCGSHLTVVTV
FYGTLIFMYVQPQSSHSDDNDKVSSIFYTLVIPMLNPLIYSLRNKDVKFA
LHRTWRNICKIFP
``` mOR IVA C (DNA Sequence)

SEQ ID NO:5

```
ATGACTGAGGACAACTACTCCTTGACAACAGAGTTCATCCTCATAGGATT
CTCAGACCACCCAGACTTAAAGATACTTCTATTCCTGGTGTTATCTACCA
TCTATCTGGTCACCATGGTGGGGAATCTTGGCTGGTGGCCTTGATCTAC
ATGGAGCCTCGTCTCCACACACCCATGTACATCTTTCTGGGCAACCTGGC
TCTCATGGATTCCTGTTGCTCCTGTGCCATCACTCCTAAGATGCTAGAGA
ACTTTTTTTCTGTGAACAGAAGGATTTCTCTCTATGAATGCATGGCACAG
TTCTATTTTCTCTGTCTTGCTGAAACTGCAGACTGCTTCCTTCTGGCAGC
CATGGCCTATGACCGCTATGTGGCCATATGCAACCCTCTGCAGTACCACA
CCATGATGTCCAAGAAGCTCTGCCTTCAAATGACCACAGGAGCCTACATA
GCAGGAAACCTGCATTCCATGATTCACATAGGGTTCTTGTTCAGGTTAAT
TTTCTGCAGGTCTCATGTGATCAAGCACTTCTTTTGTGATGTCCTCCCCC
TATACAGACTCTCATGTGTTGACCCTTATATCAATGAACTGATGATACTC
ATCTTTTCTGGTTCAGTTCAAACCTTTTCCATTATTATAGTCTTGATTTC
TTATTTCTGCATCCTTTTTACTATATTCACAATGAAGTCCAGAGAGGGAA
GAAGCAAAGCCTTATCTACTTGTGCATCCCACTTTCTGTCTGTGTCAATA
TTCTATGGGTCTCTTCTCTACACATATATTCGACCAAGTTCACTTAATGA
AGGGTATAAAGACATACCTGTTGCTATATTTTATACTCTAGTAATTCCTT
TATTAAACCCGTTTATTTATAGTCTGAGAAATAAGAAGTAATTAATGTG
ATGAAAAGAGCAATGAAGAAAAGATTATAA
``` mOR IVA C (Amino Acid Sequence)

SEQ ID NO:6

```
MTEDNYSLTTEFILIGFSDHPDLKILLFLVLSTIYLVTMVGNLGLVALIY
MEPRLHTPMYIFLGNLALMDSCCSCAITPKMLENFFSVNRRISLYECMAQ
FYFLCLAETADCFLLAAMAYDRYVAICNPLQYHTMMSKKLCLQMTTGAYI
AGNLHSMIHIGFLFRLIFCRSHVIKHFFCDVLPLYRLSCVDPYINELMIL
IFSGSVQTFSIIIVLISYFCILFTIFTMKSREGRSKALSTCASHFLSVSI
```

-continued

FYGSLLYTYIRPSSLNEGYKDIPVAIFYTLVIPLLNPFIYSLRNKEVINV
MKRAMKKRL mOR IVA D (DNA Sequence)

SEQ ID NO:7
ATGGGCAAATTAAACCACACTTATCTGACGGAGTTCATCTTGCTGGGCCT
CTCTTCAGATCATCAGACTCAGATCCTGCTGTTTGTGGTATTTCTCATCA
TCTACCTGATCACTGTGTTTGGGAACCTGCTCATCATACTCCTCATTCAT
GTTGACTCCCGACTTCATACACCAATGTACTTCTTTCTAAAAATCCTGTC
ATTCAATGATCTCTGTTTCTCTACAACAATTGTTCCAAAGATGCTAGTCC
ACTTTCTAGGTGTCAGAAAGACCATTTCATTTGCTGGGTGCTCAGTGCAA
ATGTTTTCTTTCCTCATAATGGGGTGTACAGAAAGCTCTCTTCTGGCAGT
CATGTCATATGACCGCTACATAGCTGTCTGCAAACCCCTGCACTACTCCA
CCATCATGACACATAAGGTTTGTGTTCTGCTAGTTGTAGGATCCTGGACT
AGTGGAATATTTGTGTCTGTAGTAGATACCTCATTTACTTTATGCTTGAC
GTACCGGGGACCAAATATAATCAATCATTACTTTTGTGAGCCTCCTGCAC
TCTTAAAGCTGGCTTCAGAAGAAACCTACACAGCTGAAATGGTCATATTT
GCAATGGGTATAATAATTCTCTTAGGTCCTGTCTCTCTTATCCTTTTCTC
CTATTGGAATATTATCTCCACTGTGGTTCAAATACAATCAGGTGAGGGGA
GGCTCAAGGTTTTCTCTACCTGGAGTTCCCATTTTATTGTTGTTATCTTC
TTCTATGGCTCAACAATATTTACCTACATGCAGCCAAACTCAAAGAAAAT
GAATGAAAAGGATAAGGTAATCTCGGTATTCTACTCAATAGTAACATCCA
TGATGAACCCATTCATTTATAGCCTAAGGAACAAAGATGTGAAAGGGGCA
TTAAAGAAAGTACTTAAAAGAGAGATAAGATAA mOR IVA D (Amino Acid Sequence)

SEQ ID NO:8
MGKLNHTYLTEFILLGLSSDHQTQILLFVVFLIIYLITVFGNLLIILLIH
VDSRLHTPMYFFLKILSFNDLCFSTTIVPKMLVHFLGVRKTISFAGCSVQ
MFSFLIMGCTESSLLAVMSYDRYIAVCKPLHYSTIMTHKVCVLLVVGSWT
SGIFVSVVDTSFTLCLTYRGPNIINHYFCEPPALLKLASEETYTAEMVIF
AMGIIILLGPVSLILFSYWNIISTVVQIQSGEGRLKVFSTCSSHFIVVIF
FYGSTIFTYMQPNSKKMNEKDKVISVFYSIVTSMMNPFIYSLRNKDVKGA
LKKVLKREIR mOR IVA E (DNA Sequence)

SEQ ID NO:9
ATGGAAACAGGAAATGACACTCAGCTTTCAGAATTCTTTCTTCTGGGATT
TTCAGAGAATCAACCTCAAATTCAGCCTGTCATATTTGGACTGTTCCTCT
TCATGTATATATTGACTTTCACTGGAAACCTACTCATCATCATGGCCATC
ATTGTTGACTCGCACCTCCACACACCCATGTACCTCTTCCTCTCTAATCT
GTCCTTTGTGGACATCTGCTTCACTTCCACCACTGTTCCACAGATGCTGG
TAAACATTCACACACAAAGCAAGGCCATCACCTATGCAGGCTGCATCATC
CAGATGTACTTCTTACTGCTTTTTTCAGGGTTAGACATCTTTCTGCTGAC

-continued

TGTGATGGCCTATGACCGCTATGTGGCCATCTGTCACCCCCTGCATTACA
TGATCATCATGAGCACAAGACGCTGTGGATTGATGATTCTGGCATGCTGG
ATTATAGGTGTTATAAATTCCCTGTTACACACCTTTTTGGTGTTACGGCT
GTCATTCTGCACAAACTTGGAAATCCCCCATTTTTTCTGTGAACTTAATC
AAGTTGTACACCAGGCCTGTTCTGACACCTTTCTTAATGATATGGTAATT
TACATTACAGCTATGCTACTGGCTGTTGGCCCCTTCTCTGGTATCCTTTA
CTCTTACTCTAGGATAGTATCCTCCATTTGTGCAATCTCCTCAGTGCAGG
GGAAGTACAAAGCATTTTCCACCTGTGCATCTCACCTCTCAGTTGTCTCC
TTATTTTATTGCACCCTCCTGGGAGTGTACCTCAGCTCTGCTGTGACCCA
AAACTCACATGCTACTGCAACAGCTTCATTGATGTACACTGTGGTCACCC
CCATGCTGAATCCCTTCATCTACAGTCTGAGGAACAAAGACATAAAGACA
GCTCTGAAAATCCTGTTAGGGAGTGTAACTAGAAGCAGATCAATGGATTC
ACCTTCATAA mOR IVA E (Amino Acid Sequence)

SEQ ID NO:10
METGNDTQLSEFFLLGFSENQPQIQPVIFGLFLFMYILTFTGNLLIIMAI
IVDSHLHTPMYLFLSNLSFVDICFTSTTVPQMLVNIHTQSKAITYAGCII
QMYFLLLFSGLDIFLLTVMAYDRYVAICHPLHYMIIMSTRRCGLMILACW
IIGVINSLLHTFLVLRLSFCTNLEIPHFFCELNQVVHQACSDTFLNDMVI
YITAMLLAVGPFSGILYSYSRIVSSICAISSVQGKYKAFSTCASHLSVVS
LFYCTLLGVYLSSAVTQNSHATATASLMYTVVTPMLNPFIYSLRNKDIKT
ALKILLGSVTRSRSMDSP mOR IVA F (DNA Sequence)

SEQ ID NO:11
ATGAGTGTGGCCAATGAGAGCATCTCACGGGAGTTCATTCTCTTAGGGTT
TTCAGATCGGCCATGGCTGGAGCTGCCGCTCTTTGTGGTGTTTCTAGTGT
CCTATATTCTGACCATCTTTGGAAATATGATGATCATTCTTGTGTCCCGC
CTGGATTCCAAACTCCACACCCCCATGTACTTTTTCCTCACTAACCTGTC
CTTGCTGGACCTGTGCTACACCACAAGCACGGTCCCACAGATGCTCATCA
ACATCTGCAGCACCCCGGAAGGTGATCAGCTATGGTGGCTGTGTGGCCCAG
CTTTTCATTTTCCTGGCCTTGGGTTCCACAGAATGCTTTCTGCTGGGCGT
CATGTCCTTTGACAGGTTTGTAGCCATCTGTCGGCCTCTCCACTACTCAG
TCATCATGCACCAGAGGCGCTGCCTCCAGTTGGCGGCTGCATGTTGGATC
AGTGGCTTCAGCAACTCAGTATTACAGTCTACGTGGACCCTTCAGATGCC
ACTGTGTGGACACAAGGAAGTGGACCATTTCTTTTGCGAAGTCCCTGCCC
TGCTCAAGTTGTCCTGTGTGGATACGACAGCTAATGAAGCAGAGCTGTTC
TTCATCAGTGTGCTGTTTCTTTTAATACCCGTGACCCTCATCCTCATATC
ATATGCTTTTATTGTCCAGGCAGTGTTGAGAATAAGATCAGCTGAAGGTC
GGCGAAAGGCATTTGGGACATGTGGCTCCCACCTCATCGTGGTGGTCCTT
TTCTATGGCACTGCCATCTACATGTATCTGCAGCCACCATCCCCTACTTC
CAAGGACCGGGGGAAAATGGTGTCTCTCTTTTATGGGATCATCACACCCA

-continued
TGCTGAACCCCCTCATCTACACACTCAGGAACAAAGAGGTAAAGGGAGCG
TTCAAGAGGTTGGTGACAAGGATCATCCTGAGTAGAAAATAA mOR IVA F (Amino Acid Sequence)

SEQ ID NO:12
MSVANESISREFILLGFSDRPWLELPLFVVFLVSYILTIFGNMMIILVSR
LDSKLHTPMYFFLTNLSLLDLCYTTSTVPQMLINICSTRKVISYGGCVAQ
LFIFLALGSTECFLLGVMSFDRFVAICRPLHYSVIMHQRRCLQLAAACWI
SGFSNSVLQSTWTLQMPLCGHKEVDHFFCEVPALLKLSCVDTTANEAELF
FISVLFLLIPVTLILISYAFIVQAVLRIRSAEGRRKAFGTCGSHLIVVL
FYGTAIYMYLQPPSPTSKDRGKMVSLFYGIITPMLNPLIYTLRNKEVKGA
FKRLVTRIILSRK mOR IVA G (DNA Sequence)

SEQ ID NO:13
ATGTTCCAAGGAAATCTTTCCGGAGTAACTGAGTTCAATCTTGCTGGTTT
AACAGACAAACCAGGGCTGCAGCTGCCCCTCTTCCTCCTGTTCCTAGGAA
TCTATGTGGTCACAGTGGTGGGAATCTCAGCATGATCACCCTGATACTA
TTCAGTTCTCAACTACACACACCCATGTATTATTTTCTCAGCAGTCTGTC
CTTCATTGACCTCTGCCAGTCCATTGTCATTATTCCCAAAATGTTGGTGA
ACTTTGTGACAGTGCAGAACATCATCTCCTACCCTGAATGTATGACACAG
TTTTGCTTTTGCTACTTTTACTATTGCAGAGTGTCACATGTTAGCTGT
AATGGCATATGACCGCTATGTTGCCATTTGTAAGCCCTTGCTTTACAATG
CTGTAATGTCCTATCAAGTTTGTTCCTGGATGATATTTGGAGTATATATT
ATGGCTTTTGTTGGTGCCACAACTCAAACAGTCTTCATGTTAAAAGTGCA
TTTTTGTAAGGCCAATGTAATAAATCATTACTTCTGTGATCTTTCCCCAC
TCCTGGAACTCTCTTGTTCTGATACTTTTATTAATGAAGTATTAGCTTTG
TGCTTCAGTGTTTTCAATATCTTTATTCCAACTCTGACAATTCTAAGCTC
TTACATCTTCATCATAGCCAGCATCCTCCGGATTAAATCCACTGAAGGCA
GGTCCAAAGCCTTCAGCACTTGCAGCTCACACATATCAGCAGTTGCTATA
TTCTTTGGATCCCTTGCATTCATGTACCTGCAGCCATCATCAATCAACTC
CATGGACCAAAGGAAAGTGTCCTCTGTATTTTATACCATTGTCGTGCCCA
TGCTGAATCCTTTGATCTACAGCCTGAGGAATAAGGATGTCAAAGTTGCT
CTAAATAAGTTCCTTGAAAGAATTTTTTCTTGTGAACAAACTAA mOR IVA G (Amino Acid Sequence)

SEQ ID NO:14
MFQGNLSGVTEFNLAGLTDKPGLQLPFLLFLGIYVVTVVGNLSMITLIL
FSSQLHTPMYYFLSSLSFIDLCQSIVIIPKMLVNFVTVQNIISYPECMTQ
FCFLLLFTIAECHMLAVMAYDRYVAICKPLLYNAVMSYQVCSWMIFGVYI
MAFVGATTQTVFMLKVHFCKANVINHYFCDLSPLLELSCSDTFINEVLAL
CFSVFNIFIPTLTILSSYIFIIASILRIKSTEGRSKAFSTCSSHISAVAI

-continued
FFGSLAFMYLQPSSINSMDQRKVSSVFYTIVVPMLNPLIYSLRNKDVKVA
LNKFLERIFSCEQN mOR IVA I (DNA Sequence)

SEQ ID NO:15
TCTGAGTTTATCCTCTTAGAGCTCCCCATTCAGCCAGAGGATCAAGCTGT
GTACTTTGCCCTGTTCCTGGCCATGTACCTGACAACTGTGCTGGGGAACC
TGCTCATCATTCTTCTCATTAGGCTGGACTCTCACCTCCACACCCCCATG
TACTTCTTCCTCAGTCACTTGGCCTTCACGGACATCTCTTTCTCATCTGT
CACAGCTCCAAAGATGCTCATGAATATGCTGACACATAGCCAATCCATCT
CACATGCTGGGTGTGTTTCCCAAATATATTTTTTCTTATTGTTTGGGTGT
ATTGACAACTTCCTTCTGACTTCCATGGCCTATGACAGGTATGTGGCCAT
CTGCCACCCTCTGCATTATACCACTATCATGAGTCAAAGCCTCTGTGTTC
TGCTAGTGATGGTGTCCTGGGCATTTTCCTCTTCTAATGGCCTTGTGCAT
ACTCTTCTCTTTGCTCGTCTCTCTCTTTTTAGAGACAACACTGTCCACCA
TTTTTTCTGTGATCTCTCTGCTTTGCTGAAGCTGTCCAGCTCAGACACTA
CTATCAATGAACTAGTAATCCTCACTTTAGCAGTGGTGGTCATCACTGTA
CCATTCATATGCATCCTGGTTTCTTATGGCCACATGGGGGCCACTATCCT
AAGAACTCCATCCATCAAGGGTATCTGCAAAGCCTTGTCCACATGTGGTT
CTCATCTCTGTGTAGTTTCTTTATATTATGGAGCCATTATTGGGTTATAT
TTTTTTCCCCTCCTCCAATAATACTAATGATAAAGATGTCATAGTAGCTGT
GTTGTACACTGTGGTTACACCCATGCTGAATCCCTTTATCTATAGTCTGA
GGAATCGGGATATAAATGGAGCATTGAGAAAGACACTCAGCAGGAGACTG
TGTTCACACTGA mOR IVA I (Amino Acid Sequence)

SEQ ID NO:16
SEFILLELPIQPEDQAVYFALFLAMYLTTVLGNLLIILLIRLDSHLHTPM
YFFLSHLAFTDISFSSVTAPKMLMNMLTHSQSISHAGCVSQIYFFLLFGC
IDNFLLTSMAYDRYVAICHPLHYTTIMSQSLCVLLVMVSWAFSSSNGLVH
TLLFARLSLFRDNTVHHFFCDLSALLKLSSSDTTINELVILTLAVVVITV
PFICILVSYGHMGATILRTPSIKGICKALSTCGSHLCVVSLYYGAIIGLY
FFPSSNNTNDKDVIVAVLYTVVTPMLNPFIYSLRNRDINGALRKTLSRRL
CSH mOR IVA J (DNA Sequence)

SEQ ID NO:17
ATGCCTAGAACAACAACCAGACTACCATCTCTCAGTTCCTCCTCCTGGG
TCTGCCCATCCCCCAAGAGTTTCAGCATCTGTTCTATGCCCTGTTCCTGG
CCATGTACCTCACCACTGTCTTGGGGAACCTCATCATCATCATACTCATT
CGACTGGACTCCCATCTCCACACACCCATGTACTTGTTTCTCAGCAACTT
GTCCTTCACTGACCTCTAATTTTCCTCTGTCACAATGCCCAAGTTGCTGC
AGAACATGCAGAGCCAAGTTCCTTCAATCCCCTATGCAGGCTGCCTGACA
CAAATGTACTTCCTTTTGTTTTTTGGAGATCTTGAGAGCTTCCTCCTTGT

-continued
```
GGCCATGGCCTATGACCGCTATGTAGCCATCTGCTTCCCTCTTCATTACA

CCAGCATCATGAGCCCCAGGCTCTGTGTGAGTCTTGTGCTGCTGTCCTGG

TTGCTGACCATGTCCCATTCCATGCTGCACACTTTGCTCTTAACTAGGTT

GTCTTTCTGTGAAAACAATGTGATCCCCCATTTTTTCTGTGATCGTCTG

CTCTGCTGAAGCTGGCCTGCTCTGATATTCACATTAATGAATTGGTGATA

TTGATCATAGGAGGGCTTGTTGTTATACTTCCATTTCTACTCATCACAGT

GTCTTATGCACGCATCATCTCCTCCATTCTCAAGGTCCCTTCAACTCAAG

GCATCCACAAGGTCTTCTCCACTTGTGGTTCTCACCTGTCTGTGGTGTCA

CTGTTCTATGGGACAATTATTGGCCTCTACTTATGTCCATCTGCTAATAA

CTCTACTCTAAAGGACACTGTCATGTCTATGATGTACACCGTGGTAACTC

CCATGCTGAACCCCTTCATCTACAGCCTGAGGAACAGAGACATGAAGGAA

GCCCTAAAAAGAGTGCTTCAAAAGAAAACTATCTTTTGA
``` mOR_IVA_J (Amino Acid Sequence)

SEQ ID NO:18
```
MPRNNNQTTISQFLLLGLPIPQEFQHLFYALFLAMYLTTVLGNLIIIILI

RLDSHLHTPMYLFLSNLSFTDLXFSSVTMPKLLQNMQSQVPSIPYAGGLT

QMYFLLFFGDLESFLLVAMAYDRYVAICFPLHYTSIMSPRLCVSLVLLSW

LLTMSHSMLHTLLLTRLSFCENNVIPHFFCDLSALLKLACSDIHINELVI

LIIGGLVVILPFLLITVSYARIISSILKVPSTQGIHKVFSTCGSHLSVVS

LFYGTIIGLYLCPSANNSTLKDTVMSMMYTVVTPMLNPFIYSLRNRDMKE

ALKRVLQKKTIF
``` mOR_IVA_K (DNA Sequence)

SEQ ID NO:19
```
ATGCAAAACCAGAGCTTTGTCACTGAGTTCATACTCTTGGGGCTTTCCCA

GAACCCAAAAGTTGAGAAAATACTGTTTGTTGTATTTTTATTGGTCTATA

TTGCAACTATTGGGGGAAACATGATAATTGTGGTGACCATCATCTATAGC

CCTGCACTGTTGAGTTCCCCCATGTACTTCTTCTTAATATTTCTGTCTTT

CCTGGATGCTTGCACTTCCTCTACTGTCACCCCCAAGATGATTGTAGACT

TCTTCTATGAGAGGAAGACCATCTCCTTTGAATGTTGCATCACACAACTG

TTTACTAGCCACTTCTTTGCAGGAGTTGAGGTGATTATCTTGACATCTAT

GGCCTATGACCGCTATGTGGCCATCTGCAAGCCTCTTCACTACTCTTCCA

TCATGACCAGGAGGCTCTGTGGCACTCTCGTAATGGTGGCCTGGACAGGA

GGATTCTTACATTCTATCACACAAGTTATCTTCACGTTGCAGCTACCCTT

CTGTGGGCCCAATTTTATTGATCATTTCATATGTGACTTGTTCCCATTAC

TGCAGCTTGCCTGCACTGACACACACATTTTTGTCATTTTGGTGTTTGCT

AATAGTGGGTCTTTCTGCATCATTATCTTCTCCTTGTTGATTGTTTCCTA

TGGTGTCATCCTCTTCTCTCTAAGAGGTCACAGCTCAGAAGGACGAAGGA

AAGCTCTCTCAACCTGTGGATCCCATATTACTGTTATGATATTATTCTTT

GTCCCATGTATGCTAATATATGCACGGCCTTCATCTGCCTTTTCCTTTGA

GAAAAACACACTTATATTTGCCTCTGTCCTGACACCATTGTTCAATCCTA

TGGTTTACACTTTCAGAAATAAAGAAATGAAGAATGCCATCAGGAAAATG

TGTAGGAAAATGTTAGTAGATTCTGATAACTTTTAA
``` mOR_IVA_K (Amino Acid Sequence)

SEQ ID NO:20
```
MQNQSFVTEFILLGLSQNPKVEKILFVVFLLVYIATIGGNMIIVVTIIYS

PALLSSPMYFFLIFLSFLDACTSSTVTPKMIVDFFYERKTISFECCITQL

FTSHFFAGVEVIILTSMAYDRYVAICKPLHYSSIMTRRLCGTLVMVAWTG

GFLHSITQVIFTLQLPFCGPNFIDHFICDLFPLLQLACTDTHIFVILVFA

NSGSFCIIIFSLLIVSYGVILFSLRGHSSEGRRKALSTCGSHITVMILFF

VPCMLIYARPSSAFSFEKNTLIFASVLTPLFNPMVYTFRNKEMKNAIRKM

CRKMLVDSDNF
``` mOR_IVA_L (DNA Sequence)

SEQ ID NO:21
```
ATGGGACAGAACCACAATGTCACAGAATTCATTTTTGTGGGTCTTAGTCA

AGATCCTGCTGGGCAAAAAGTATTATTTGTCTTGTTTTCACTGACTTACA

TTGTGACAATGTTCGGAAACCTGCTCATTGCACTTACAGTGATTGCCAGC

CCCTCCTTAAACTCCCCAATGTACTTCTTCCTTGCCTGTCTGTCAGTCCT

GGATGCTCTTTATTGCAATACAATCTCACCAAATTTGATTATAGACTTGT

TATATAATAAAAAGAATATCTCCTTCAGAGCTTGCATGCTCCAGCTGTTT

GTAGAGCACTTATTTGGAGGTGTTGAGGTCTTCCTTCTGGTATTCATGGC

CTATGATCGCTATGTGGCCATCTGTAAGCCACTGCACTATTTGACCATCA

TGAACCAGAGGGTGTGCATTCTTCTATTGCTGATAGCTGGAGTTGGAGGC

ATCTTACACTCACTGATTCAAGTTCTGACTGTGTATAAACTTCCTTTTTG

TGGTCCCAATGTCATTGATCACTTCATGTGTGACATGAATCAATTACTCG

GGCTTGCATGCACTGACACCTACTTCCTTGGCATCACTGTCATGGCCAAT

GGTGGAGTAATCTGTGTGGGAATTTTCACCTTTCTCTTAGTCTCCTATGG

AATCATTCTAAACTCTCTTAAGACCCACAGTCGGGAAGGAAGACATAAAG

CTCTGTTTACCTGCAGTTCTCACATCATGGTTGTTGTCTGCTTTTTTGCT

CCCTGTAGTTTTATATATGCTAGACCTGTCTCCAACTTTCCAGTGGATAA

ATATATTGCTGTGTTTTATACAGTTGTTAGTCCCATGCTGAATCCATTGA

TATATACCTTGAGAAATTCAGAGATGAAAAACTCTATTAAAAAGCTCTGG

TGTAAAACTCTAACAACATAA
``` mOR_IVA_L (Amino Acid Sequence)

SEQ ID NO:22
```
MGQNHNVTEFIFVGLSQDPAGQKVLFVLFSLTYIVTMFGNLLIALTVIAS

PSLNSPMYFFLACLSVLDALYCNTISPNLIIDLLYNKKNISFRACMLQLF

VEHLFGGVEVFLLVFMAYDRYVAICKPLHYLTIMNQRVCILLLLIAGVGG

ILHSLIQVLTVYKLPFCGPNVIDHFMCDMNQLLGLACTDTYFLGITVMAN

GGVICVGIFTFLLVSYGIILNSLKTHSREGRHKALFTCSS
```

As noted above, the amino acid and DNA sequences for the predicted human homolog of the above-identified murine olfactory receptors for isovaleric acid are disclosed in the Zozulya publications incorporated by reference in their entirety herein. (Zozulya, S., PCT WO 01/68805 A2, filed Mar. 13, 2001; Zozulya et al., *Genome Biol.* 2(6): research 0018.1–0018.12 (2001) and are identified by the following identifiers therein:
OR19.04.05 (AOLFR262);
OR19.04.11 (AOLFR284);
OR09.05.02 (AOLFR299);
OR17.03.01 (AOLFR258);
OR11.22.02 (AOLFR108);
OR06.02.04 (AOLFR269);
OR11.49.11 (AOLFR058);
OR11.49.10 (AOLFR022);
OR11.39.06 (AOLFR074);
OR11.38.05 (AOLFR346); and
OR03.01.01 (AOLFR340).

The predicted DNA and amino acid sequences for these human genes is set forth below:

```
OR11.22.02 (AOLFR108) (DNA Sequence)
ATGTGTTCTTTTTTCTTGTGGCAAACAGGTAAACAGGCAAAAATATCAATGGGA          SEQ ID NO:23

GAAGAAAACCAAACCTTTGTGTCCAAGTTTATCTTCCTGGGTCTTTCACAGGAC

TTGCAGACCCAGATCCTGCTATTTATCCTTTTCCTCATCATTTATCTGCTGACCG

TGCTTGGAAACCAGCTCATCATCATTCTCATCTTCCTGGATTCTCGCCTTCACA

CTCCCATGTATTTTTTCTTAGAAATCTCTCCTTTGCAGATCTCTGTTTGTCTACT

AGCATTGTCCCTCAAGTGTTGGTTCACTTCTTGGTAAAGAGGAAAACCATTTCT

TTTTATGGGTGTATGACACAGATAATTGTCTTTCTTGTGGTTGGGTGTACAGAG

TGTGCGCTGCTGGCAGTGATGTCCTATGACCGGTATGTGGCTGTCTGCAAGCC

CCTGTACTACTCTACCATCATGACACAACGGGTGTGTCTGGCTGTCCTTCAG

GTCCTGGGCCAGTGGGCACTAGTGTCTTTAGTAGATACCAGCTTTACTTTCCA

TCTTCCCTCTGGGGACAGAATATAATCAATCACTACTTTTGTGAACCTCCTGC

CCTCCTGAAGCTGGCTTCCATAGACACTTACAGCACAGAAATGGCCATCTTTTC

AATGGGCGTGGTAATCCTCCTGGCCCCTGTCTCCCTGATTCTTGGTTCTTATTG

GAATATTATCTCCACTGTTATCCAGATGCAGTCTGGGGAAGGGAGACTCAAGG

CTTTTTCCACCTGTGGCTCCCATCTTATTGTTGTTGTCCTCTTCTATGGGTCAG

GAATATTCACCTACATGCGACCAAACTCCAAGACTACAAAAGAACTGGATAAAA

TGATATCTGTGTTCTATACAGCGGTGACTCCAATGTTGAACCCCATAATTTATAG

CTTGAGGAACAAAGATGTCAAAGGGGCTCTCAGGAAACTAGTTGGGAGAAAGT

GCTTCTCTCATAGGCAGTGA

OR11.22.02 (AOLFR108) (Amino Acid Sequence)
MCSFFLCQTGKQAKISMGEENQTFVSKFIFLGLSQDLQTQILLFILFLIIYLLTVLGNQ     SEQ ID NO:24

LIIILIFLDSRLHTPMYFFLRNLSFADLCFSTSIVPQVLVHFLVKRKTISFYGCMTQIIVF

LLVGCTECALLAVMSYDRYVAVCKPLYYSTIMTQRVCLWLSFRSWASGALVSLVD

TSFTFHLPYWGQNIINHYFCEPPALLKLASIDTYSTEMAIFSMGVVILLAPVSLILGSY

WNIISTVIQMQSGEGRLKAFSTCGSHLIVVVLFYGSGIFTYMRPNSKTTKELDKMIS

VFYTAVTPMLNPIIYSLRNKDVKGALRKLVGRKCRSHRQ

OR11.49.11 (AOLFR058) (DNA Sequence)
ATGGAGCTCTGGAACTTCACCTTGGGAAGTGGCTTCATTTTGGTGGGGATTCT          SEQ ID NO:25

GAATGACAGTGGGTCTCCTGAACTGCTCTGTGCTACAATTACAATCCTATACTT

GTTGGCCCTGATCAGCAATGGCCTACTGCTCCTGGCTATCACCATGGAAGCCC

GGCTCCACATGCCCATGTACCTCCTGCTTGGGCAGCTCTCTCTCATGGACCTC

CTGTTCACATCTGTTGTCACTCGCAAGGCCCTTGCGGACTTTCTGCGCAGAGA

AAACACCATCTCCTTTGGAGGCTGTGCCCTTCAGATGTTCCTGGCACTGACAAT

GGGTGGTGCTGAGGACCTCCTACTGGCCTTCATGGCCTATGACAGGTATGTGG

CCATTTGTCATCCTCTGACATACATGACCCTCATGAGCTCAAGAGCCTGCTGGC
```

-continued

```
TCATGGTGGCCACGTCCTGGATCCTGGCATCCCTAAGTGCCCTAATATATACC

GTGTATACCATGCACTATCCCTTCTGGAGGGCCCAGGAGATCAGGCATCTTCT

CTGTGAGATCCCACACTTGCTGAAGGTGGCCTGTGGTGATAGGTCCAGATATG

AGCTCATGGTATATGTGATGGGTGTGACCTTCCTGATTCCCTCTCTTGCTGCTA

TACTGGCCTCCTATACACAAATTCTACTCACTGTGCTCCATATGCCATCAAATG

AGGGGAGGAAGAAAGCCCTTGTCACCTGCTCTTCCCACCTGACTGTGGTTGG

GATGTTCTATGGAGCTGCCACATTCATGTATGTCTTGCCCAGTTCCTTCCACAG

CACCAGACAAGACAACATCATCTCTGTTTTCTACACAATTGTCACTCCAGCCCT

GAATCCACTCATCTACAGCCTGAGGAATAAGGAGGTCATGCGGGCCTTGAGGA

GGGTCCTGGGAAAATACATGCTGCCAGCACACTCCACGCTCTAG
```

OR11.49.11 (AOLFR058) (Amino Acid Sequence)
MELWNFTLGSGILVGILNDSGSPELLCATITILYLLALISNGLLLLAITMEARLHMPM    SEQ ID NO:26

YLLLGQLSLMDLLFTSVVTPKALADFLRRENTISFGGCALQMFLALTMGGAEDLLLA

FMAYDRYVAICHPLTYMTLMSSRACWLMVATSWILASLSALIYTVYTHMHYPFCRAQ

EIRHLLCEIPHLLKVACADTSRYELMVYVMGVTFLIPSLAAILASYTQILLTVLHMPSN

EGRKKALVTCSSHLTVVGMFYGAATFMYVLPSSFHSTRQDNIISVFYTIVTPALNPLI

YSLRNKEVMRALRRVLGKYMLPAHSTL

OR11.49.10 (AOLFR022) (DNA Sequence)
ATGAGACANNNNAACAATATNACAGAATTTGTCCTCCTGGGCTTTTCTCAGGAT    SEQ ID NO:27

CCTGGTGTGNNNAAAGCATTATTTGTCATGTTTTTACTCACATACNNNNNNACA

GTGGTGGGGAACCTGCTCATTGTNGTGGATATTATTGCCAGCCCTTNNTTGGG

TTCCCCAATGTATTTCTTCCTTGCCTGCCTGTCATTTATAGATGCTGCATATTCC

ACTACCATTTCTCCCAAGTTAATTGTAGGCTTATTCTGTGATAAAAAGACTATTT

CCTTCCAAGGTTGCATGGGCCAGCTATTTATAGACCATTTCTTTGGTGGGCTG

AGGTCTTCCTTCTGGTGGTGATGGCCTGTGATCGCTATGTGGCCATCTGTAAG

CCACTGCACTATTTGACCATCATGAATCGACAGGTTTGCTTCCTTCTGTTGGTN

NTNNCCATGATTGGAGGTTTTGTACATTCTGCGTTTCAAATTGTTGTGTACAGT

CTCCCTTTCTGTGGTCCCNATGTCATTGTTCATTTCAGTTGTGACATGCACCCA

TTACTGGAACTGGCATGCACTGACACCTACTTTATAGGCCTCACTGTTGTTGTC

AATAGTGGAGCAATCTGTATGGTCATTTTCAACCTTCTGTTAATCTCCTATGGAG

TCATCCTAAGCTCCCTTAAAACTTACAGTCAGGAAAAGAGGGGTAAAGCCTTGT

CTACCTGCAGCTCCGGCAGTACCGTTGTTGTCCTCTTTTTTGTACCCTGTATTT

TCATATATGTTAGACCTGTTTCAAACTTTCCTACTGATAAGTTCATGACTGTGTT

TTATACCATTATCACACACATGCTGAGTCCTTTAATATATACGTTGAGAAATTCA

GAGATGAGAAATGCTATAGAAAAACTCTTGGGTAAAAAGTTAACTATATTTATTA

TAGGAGGAGTGTCCGTCCTCATGTAG

OR11.49.10 (AOLFR022) (Amino Acid Sequence)
MRXXNNXTEFVLLGFSQDPGVXKALFVMFLLTYXXTVVGNLLIVVDIIASPXLGSPM    SEQ ID NO:28

YFFLACLSFIDAAYSTTISPKLIVGLFCDKKTISFQGCMGQLFIDHFFGGAEVFLLVV

MACDRYVAICKPLHYLTIMNRQVCFLLLVXXMIGGFVHSAFQIVVYSLPFCGPXVIV

HFSCDMHPLLELACTDTYFIGLTVVVNSGAICMVIFNLLLISYGVILSSLKTYSQEKR

-continued
GKALSTCSSGSTVVVLFFVPCIFIYVRPVSNFPTDKFMTVFYTIITHMLSPLIYTLRNS

EMRNAIEKLLGKKLTIFIIGGVSVLM

OR11.39.06 (AOLFR074) (DNA Sequence)
ATGGAACAACACAATCTAACAACGGTGAATGAATTCATTCTTACGGGAATCACA    SEQ ID NO:29

GATATCGCTGAGCTGCAGGCACCATTATTTGCATTGTTCCTCATGATCTATGTG

ATCTCAGTGATGGGCAATTTGGGCATGATTGTCCTCACCAAGTTGGACTCCAG

GTTGCAAACCCCTATGTACTTTTTTCTCAGACATCTGGCTTTCATGGATCTTGGT

TATTCAACAACTGTGGGACCCAAAATGTTAGTAAATTTTGTTGTGGATAAGAATA

TAATTTCTTATTATTTTTGTGCAACACAGCTAGCTTTCTTTCTTGTGTTCATTGGT

AGTGAACTTTTTATTCTCTCAGCCATGTCCTACGACCTCTATGTGGCCATCTGT

AACCCTCTGCTATACACAGTAATCATGTCACGAAGGGTATGTCAGGTGCTGGT

AGCAATCCCTTACCTCTATTGCACATTCATTTCTCTTCTAGTCACCATAAAGATT

TTTACTTTATCCTTCTGTGGCTACAACGTCATTAGTCATTTCTACTGTGACAGTC

TCCCTTTGTTACCTTTGCTTTGTTCAAATACACATGAAATTGAATTGATAATTCTG

ATCTTTGCAGCTATTGATTTGATTTCATCTCTTCTGATAGTTCTTTTATCTTACCT

GCTCATCCTTGTAGCCATTCTCAGGATGAATTCTGCTGGCAGACAAAAGGCTTT

TTCTACCTGTGGAGCCCACCTGACAGTGGTCATAGTGTTCTATGGGACTTTGCT

TTTCATGTACGTGCAGCCCAAGTCCAGTCATTCCTTTGACAGTGATAAAGTGGC

TTCCATATTTTACACCCTGGTTATCCCCATGTTGAATCCCTTGATCTATAGTTTA

CGAAACAAAGATGTAAAATATGCCCTACGAAGGACATGGAATAACTTATGTAAT

ATTTTTGTTTAA

OR11.39.06 (AOLFR074) (Amino Acid Sequence)
MEQHNLTTVNEFILTGITDIAELQAPLFALFLMIYVISVMGNLGMIVLTKLDSRLQTPM    SEQ ID NO:30

YFFLRHLAFMDLGYSTTVGPKMLVNFVVDKNIISYYFCATQLAFFLVFIGSELFILSA

MSYDLYVAICNPLLYTVIMSRRVCQVLVAIPYLYCTFISLLVTIKIFTLSFCGYNVISHF

YCDSLPLLPLLCSNTHEIELIILIFAAIDLISSLLIVLLSYLLILVAILRMNSAGRQKAFST

CGAHLTVVIVFYGTLLFMYVQPKSSHSFDTDKVASIFYTLVIPMLNPLIYSLRNKDVK

YALRRTWNNLCNIFV

Thus, the invention provides a set of mammalian ORs that respond to IVA, particularly murine and human IVA ORs and the use thereof for screening of modulators of IVA ORS, e.g. activators, inhibitors, stimulators, enhancers, agonists, inverse agonists and antagonists of the IVA ORs of the invention, or fragments or variants thereof. Such modulators are envisioned to be especially useful as anti-odorants. These screening methods can be used to identify high affinity agonists and antagonists of IVA olfactory receptors.

Thus, the invention provides assays for IVA olfactory modulation, where the ORs, or fragments or variants thereof, of the invention act as direct or indirect reporter molecules for the effect of modulators on olfactory transduction by IVA. The ORs, or fragments or variants thereof, can be used in assays, e.g., to measure changes in ion concentration, membrane potential, current flow, ion flux, transcription, signal transduction, receptor-ligand interaction, second messenger concentrations, in vitro, in vivo and ex vivo. In one embodiment, the IVA ORs, or fragments or variants thereof, can be used as an indirect reporters via attachment to second reporter molecules, such as green fluorescent protein (see, e.g., Mistili et al., Nature Biotech., 15:961–64 (1997)). In another embodiment, the ORs, or fragments or variants thereof, can be expressed in host cells, and modulation of olfactory transduction via OR activity can be assayed by measuring changes in intracellular $Ca^{2+}$ levels.

Methods of assaying for modulators of olfactory transduction include in vitro ligand binding assays using the IVA ORs of the invention, IVA or fragments or variants thereof. More particularly, such assays can use the ORs; portions thereof such as the extracellular or transmembrane domains; chimeric proteins comprising one or more of such domains; oocyte receptor expression; tissue culture cell receptor expression; transcriptional activation of the receptor; G protein binding to the receptor; ligand binding assays; voltage, membrane potential and conductance changes; ion flux assays; changes in intracellular second messengers such as cAMP and inositol triphosphate; changes in intracellular $Ca^{2+}$ levels; and neurotransmitter release.

The invention also provides for methods of detecting IVA olfactory nucleic acid and protein expression, allowing for the investigation of IVA olfactory receptor transduction regulation and specific identification of IVA olfactory receptor expressing cells. The IVA ORs, fragments, and variants of the invention can also be used to generate monoclonal and polyclonal antibodies useful for identifying IVA olfactory receptor expressing cells. IVA olfactory receptor expressing cells can be identified using techniques such as reverse transcription and PCR amplification of total RNA or poly $(A)^+$ RNA, northern blotting, dot blotting, in situ hybridization, RNase protection, S1 digestion, probing DNA microchip arrays, western blots, and the like.

Identification and Characterization of IVA Olfactory Receptors

The amino acid sequences of the IVA ORs and polypeptides of the invention can be identified by putative translation of the IVA coding nucleic acid sequences. These various amino acid sequences and the coding nucleic acid sequences may be compared to one another or to other sequences according to a number of methods.

For example, in sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, as described below for the BLASTN and BLASTP programs, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of: from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *PNAS*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of an algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J Mol. Biol.* 215:403–410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., Altschul et al., *Nuc. Acids Res.* 25:3389–3402 (1977) and Altschul et al., *J Mol. Biol.* 215:403–410 (1990)). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, PNAS, 89:10915 (1989)) alignments (B) of 50, expectation (E) of 10, M=5, N=-4, and a comparison of both strands.

Another example of a useful algorithm is PILEUP. PILEUP creates a multiple sequence alignment from a group of related sequences using progressive, pairwise alignments to show relationship and percent sequence identity. It also plots a so-called "tree" or "dendogram" showing the clustering relationships used to create the alignment (see, e.g., FIG. 2). PILEUP uses a simplification of the progressive alignment method of Feng & Doolittle, *J Mol. Evol.* 35:351–60 (1987). The method used is similar to the method described by Higgins & Sharp, CABIOS 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984) encoded by the genes were derived by conceptual translation of the corresponding open reading frames. Comparison of these protein sequences to all known proteins in the public sequence databases using BLASTP algorithm revealed their strong homology to the members of the mammalian olfactory receptor family, each of the odorant receptor sequences having at least 50%, and preferably at least 55%, at least 60%, at least 65%, and most preferably at least 70%, amino acid identity to at least one known member of the family.

The nucleic acid molecules of the present invention are typically intronless and encode putative IVA OR proteins generally having lengths of approximately 290 to approximately 400 amino acid residues that contain seven transmembrane domains, as predicted by hydrophobicity plotting analysis, indicating that they belong to the G protein-coupled receptor 7-transmembrane (7TM) superfamily, which includes the subset of taste and olfactory receptors. In addition to the overall structural similarity, each of the IVA ORs identified herein has a characteristic sequence signature of an olfactory receptor. In particular, all the identified sequences contain very close matches to the following consensus amino acid motifs (Mombaerts, 1999, Pilpel 1999): EFILL (SEQ ID NO:45) before transmembrane domain 1, LHTPMY (SEQ ID NO:46) in intracellular loop 1, MAYDRYVAIC (SEQ ID NO:47) at the end of transmembrane domain 3 and the beginning of intracellular loop 2, SY at the end of transmembrane domain 5, FSTCSSH (SEQ ID NO:48) in the beginning of transmembrane domain 6, and PMLNPF (SEQ ID NO:49) in transmembrane domain 7. Combination of all the above-mentioned structural features of the identified genes and encoded proteins strongly suggests that they represent novel members of the human olfactory receptor family.

Definitions

As used herein, the following terms have the meanings ascribed to them unless specified otherwise.

"OR" refers to one or more members of a family of G protein-coupled receptors that are expressed in olfactory cells. Olfactory receptor cells can also be identified on the basis of morphology (see, e.g., Roper, supra), or by the expression of proteins specifically expressed in olfactory cells. OR family members may have the ability to act as receptors for olfactory transduction.

"IVA OR" refers to a member of the family of G protein-coupled receptors that is expressed in an olfactory cell, which receptors bind and/or are activated by isovaleric acid (IVA) in a binding or activity assay for identifying ligands that bind and/or activate GPCRs. Such assays are described infra. IVA receptors herein will include fragments, variants, including synthetic and naturally occurring, and chimeras that respond to or bind IVA.

"OR" nucleic acids encode a family of GPCRs with seven transmembrane regions that have "G protein-coupled receptor activity," e.g., they may bind to G proteins in response to extracellular stimuli and promote production of second messengers such as IP3, cAMP, cGMP, and $Ca^{2+}$ via stimulation of enzymes such as phospholipase C and adenylate cyclase.

Topologically, certain chemosensory GPCRs have an "N-terminal domain;" "extracellular domains;" "transmembrane domains" comprising seven transmembrane regions, and corresponding cytoplasmic, and extracellular loops; "cytoplasmic domains," and a "C-terminal domain" (see, e.g., Hoon et al., Cell, 96:541–51 (1999); Buck & Axel, Cell, 65:175–87 (1991)). These domains can be structurally identified using methods known to those of skill in the art, such as sequence analysis programs that identify hydrophobic and hydrophilic domains (see, e.g., Stryer, Biochemistry, (3rd ed. 1988); see also any of a number of Internet based sequence analysis programs, such as those found at dot.imgen.bcm.tmc.edu). Such domains are useful for making chimeric proteins and for in vitro assays of the invention, e.g., ligand binding assays.

"Extracellular domains" therefore refers to the domains of OR polypeptides that protrude from the cellular membrane and are exposed to the extracellular face of the cell. Such domains generally include the "N terminal domain" that is exposed to the extracellular face of the cell, and optionally can include portions of the extracellular loops of the transmembrane domain that are exposed to the extracellular face of the cell, i.e., the loops between transmembrane regions 2 and 3, between transmembrane regions 4 and 5, and between transmembrane regions 6 and 7.

The "N terminal domain" region starts at the N-terminus and extends to a region close to the start of the first transmembrane region. "Transmembrane domain," which comprises the seven "transmembrane regions," refers to the domain of OR polypeptides that lies within the plasma membrane, and may also include the corresponding cytoplasmic (intracellular) and extracellular loops. The seven transmembrane regions and extracellular and cytoplasmic loops can be identified using standard methods, as described in Kyte & Doolittle, J. Mol. Biol., 157:105–32 (1982), or in Stryer, supra. The general secondary and tertiary structure of transmembrane domains, in particular the seven transmembrane domains of G protein-coupled receptors such as olfactory receptors, are known in the art. Thus, primary structure sequence can be designed or predicted based on known-transmembrane domain sequences, as described in detail below. These transmembrane domains are useful for in vitro ligand-binding assays, both soluble and solid phase.

"Cytoplasmic domains" refers to the domains of OR polypeptides that face the inside of the cell, e.g., the "C terminal domain" and the intracellular loops of the transmembrane domain, e.g., the intracellular loop between transmembrane regions 1 and 2, the intracellular loop between transmembrane regions 3 and 4, and the intracellular loop between transmembrane regions 5 and 6. "C terminal domain" refers to the region that spans the end of the last transmembrane domain and the C-terminus of the protein, and which is normally located within the cytoplasm.

The term "ligand-binding region" or "ligand-binding domain" refers to sequences derived from a chemosensory receptor, particularly an olfactory receptor, that substantially incorporates at least transmembrane domains II to VII. The ligand-binding region may be capable of binding a ligand, and more particularly, an odorant.

The phrase "functional effects" in the context of assays for testing compounds that modulate OR family member mediated olfactory transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" in the context of assays is meant assays for a compound that increases or decreases a parameter that is indirectly or directly under the influence of an OR family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte OR gene expression; tissue culture cell OR expression; transcriptional activation of OR genes; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of OR genes or proteins are used interchangeably to refer to inhibitory, activating, or modulating molecules identified using in vitro and in vivo assays for olfactory transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate olfactory transduction, e.g., antagonists. Activators are compounds that, e.g., bind to, stimulate, increase, open, activate, facilitate, enhance activation, sensitize, or up regulate olfactory transduction, e.g., agonists. Modulators include compounds that, e.g., alter the interaction of a receptor with: extracellular proteins that bind activators or inhibitor (e.g., odorant-binding proteins, ebnerin and other members of the hydrophobic carrier family); G proteins; kinases (e.g., homologs of rhodopsin kinase and beta adrenergic receptor kinases that are involved in deactivation and desensitization of a receptor); and arrestins, which also deactivate and desensitize receptors. Modulators can include genetically modified versions of OR family members, e.g., with altered activity, as well as naturally occurring and synthetic ligands, antagonists, agonists, small chemical molecules and the like. Such assays for inhibitors and activators include, e.g., expressing OR family members in cells or cell membranes, applying putative modulator compounds, in the presence or absence of tastants, e.g., sweet tastants, and then determining the functional effects on olfactory transduction, as described above. Samples or assays comprising OR family members that are treated with a potential activator, inhibitor, or modulator are compared to control samples without the inhibitor, activator, or modulator to examine the extent of modulation. Control samples (untreated with modulators) are assigned a relative OR activity value of 100%. Inhibition of a OR is achieved when the OR activity value relative to the control is about 80%, optionally 50% or 25–0%. Activation of an OR is achieved when the OR activity value relative to the control is 110%, optionally 150%, optionally 200–500%, or 1000–3000% higher.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated" "isolated," when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific degenerate oligonucleotide primer pairs) for amplifying (e.g., by polymerase chain reaction, PCR) naturally expressed (e.g., genomic or mRNA) or recombinant (e.g., cDNA) nucleic acids of the invention in vivo or in vitro.

The term "7-transmembrane receptor" means a polypeptide belonging to a superfamily of transmembrane proteins that have seven domains that span the plasma membrane seven times (thus, the seven domains are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "library" means a preparation that is a mixture of different nucleic acid or polypeptide molecules, such as the library of recombinantly generated chemosensory, particularly olfactory receptor ligand-binding domains generated by amplification of nucleic acid with degenerate primer pairs, or an isolated collection of vectors that incorporate the amplified ligand-binding domains, or a mixture of cells each randomly transfected with at least one vector encoding an olfactory receptor, i.e. an IVA OR according to the invention.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones (see e.g., *Oligonucleotides and Analogues, a Practical Approach*, ed. F. Eckstein, Oxford Univ. Press (1991); Antisense Strategies, *Annals of the N.Y. Acad. of Sci.*, Vol. 600, Eds. Baserga et al. (NYAS 1992); Milligan *J. Med. Chem.* 36:1923–1937 (1993); *Antisense Research and Applications* (1993, CRC Press), WO 97/03211; WO 96/39154; Mata, *Toxicol. Appl. Pharmacol.* 144:189–197 (1997); Strauss-Soukup, *Biochemistry* 36:8692–8698 (1997); Samstag, *Antisense Nucleic Acid Drug Dev,* 6:153–156 (1996)).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., *Nucleic Acid Res.*, 19:5081 (1991); Ohtsuka et al., *J. Biol. Chem.*, 260:2605–08 (1985); Rossolini et al., *Mol. Cell. Probes*, 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "plasma membrane translocation domain" or simply "translocation domain" means a polypeptide domain that, when incorporated into the amino terminus of a polypeptide coding sequence, can with great efficiency "chaperone" or "translocate" the hybrid ("fusion") protein to the cell plasma membrane. For instance, a "translocation domain" may be derived from the amino terminus of the bovine rhodopsin receptor polypeptide. In one embodiment, the translocation domain may be functionally equivalent to an exemplary translocation domain (5'-MNGTEGPN-FYVPFSNKTGW) (SEQ ID NO:50). However, rhodopsin from any mammal may be used, as can other translocation facilitating sequences. Thus, the translocation domain is particularly efficient in translocating 7-transmembrane fusion proteins to the plasma membrane, and a protein (e.g., an olfactory receptor polypeptide) comprising an amino terminal translocating domain will be transported to the plasma membrane more efficiently than without the domain. However, if the N-terminal domain of the polypeptide is active in binding, the use of other translocation domains may be preferred.

"Functional equivalency" means the domain's ability and efficiency in translocating newly translated proteins to the plasma membrane as efficiently as the exemplary translocation domain above under similar conditions; relatively efficiencies an be measured (in quantitative terms) and compared, as described herein. Domains falling within the scope of the invention can be determined by routine screening for their efficiency in translocating newly synthesized polypeptides to the plasma membrane in a cell (mammalian, Xenopus, and the like) with the same efficiency as the twenty amino acid long translocation domain supra, as described in detail below.

The "translocation domain," "ligand-binding domain", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gin or his; asp/glu; cys/ser; gln/asn; gly/asp; gly/ala or pro; his/asn or gin; ile/leu or val; leu/ile or val; lys/arg or gin or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (O); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, *Proteins*, W. H. Freeman and Company (1984); Schultz and Schimer, *Principles of Protein Structure*, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding domains, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered.

Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$), thiazole, retroamide, thioamide, or ester (see, e.g., Spatola, *Chemistry and Biochemistry of Amino Acids, Peptides and Proteins*, 7:267–357, "Peptide Backbone Modifications," Marcell Dekker, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The phrase "selectively (or specifically) hybridizes to" refers to the binding, duplexing, or hybridizing of a molecule only to a particular nucleotide sequence under stringent hybridization conditions when that sequence is present in a complex mixture (e g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0

M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides that they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-OR" antibody is an antibody or antibody fragment that specifically binds a polypeptide encoded by a OR gene, cDNA, or a subsequence thereof, i.e. an IVA OR according to the invention.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to an IVA OR subgenus member from specific species such as rat, mouse, or human can be selected to obtain only those polyclonal antibodies that are specifically immunoreactive with the IVA OR polypeptide or an immunogenic portion thereof and not with other proteins, except for orthologs or polymorphic variants and alleles of the IVA OR polypeptide. This selection may be achieved by subtracting out antibodies that cross-react with IVA OR molecules from other species or other IVA OR molecules. Antibodies can also be selected that recognize only IVA OR GPCRs but not other GPCRs. A variety of immunoassay formats may be used to select antibodies specifically immunoreactive with a particular IVA protein. For example, solid-phase ELISA immunoassays are routinely used to select antibodies specifically immunoreactive with a protein (see, e.g., Harlow & Lane, *Antibodies, A Laboratory Manual*, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa, HEK-293, and the like, e.g., cultured cells, explants, and cells in vivo.

Isolation and Expression of IVA Olfactory Receptors

Isolation and expression of the IVA ORs, or fragments or variants thereof, of the invention can be performed as described below. PCR primers can be used for the amplification of nucleic acids encoding olfactory receptor ligand-binding regions and libraries of these nucleic acids can thereby be generated. Libraries of expression vectors can then be used to infect or transfect host cells for the functional expression of these libraries. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

The nucleic acid sequences of the invention and other nucleic acids used to practice this invention, whether RNA, cDNA, genomic DNA, vectors, viruses or hybrids thereof, may be isolated from a variety of sources, genetically engineered, amplified, and/or expressed recombinantly. Any recombinant expression system can be used, including, in addition to mammalian cells, e.g., bacterial, yeast, insect or plant systems.

Alternatively, these nucleic acids can be synthesized in vitro by well-known chemical synthesis techniques, as described in, e.g., Carruthers, *Cold Spring Harbor Symp. Quant. Biol.* 47:411–418 (1982); Adams, *Am. Chem. Soc.* 105:661 (1983); Belousov, *Nucleic Acids Res.* 25:3440–3444 (1997); Frenkel, *Free Radic. Biol. Med.* 19:373–380 (1995); Blommers, *Biochemistry* 33:7886–7896 (1994); Narang, *Meth. Enzymol.* 68:90 (1979); Brown, *Meth. Enzymol.* 68:109 (1979); Beaucage, *Tetra. Lett.* 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., Molecular Cloning: a Laboratory manual (2nd ed.), Vols. 1–3, Cold Spring Harbor Laboratory (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I, Theory and Nucleic Acid Preparation, Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers are used to amplify nucleic acid encoding an olfactory receptor ligand-binding region. The nucleic acids described herein can also be cloned or measured quantitatively using amplification techniques. Using exemplary degenerate primer pair sequences, (see below), the skilled artisan can select and design suitable oligonucleotide amplification primers. Amplification methods are also well known in the art, and include, e.g., polymerase chain reaction, PCR (PCR Protocols, a Guide to Methods and Applications, ed. Innis. Academic Press, N.Y. (1990) and PCR Strategies, ed. Innis, Academic Press, Inc., N.Y. (1995), ligase chain reaction (LCR) (see, e.g., Wu, *Genomics* 4:560 (1989); Landegren, *Science* 241:1077,(1988); Barringer, *Gene* 89:117 (1990)); transcription amplification (see, e.g., Kwoh, *PNAS*, 86:1173 (1989)); and, self-sustained sequence replication (see, e.g., Guatelli, *PNAS,* 87:1874 (1990)); Q Beta replicase amplification (see, e.g., Smith, *J. Clin. Microbiol.* 35:1477–1491 (1997)); automated Q-beta replicase amplification assay (see, e.g., Burg, *Mol. Cell. Probes* 10:257–271 (1996)) and other RNA polymerase mediated techniques (e.g., NASBA, Cangene, Mississauga, Ontario); see also Berger, *Methods Enzymol.* 152:307–316 (1987); Sambrook; Ausubel; U.S. Pat. Nos. 4,683,195 and 4,683,202; Sooknanan, *Biotechnology* 13:563–564 (1995).

Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. For example, Pst I and Bsp E1 sites were designed into the exemplary primer pairs of the invention. These particular restriction sites have a sequence that, when ligated, are "in-frame" with respect to the 7-membrane receptor "donor" coding sequence into which they are spliced (the ligand-binding region coding sequence is internal to the 7-membrane polypeptide, thus, if it is desired that the construct be translated downstream of a restriction enzyme splice site, out of frame results should be avoided; this may not be necessary if the inserted ligand-binding domain comprises substantially most of the transmembrane VII region). The primers can be designed to retain the original sequence of the "donor" 7-membrane receptor (the Pst I and Bsp E1 sequence in he primers of the invention generate an insert that, when ligated into the Pst I/Bsp E1 cut vector, encode residues found in the "donor" mouse olfactory receptor M4 sequence). Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

The primer pairs are designed to selectively amplify ligand-binding regions of IVA olfactory receptor proteins. These domain regions may vary for different IVA ORs. Thus, domain regions of different sizes comprising different domain structures may be amplified; for example, transmembrane (TM) domains II through VII, III through VII, III through VI or II through VI, or variations thereof (e.g., only a subsequence of a particular domain, mixing the order of the domains, and the like), of a 7-transmembrane OR.

As domain structures and sequence of many 7-membrane proteins, particularly olfactory receptors, are known, the skilled artisan can readily select domain-flanking and internal domain sequences as model sequences to design degenerate amplification primer pairs. For example, a nucleic acid sequence encoding domain regions II through VII can be generated by PCR amplification using a primer pair. To amplify a nucleic acid comprising transmembrane domain I (TM I) sequence, a degenerate primer can be designed from a nucleic acid that encodes the amino acid sequence E/DFILLG (SEQ ID NO: 51). Such a degenerate primer can be used to generate a binding domain incorporating TM I through TM III, TM I through TM IV, TM I through TM V, TM I through TM VI or TM I through TM VII).

To amplify a nucleic acid comprising a transmembrane domain II (TM III) sequence, a degenerate primer (of at least about 17 residues) can be designed from a nucleic acid that encodes the amino acid sequence M(A/G)(Y/F)DRYVAI 3' (SEQ ID NO: 52) (encoded by a nucleic acid sequence such as 5'-ATGG(G/C)CT(A/T)TGACCG(C/A/T)T(AT)(C/T)GT-3' (SEQ ID NO: 53))). The primers can be designed to retain the original sequence of the "donor" 7-membrane receptor (the Pst I and Bsp E1 sequence in he primers of the invention generate an insert that, when ligated into the Pst I/Bsp E1 cut vector, encode residues found in the "donor" mouse olfactory receptor M4 sequence). Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

The primer pairs are designed to selectively amplify ligand-binding regions of IVA olfactory receptor proteins. These domain regions may vary for different IVA ORs. Thus, domain regions of different sizes comprising different domain structures may be amplified; for example, transmembrane (TM) domains II through VII, III through VII, III through VI or II through VI, or variations thereof (e.g., only a subsequence of a particular domain, mixing the order of the domains, and the like), of a 7-transmembrane OR.

olfactory receptor ligand-binding regions (see, e.g., Rose, *Nucleic Acids Res.* 26:1628-1635 (1998); Singh, *Biotechniques,* 24:318-19 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, *Nucleic Acids Res.* 25:4866-4871 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, *Nat. Struct. Biol.* 5:950-954 (1998)). For example, two degenerate bases can be the pyrimidine base 6H, 8H-3,4-dihydropyrimido[4, 5-c][1,2]oxazin-7-one or the purine base N6-methoxy-2,6-diaminopurine (see, e.g., Hill, *PNAS,* 95:4258-63 (1998)). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramidite (the term "P" in the sequences, see above). This pyrimidine analog hydrogen bonds with purines, including A and G residues.

Exemplary primer pairs for amplification of olfactory receptor transmembrane domains II through VII include:

```
(a)  5'-GGGGTCCGGAG(A/G)(C/G)(A/G)TA(A/G/T)AT(A/G/P)A(A/G/P)(A/G/P)GG-3'; and          (SEQ ID NO:56)
     5'-GGGGCTGCAGACACC(A/C/G/T)ATGTA(C/T)(C/T)T(A/C/G/T)TT(C/T)(C/T)T-3';             (SEQ ID NO:57)

(b)  5'-GGGGTCCGGAG(A/G)(C/G)T(A/G)A(A/G/T)AT(A/G/P)A(A/G/P)(A/G/P)GG-3'; and          (SEQ ID NO:58)
     5'-GGGGCTGCAGACACC(AC/G/T)ATGTA(C/T)(C/T)T(A/C/G/T)TT(C/T)(C/T)T-3';              (SEQ ID NO:59)

(c)  5'-GGGGTCCGGAG(A/G)(C/G)T(A/G)A(A/G/T)AT(A/G/C/T)A(A/G/C/T)(A/G/C/T)GG-3'; and    (SEQ ID NO:60)
     5'-GGGGCTGCAGACACC(A/C/G/T)ATGTA(C/T)(C/T)T(A/C/G/T)TT(C/T)(C/T)T-3';             (SEQ ID NO:61)

(d)  primer TM7I   5'-AT(G/A)AAIGG(G/A)TTIA(G/A)CATIGG;                                 (SEQ ID NO:62)

(e)  primer TM3D   5'-ATGGCITA(C/T)GA(C/T)(A/C)GOTA(C/T)GTIGC;                          (SEQ ID NO:63)

(f)  primer 213    5'-CGGATCCGCITA(C/G)GA(C/T)GCITA(C/T)GTIGC(A/C/G/T)AT(A/C/T)TG;      (SEQ ID NO:64)

(g)  primer 214    5'-CCTGCAG(A/G)TA(A/G/T)AT(A/G)AAIGG(A/G)TTIA(A/G)CAT(A/C/G/T)GG; and (SEQ ID NO:65)

(h)  primer P41    5'-AA(A/G)(G/T)CITT(C/G/T)(A/C)IACITG(C/T)G(C/G)ITCICA,              (SEQ ID NO:66)
``` where I represents 2'-deoxyinosine, and O represents 2'-deoxycytidine phosphorothioate.

To amplify transmembrane domain VI (TM VI) sequence, a degenerate primer (of at least about 17 residues) can be designed from nucleic acid encoding an amino acid sequence TC(G/A)SHL (SEQ ID NO:54), encoded by a sequence such as 5'-AG(G/A)TGN(G/C)(T/A)N(G/C)C (G/A)CANGT-3') 3' (SEQ ID NO:55). Such a degenerate primer can be used to generate a binding domain incorporating TM I through TM VI, TM II through TM VI, TM III through TM VI or TM IV through TM VI).

Paradigms to design degenerate primer pairs are well known in the art. For example, a COnsensus-DEgenerate Hybrid Oligonucleotide Primer (CODEHOP) strategy computer program is accessible as http://blocks.fhcrc.org/codehop.html, and is directly linked from the BlockMaker multiple sequence alignment site for hybrid primer prediction beginning with a set of related protein sequences, as known Nucleic acids that encode ligand-binding regions of IVA olfactory receptors may be generated by amplification (e.g., PCR) of appropriate nucleic acid sequences using degenerate primer pairs. The amplified nucleic acid can be genomic DNA from any cell or tissue or mRNA or cDNA derived from olfactory receptor-expressing cells, e.g., olfactory neurons or olfactory epithelium.

Isolation from olfactory receptor-expressing cells is well known in the art (cells expressing naturally or inducibly expressing olfactory receptors can be used to express the hybrid olfactory receptors of the invention to screen for potential odorants and odorant effect on cell physiology, as described below). For example, cells can be identified by olfactory marker protein (OMP), an abundant cytoplasmic protein expressed almost exclusively in mature olfactory sensory neurons (see, e.g., Buiakova, *PNAS,* 93:9858–63 (1996)). Shirley, *Eur. J. Biochem.* 32:485–494 (1983), describes a rat olfactory preparation suitable for biochemical studies in vitro on olfactory mechanisms. Cultures of adult rat olfactory receptor neurons are described by Vargas, *Chem. Senses* 24:211–216 (1999). Because these cultured neurons exhibit typical voltage-gated currents and are responsive to application of odorants, they can also be used to express the hybrid olfactory receptors of the invention for odorant screening (endogenous olfactory receptor can be initially blocked, if desired, by, e.g., antisense, knockout, and the like). U.S. Pat. No. 5,869,266 describes culturing human olfactory neurons for neurotoxicity tests and screening. Murrell, *J. Neurosci.* 19:8260–8270 (1999), describes differentiated olfactory receptor-expressing cells in culture that respond to odorants, as measured by an influx of calcium.

In one embodiment, hybrid protein-coding sequences comprising nucleic acids ORs fused to the translocation sequences described herein may be constructed. Also provided are hybrid ORs comprising the translocation motifs and ligand-binding domains of olfactory receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, transgenics, and a promoter fragment can be employed to direct expression of the desired nucleic acid in all tissues. Olfactory cell-specific transcriptional elements can also be used to express the fusion polypeptide receptor, including, e.g., a 6.7 kb region upstream of the M4 olfactory receptor coding region. This region was sufficient to direct expression in olfactory epithelium with wild type zonal restriction and distributed neuronal expression for endogenous olfactory receptors (Qasba, *J. Neurosci.* 18:227–236 (1998)). Receptor genes are normally expressed in a small subset of neurons throughout a zonally restricted region of the sensory epithelium. The transcriptional or translational control elements can be isolated from natural sources, obtained from such sources as ATCC or GenBank libraries, or prepared by synthetic or recombinant methods.

In another embodiment, fusion proteins, either having C-terminal or, more preferably, N-terminal translocation sequences, may also comprise the translocation motif described herein. However, these fusion proteins can also comprise additional elements for, e.g., protein detection, purification, or other applications. Detection and purification facilitating domains include, e.g., metal chelating peptides such as polyhistidine tracts or histidine-tryptophan modules or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, *Biochimie* 80:289–293 (1998)), subtilisin protease recognition motif (see, e.g., Polyak, *Protein Eng.* 10:615–619 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide-encoding nucleic acid sequence linked to six histidine residues followed by a thioredoxin, an enterokinase cleavage site (see, e.g., Williams, *Biochemistry* 34:1787–1797 (1995)), and an amino terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature (see, e.g., Kroll, *DNA Cell. Biol.* 12:441–53 (1993)).

Expression vectors, either as individual expression vectors or as libraries of expression vectors, comprising the olfactory binding domain-encoding sequences may be introduced into a genome or into the cytoplasm or a nucleus of a cell and expressed by a variety of conventional techniques, well described in the scientific and patent literature (see, e.g., Roberts, *Nature* 328:731 (1987); Berger supra; Schneider, *Protein Expr. Purif.* 6435:10 (1995); Sambrook; Tijssen; Ausubel). Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfuron or Basta) to permit selection of those cells transformed with the desired DNA sequences (see, e.g., Blondelet-Rouault, *Gene* 190:315–17 (1997); Aubrecht, *J. Pharmacol. Exp. Ther.,* 281:992–97 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a ligand-binding domain within any 7-transmembrane polypeptide. 7-transmembrane receptors belong to a superfamily of transmembrane (TM) proteins having seven domains that traverse a plasma membrane seven times. Each of the seven domains spans the plasma membrane (TM I to TM VII). Because 7-transmembrane receptor polypeptides have similar primary sequences and secondary and tertiary structures, structural domains (e.g., TM domains) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. To predict TM domains and their boundaries and topology, a "neural network algorithm" by "PHD server" can be used, as done by Pilpel, *Protein Science* 8:969–977 (1999); Rost, *Protein Sci.* 4:521–533 (1995). Periodicity detection enhancement and alpha helical periodicity index can be done as by, e.g., Donnelly, *Protein Sci.* 2:55–70 (1993). Other alignment and modeling algorithms are well known in the art, see, e.g., Peitsch, *Receptors Channels* 4:161–164 (1996); Cronet, *Protein Eng.* 6:59–64 (1993) (homology and "discover modeling"); http://bioinfo.weizmann.ac.il/.

The library sequences include receptor sequences that correspond to TM ligand-binding domains, including, e.g., TM II to VII, TM II to VI, TM III to VII, and TM III to VII, that have been amplified (e.g., PCR) from mRNA of or cDNA derived from, e.g., olfactory receptor-expressing neurons or genomic DNA.

Libraries of olfactory receptor ligand-binding TM domain sequences can include a various TM domains or variations thereof, as described above. These sequences can be derived from any 7-transmembrane receptor. Because these polypeptides have similar primary sequences and secondary and tertiary structures, the seven domains can be identified by various analyses well known in the art, including, e.g., homology modeling, Fourier analysis and helical periodicity (see, e.g., Pilpel supra), as described above. Using this information sequences flanking the seven domains can be identified and used to design degenerate primers for amplification of various combinations of TM regions and subsequences.

The present invention also includes not only the DNA and proteins having the specified amino acid sequences corresponding to IVA olfactory receptors, but also fragments thereof, particularly DNA fragments of, for example, 40, 60, 80, 100, 150, 200, or 250 nucleotides, or more, as well as protein fragments of, for example, 10, 20, 30, 50, 70, 100, or 150 amino acids, or more.

Also contemplated are chimeric proteins, comprising at least 10, 20, 30, 50, 70, 100, or 150 amino acids, or more, of one of at least one of the IVA olfactory receptors described herein, coupled to additional amino acids representing all or part of another G protein receptor, preferably a member of the 7TM superfamily. These chimeras can be made from the instant receptors and a G protein receptor described herein, or they can be made by combining two or more of the present proteins. In one preferred embodiment, one portion of the chimera corresponds to and is derived from one or more of the domains of the seven transmembrane protein described herein, and the remaining portion or portions come from another G protein-coupled receptor. Chimeric receptors are well known in the art, and the techniques for creating them and the selection and boundaries of domains or fragments of G protein-coupled receptors for incorporation therein are also well known. Thus, this knowledge of those skilled in the art can readily be used to create such chimeric receptors. The use of such chimeric receptors can provide, for example, an olfactory selectivity characteristic of one of the IVA olfactory receptors specifically disclosed herein, coupled with the signal transduction characteristics of another receptor, such as a well known receptor used in prior art assay systems.

For example, a domain such as a ligand-binding domain, an extracellular domain, a transmembrane domain (e.g., one comprising seven transmembrane regions and corresponding extracellular and cytosolic loops), the transmembrane domain and a cytoplasmic domain, an active site, a subunit association region, etc., can be covalently linked to a heterologous protein. For instance, an extracellular domain can be linked to a heterologous GPCR transmembrane domain, or a heterologous GPCR extracellular domain can be linked to a transmembrane domain. Other heterologous proteins of choice can include, e.g., green fluorescent protein, β-gal, glutamate receptor, and the rhodopsin presequence.

Polymorphic variants, alleles, and interspecies homologs that are substantially identical to an IVA olfactory receptor disclosed herein can be isolated using the nucleic acid probes described above. It is hypothesized that allelic differences in receptors may explain why there is a difference in olfactory sensation in different human subjects. Accordingly, the identification of such alleles may be significant, especially with respect to producing receptor libraries that adequately represent the olfactory capability of the human population, i.e., which take into account allelic differences in different individuals. Alternatively, expression libraries can be used to clone olfactory receptors and polymorphic variants, alleles, and interspecies homologs thereof, by detecting expressed homologs immunologically with antisera or purified antibodies made against an olfactory polypeptide, which also recognize and selectively bind to the olfactory receptor homolog.

Also within the scope of the invention are host cells for expressing the IVA ORs, fragments, chimeras or variants of the invention. To obtain high levels of expression of a cloned gene or nucleic acid, such as cDNAs encoding the IVA olfactory receptors, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. However, bacterial or eukaryotic expression systems can be used.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one gene into the host cell capable of expressing the olfactory receptor, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

Immunological Detection of IVA OR Polypeptides

In addition to the detection of IVA OR genes and gene expression using nucleic acid hybridization technology, one can also use immunoassays to detect IVA ORs, e.g., to identify olfactory receptor cells, and variants of IVA OR genus members. Immunoassays can be used to qualitatively or quantitatively analyze the IVA ORs. A general overview of the applicable technology can be found in Harlow & Lane, Antibodies: A Laboratory Manual (1988).

Antibodies to IVA OR Family Members

Methods of producing polyclonal and monoclonal antibodies that react specifically with an IVA OR family member are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature*, 256:495–97 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science*, 246:1275–81 (1989); Ward et al., *Nature*, 341:544–46 (1989)).

A number of IVA OR-comprising immunogens may be used to produce antibodies specifically reactive with an IVA OR family member. For example, a recombinant IVA OR protein, or an antigenic fragment thereof, can be isolated as described herein. Suitable antigenic regions include, e.g., the conserved motifs that are used to identify members of the OR family. Recombinant proteins can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. For example, an inbred strain of mice (e.g., BALB/C mice) or rabbits may be immunized with the protein using a standard adjuvant, such as Freund's adjuvant, and a standard immunization protocol. The animal's immune response to the immunogen preparation is monitored by taking test bleeds and determining the titer of reactivity to the OR. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen may be immortalized, commonly by fusion with a myeloma cell (see Kohler & Milstein, *Eur. J. Immunol.*, 6:511–19 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science*, 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^9$ or greater are selected and tested for their cross reactivity against non-OR proteins, or other OR family members or other related proteins from other organisms, using a competitive binding immunoassay. Specific polyclonal antisera and monoclonal antibodies will usually bind with a Kd of at least about 0.1 mM, more usually at least about 1 pM, optionally at least about 0.1 pM or better, and optionally 0.01 pM or better.

Once OR family member specific antibodies are available, individual OR proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

Immunological Binding Assays

IVA OR proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case an OR family member or an antigenic subsequence thereof). The antibody (e.g., anti-OR) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled OR polypeptide or a labeled anti-OR antibody. Alternatively, the labeling agent may be a third moiety, such a secondary antibody that specifically binds to the antibody/OR complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.*, 111:1401–1406 (1973); Akerstrom et al., *J. Immunol.*, 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting an IVA OR protein in a sample may be either competitive or noncompetitive. Non-competitive immunoassays are assays in which the amount of antigen is directly measured. In one preferred "sandwich" assay, for example, the anti-IVA OR antibodies can be bound directly to a solid substrate on which they are immobilized. These immobilized antibodies then capture the OR protein present in the test sample. The IVA OR protein is thus immobilized is then bound by a labeling agent, such as a second OR antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of IVA OR protein present in the sample is measured indirectly by measuring the amount of a known, added (exogenous) IVA OR protein displaced (competed away) from an anti-IVA OR antibody by the unknown IVA OR protein present in a sample. In one competitive assay, a known amount of IVA OR protein is added to a sample and the sample is then contacted with an antibody that specifically binds to the IVA OR. The amount of exogenous IVA OR protein bound to the antibody is inversely proportional to the concentration of IVA OR protein present in the sample. In a particularly preferred embodiment, the antibody is immobilized on a solid substrate. The amount of IVA OR protein bound to the antibody may be determined either by measuring the amount of IVA OR protein present in an IVA OR/antibody complex, or alternatively by measuring the amount of remaining uncomplexed protein. The amount of IVA OR protein may be detected by providing a labeled OR molecule.

A hapten inhibition assay is another preferred competitive assay. In this assay the known IVA OR protein is immobilized on a solid substrate. A known amount of anti-IVA OR antibody is added to the sample, and the sample is then contacted with the immobilized IVA OR. The amount of anti-IVA OR antibody bound to the known immobilized OR protein is inversely proportional to the amount of IVA OR protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for cross-reactivity determinations. For example, a protein at least partially encoded by the nucleic acid sequences disclosed herein can be immobilized to a solid support. Proteins (e.g., IVA OR proteins and homologs) are added to the assay that compete for binding of the antisera to the immobilized antigen. The ability of the added proteins to compete for binding of the antisera to the immobilized protein is compared to the ability of the IVA OR polypeptide encoded by the nucleic acid sequences disclosed herein to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs. In addition, peptides comprising amino acid sequences representing conserved motifs that are used to identify members of the OR family can be used in cross-reactivity determinations.

The immunoabsorbed and pooled antisera are then used in a competitive binding immunoassay as described above to compare a second protein, thought to be perhaps an allele or polymorphic variant of a OR family member, to the immunogen protein (i.e., IVA OR protein encoded by the nucleic acid sequences disclosed herein). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by nucleic acid sequences disclosed herein required to inhibit 50% of binding, then the second protein is said to specifically bind to the polyclonal antibodies generated to an IVA OR immunogen.

Antibodies raised against OR conserved motifs can also be used to prepare antibodies that specifically bind only to GPCRs of the OR family, but not to GPCRs from other families.

Polyclonal antibodies that specifically bind to a particular member of the IVA or subgenus disclosed herein can be make by subtracting out cross-reactive antibodies using other OR family members. Species-specific polyclonal antibodies can be made in a similar way. For example, antibodies specific to a particular human IVA OR can be made by, subtracting out antibodies that are cross-reactive with orthologous sequences, e.g., the murine counterpart.

Other Assay Formats

Western blot (immunoblot) analysis is used to detect and quantify the presence of IVA OR protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the IVA OR protein. The anti-IVA OR polypeptide antibodies specifically bind to the IVA OR polypeptide on the solid support. These antibodies may be directly labeled or alternatively may be subsequently detected using labeled antibodies (e.g., labeled sheep anti-mouse antibodies) that specifically bind to the anti-IVA OR antibodies.

Other, assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.,* 5:34-41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™)

(SEQ ID NO: 62), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a OR protein, or secondary antibodies that recognize anti-OR.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Detection of IVA Olfactory Receptor Modulators

Methods and compositions for determining whether a test compound specifically binds to a mammalian chemosensory, and more particularly, an IVA olfactory receptor of the invention, both in vitro and in vivo are described below. Many aspects of cell physiology can be monitored to assess the effect of ligand-binding to a naturally-occurring or chimeric olfactory receptor. These assays may be performed on intact cells expressing an olfactory receptor, on permeabilized cells or on membrane fractions produced by standard methods.

Olfactory receptors are normally located on the specialized cilia of olfactory neurons. These receptors bind odorants and initiate the transduction of chemical stimuli into electrical signals. An activated or inhibited G protein will in turn alter the properties of target enzymes, channels, and other effector proteins. Some examples include the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Preferably, the amino acid sequence identity will be at least 50–75% preferably 85%, 90%, 95%, 96%, 97%, 98%, or 99%. Optionally, the polypeptide of the assays can comprise a domain of an IVA OR protein, such as an extracellular domain, transmembrane region, transmembrane domain, cytoplasmic domain, ligand-binding domain, subunit association domain, active site, and the like. Either the IVA OR protein or a domain thereof can be covalently linked to a heterologous protein to create a chimeric protein used in the assays described herein. The subgenus of IVA ORs provided herein exhibits substantial sequence similarity at both the DNA and protein level, but also significant dissimilarly. With respect thereto, the OR family members possess an average percentage sequence identity to other members of the family when determined over the full length of the gene by about 30%. Moreover, different members of the genes at the protein level exhibit an average on the order of about 40% sequence identity to other members of the family when the full length protein sequences are compared. However, while there exist differences, there are characteristic similarities, e.g. the consensus sequence already mentioned, which further define members of this novel genus of receptors.

Modulators of IVA OR activity can be tested using IVA OR polypeptides as described above, either recombinant or naturally occurring. The protein can be isolated, expressed in a cell, expressed in a membrane derived from a cell, expressed in tissue or in an animal, either recombinant or naturally occurring. Modulation can be tested using one of the in vitro or in vivo assays described herein.

In Vitro Binding Assays

Olfactory transduction can also be examined in vitro with soluble or solid state reactions, using a full-length IVA OR or a chimeric molecule such as an extracellular domain or transmembrane region, or combination thereof, of a IVA OR covalently linked to a heterologous signal transduction domain, or a heterologous extracellular domain and/or transmembrane region covalently linked to the transmembrane and/or cytoplasmic domain of an IVA OR. Furthermore, ligand-binding domains of the protein of interest can be used in vitro in soluble or solid state reactions to assay for ligand binding. In numerous embodiments, a chimeric receptor will be made that comprises all or part of an IVA OR polypeptide, as well an additional sequence that facilitates the localization of the IVA OR to the membrane, such as a rhodopsin, e.g., an N-terminal fragment of a rhodopsin protein, e.g. bovine or another mammalian rhodopsin. Ligand binding to a IVA OR protein, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbence, refractive index) hydrodynamic (e.g., shape), chromatographic, or solubility properties.

Receptor-G protein interactions can also be examined. For example, binding of the G protein to the receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors, e.g., by adding an activator to the receptor and G protein in the absence of GTP, which form a tight complex, and then screen for inhibitors by looking at dissociation of the receptor-G protein complex. In the presence of GTP, release of the alpha subunit of the G protein from the other two G protein subunits serves as a criterion of activation.

Particularly preferred G proteins include the chimeric and variant G proteins disclosed in U.S. Provisional Application No. 60/243,770, filed on Oct. 30, 2000; U.S. Ser. No. 09/984,292 filed Oct. 29, 2001; and U.S. Ser. No. 09/989, 497 filed Nov. 21, 2001. These G proteins have been altered such that they exhibit greater coupling efficiencies with specific olfactory or taste receptor.

An activated or inhibited G protein will in turn alter the properties of target enzymes, channels, and other effector proteins. The classic examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

In another embodiment of the invention, a GTPγS assay may be used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively-labeled GTPγ$^{35}$S to the G protein in the presence of a putative ligand. Typically, membranes containing the chemosensory receptor of interest are mixed with a complex of G proteins. Potential inhibitors and/or activators and GTPγS are added to the assay, and binding of GTPγS to the G protein is measured. Binding can be measured by liquid scintillation counting or by any other means known in the art, including scintillation proximity assays (SPA). In other assays formats, fluorescently-labeled GTPγS can be utilized.

Fluorescence Polarization Assays

In another embodiment, Fluorescence Polarization ("FP") based assays may be used to detect and monitor odorant binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of odorants to the olfactory receptors of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor odorant-binding which may activate or inhibit the olfactory receptors of the invention, fluorescence-labeled odorants or auto-fluorescent odorants may be used.

Fluorescence polarization (P) is defined as:

$$P = \frac{Int_{\parallel} - Int_{\perp}}{Int_{\parallel} + Int_{\perp}}$$

where II is the intensity of the emission light parallel to the excitation light plane and Int I ⊥ is the intensity of the emission light perpendicular to the excitation light plane. P, being a ratio of light intensities, is a dimensionless number. For example, the Beacon® and Beacon 2000™ System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236–240, which gives a thorough explanation of this equation. Summarily, the Perrin equation states that polarization is directly proportional to the rotational relaxation time, the time that it takes a molecule to rotate through an angle of approximately 68.5° Rotational relaxation time is related to viscosity (η), absolute temperature (T), molecular volume (V), and the gas constant (R) by the following equation:

$$RotationalRelaxationTime = \frac{3\eta V}{RT}$$

The rotational relaxation time is small (≈1 nanosecond) for small molecules (e.g. fluorescein) and large (≈100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

Solid State and Soluble High Throughput Assays

In yet another embodiment, the invention provides soluble assays using molecules such as a domain such as ligand-binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; an IVA OR protein; or a cell or tissue expressing an IVA OR protein, either naturally occurring or recombinant. In another embodiment, the invention provides solid phase based in vitro assays in a high throughput format, where the domain, chimeric molecule, IVA OR protein, or cell or tissue expressing the IVA OR is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. Further, it is possible to assay several different plates per day; assay screens for up to about 6,000–20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest (e.g., the olfactory transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface which is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.*, 85:2149–54 (1963) (describing solid phase synthesis of, e.g., peptides); Geysen et al., *J. Immun. Meth.*, 102:259–74 (1987) (describing synthesis of solid phase components on pins); Frank & Doring, *Tetrahedron*, 44:60316040 (1988) (describing synthesis of various peptide sequences on cellulose disks); Fodor et al., *Science*, 251:767–77 (1991); Sheldon et al., *Clinical Chemistry*, 39(4):718–19 (1993); and Kozal et al., *Nature Medicine*, 2(7):753759 (1996) (all describing arrays of biopolymers fixed to solid substrates). Non-chemical approaches for fixing tag binders to substrates include other common methods, such as heat, cross-linking by UV radiation, and the like.

Computer-based Assays

Yet another assay for compounds that modulate VA OR protein activity involves computer assisted compound design, in which a computer system is used to generate a three-dimensional structure of an IVA OR protein based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding an IVA OR polypeptide into the computer system. The nucleotide sequence encoding the polypeptide, or the amino acid sequence thereof, can be any of the IVA or polypeptides already identified or chimeras, variants or fragments thereof.

The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand-binding regions are identified by the computer system. Three-dimensional structures for potential ligands are generated by entering amino acid or nucleotide sequences or chemical formulas of compounds, as described above. The three-dimensional structure of the potential ligand is then compared to that of the IVA OR protein to identify ligands that bind to the protein. Binding affinity between the protein and ligands is determined using energy terms to determine which ligands have an enhanced probability of binding to the protein.

Computer systems are also used to screen for mutations, polymorphic variants, alleles and interspecies homologs of IVA OR genes. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated IVA OR genes involves receiving input of a first nucleic acid or amino acid sequence of a IVA OR gene, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various IVA OR genes, and mutations associated with disease states and genetic traits.

Cell-based Binding Assays

In a preferred embodiment, an IVA OR polypeptide is expressed in a eukaryotic cell as a chimeric receptor with a heterologous, chaperone sequence that facilitates its maturation and targeting through the secretory pathway. For example, the heterologous sequence can comprise a rhodopsin sequence, such as an N-terminal fragment of a rhodopsin. Such chimeric IVA OR receptors can be expressed in any eukaryotic cell, such as HEK-293 cells. Preferably, the cells comprise a functional G protein, e.g., $G\alpha15$, that is capable of coupling the chimeric receptor to an intracellular signaling pathway or to a signaling protein such as phospholipase C or the chimeric or variant G proteins previously identified. Activation of such chimeric receptors in such cells can be detected using any standard method, such as by detecting changes in intracellular calcium by detecting FURA-2 dependent fluorescence in the cell.

Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G proteins. The kinase/arrestin pathway plays a key role in the desensitization of many GPCR receptors. For example, compounds that modulate the duration an olfactory receptor stays active would be useful as a means of prolonging a desired odor or cutting off an unpleasant one. For a general review of GPCR signal transduction and methods of assaying signal transduction, see, e.g., *Methods in Enzymology, vols.* 237 and 238 (1994) and volume 96 (1983); Bourne et al., *Nature,* 10:349:117–27 (1991); Bourne et al., *Nature,* 348:125–32 (1990); Pitcher et al., *Annu. Rev. Biochem.,* 67:653–92 (1998).

IVA OR modulation may be assayed by comparing the response of an IVA OR polypeptide treated with a putative IVA OR modulator to the response of an untreated control sample. Such putative IVA OR modulators can include odorants that either inhibit or activate IVA OR polypeptide activity. In one embodiment, control samples (untreated with activators or inhibitors) are assigned a relative OR activity value of 100. Inhibition of an IVA OR polypeptide is achieved when the OR activity value relative to the control is about 90%, optionally 50%, optionally 25–0%. Activation of an OR polypeptide is achieved when the OR activity value relative to the control is 110%, optionally 150%, 200–500%, or 1000–2000%.

Preferably molecules will be identified that inhibit IVA OR activity, as these molecules should be useful as anti-odorants for blocking the odor of IVA and structurally related compounds.

Changes in ion flux may be assessed by determining changes in polarization (i.e., electrical potential) of the cell or membrane expressing a OR protein. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.*, 336:1575–1595 (1997)). Whole cell currents are conveniently determined using the standard. Other known assays include: radiolabeled ion flux assays and fluorescence assays using voltage-sensitive dyes (see, e.g., Vestergarrd-Bogind et al., *J. Membrane Biol.*, 88:67–75 (1988); Gonzales & Tsien, *Chem. Biol.*, 4:269277 (1997); Daniel et al., *J. Pharmacol. Meth.*, 25:185–193 (1991); Holevinsky et al., *J. Membrane Biology*, 137:59–70 (1994)). Generally, the compounds to be tested are present in the range from 1 pM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Preferred assays for GPCRs include cells that are loaded with ion or voltage sensitive dyes to report receptor activity. Assays for determining activity of such receptors can also use known agonists and antagonists for other G protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G protein coupled receptors, promiscuous G proteins such as $G\alpha 15$ and $G\alpha 16$ can be used in the assay of choice (Wilkie et al., *PNAS*, 88:10049–53 (1991)). Such promiscuous G proteins allow coupling of a wide range of receptors. Alternatively, the chimeric and variant G proteins disclosed in the patent applications incorporated by reference supra may be utilized. In case of mammalian olfactory receptors, such G proteins as Golf and Gs may also be utilized to couple these receptors to cyclic nucleotide-regulated signaling pathways.

Receptor activation typically initiates subsequent intracellular events, e.g., increases in second messengers such as IP3, which releases intracellular stores of calcium ions. Activation of some G protein coupled receptors stimulates the formation of inositol triphosphate (IP3) through phospholipase C-mediated hydrolysis of phosphatidylinositol (Berridge & Irvine, *Nature*, 312:315–21 (1984)). IP3 in turn stimulates the release of intracellular calcium ion stores. Thus, a change in cytoplasmic calcium ion levels, or a change in second messenger levels such as IP3 can be used to assess G protein coupled receptor function. Cells expressing such G protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *PNAS*, 88:9868–72 (1991) and Dhallan et al., *Nature*, 347: 184–187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In a preferred embodiment, IVA OR protein activity is measured by expressing an IVA OR gene in a heterologous cell with a promiscuous G protein that links the receptor to a phospholipase C signal transduction pathway (see Offermanns & Simon, *J. Biol. Chem.*, 270:15175–15180 (1995)). Optionally the cell line is HEK-293 (which does not naturally express OR genes) and the promiscuous G protein is $G\alpha 15/G\alpha 16$ (Offermanns & Simon, supra). Modulation of olfactory transduction is assayed by measuring changes in intracellular $Ca^{2+}$ levels, which change in response to modulation of the OR signal transduction pathway via administration of a molecule that associates with a OR protein. Changes in $Ca^{2+}$ levels are optionally measured using fluorescent $Ca^{2+}$ indicator dyes and fluorometric imaging.

In one embodiment, the changes in intracellular cAMP or cGMP can be measured using immunoassays. The method described in Offermanns & Simon, *J. Bio. Chem.*, 270: 15175–15180 (1995), may be used to determine the level of cAMP. Also, the method described in Felley-Bosco et al., *Am. J. Resp. Cell and Mol. Biol.*, 11:159–164 (1994), may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

In another embodiment, transcription levels can be measured to assess the effects of a test compound on signal transduction. A host cell containing an OR protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, '3-galactosidase and alkaline phosphatase. Furthermore, the protein of interest can be used as an indirect reporter via attachment to a second reporter such as green fluorescent protein (see, e.g., Mistili & Spector, *Nature Biotechnology*, 15:961–64 (1997)).

The amount of transcription is then compared to the amount of transcription in either the same cell in the absence of the test compound, or it may be compared with the amount of transcription in a substantially identical cell that lacks the IVA OR protein of interest. A substantially identical cell may be derived from the same cells from which the recombinant cell was prepared but which had not been modified by introduction of heterologous DNA. Any difference in the amount of transcription indicates that the test compound has in some manner altered the activity of the IVA OR protein of interest.

Transgenic Non-human Animals Expressing IVA Olfactory Receptors

Non-human animals expressing one or more IVA olfactory receptor sequences of the invention, particularly human IVA olfactory receptor sequences, can also be used for receptor assays. Such expression can be used to determine whether a test compound specifically binds to a mammalian olfactory transmembrane receptor polypeptide in vivo by contacting a non-human animal stably or transiently transfected with a nucleic acid encoding an olfactory receptor or ligand-binding region thereof with a test compound and determining whether the animal reacts to the test compound by specifically binding to the receptor polypeptide.

Use of the translocation domains of the invention in the fusion polypeptides generates a cell expressing high levels of olfactory receptor. Animals transfected or infected with the vectors of the invention are particularly useful for assays to identify and characterize odorants/ligands that can bind to a specific or sets of receptors. Such vector-infected animals expressing libraries of human olfactory sequences can be used for in vivo screening of odorants and their effect on, e.g., cell physiology (e.g., on olfactory neurons), on the CNS (e.g., olfactory bulb activity), or behavior.

Means to infect/express the nucleic acids and vectors, either individually or as libraries, are well known in the art. A variety of individual cell, organ or whole animal parameters can be measured by a variety of means. For example, recording of stimulant-induced waves (bulbar responses) from the main olfactory bulb or accessory olfactory bulb is a useful tool for measuring quantitative stable olfactory responses. When electrodes are located on the olfactory bulb surface it is possible to record stable responses over a period of several days (see, e.g., Kashiwayanagi, *Brain Res. Protoc.* 1:287–291 (1997)). In this study, electroolfactogram recordings were made with a four-electrode assembly from the olfactory epithelium overlying the endoturbinate bones facing the nasal septum. Four electrodes were fixed along the dorsal-to-ventral axis of one turbinate bone or were placed in corresponding positions on four turbinate bones and moved together up toward the top of the bone. See also, Scott, *J. Neurophysiol.* 77:1950–1962 (1997); Scott, *J. Neurophysiol.* 75:2036–2049 (1996); Ezeh, *J. Neurophysiol.* 73:2207–2220 (1995). In other systems, fluorescence changes in nasal epithelium can be measured using the dye di-4-ANEPPS, which is applied on the rat's nasal septum and medial surface of the turbinates (see, e.g., Youngentob, *J. Neurophysiol.* 73:387–398 (1995)). Extracellular potassium activity (aK) measurements can also be carried out in in vivo. An increase in aK can be measured in the mucus and the proximal part of the nasal epithelium (see, e.g., Khayari, *Brain Res.* 539:1–5 (1991)).

The IVA OR sequences of the invention can be for example expressed in animal nasal epithelium by delivery with an infecting agent, e.g., adenovirus expression vector. Recombinant adenovirus-mediated expression of a recombinant gene in olfactory epithelium using green fluorescent protein as a marker is described by, e.g., Touhara, *PNAS*, 96:4040–45 (1999).

The endogenous olfactory receptor genes can remain functional and wild-type (native) activity can still be present. In other situations, where it is desirable that all olfactory receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, *Transgenic Res* 6:97–106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, *Hum. Mol Genet.* 7:53–62 (1998); Moreadith, *J. Mol. Med.* 75:208–216 (1997); Tojo, *Cytotechnology* 19:161–165 (1995); Mudgett, *Methods Mol. Biol.* 48:167–184 (1995); Longo, *Transgenic Res.* 6:321–328 (1997); U.S. Pat. Nos. 5,616,491; 5,464,764; 5,631,153; 5,487,992; 5,627,059; 5,272,071; WO 91/09955; WO 93/09222; WO 96/29411; WO 95/31560; WO 91/12650.

The nucleic acid libraries of the invention can also be used as reagents to produce "knockout" human cells and their progeny. Likewise, the nucleic acids of the invention can also be used as reagents to produce "knock-ins" in mice. The human or rat IVA OR gene sequences can replace the orthologous IVA ORs in the mouse genome. In this way, a mouse expressing a human or rat IVA OR can be produced. This mouse can then be used to analyze the function of human or rat IVA ORs, and to identify ligands for such IVA ORs.

Modulators

The compounds tested as modulators of an IVA OR subgenus member can be any small chemical compound, or a biological entity, such as a protein, sugar, nucleic acid or lipid. Alternatively, modulators can be genetically altered versions of an IVA OR gene. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

The IVA OR modulating compounds can be used in any number of consumer products, including, but not limited to, perfumes, fragrance compositions, deodorants, air fresheners, foods, drugs, etc., or ingredients thereof, to thereby modulate the odor of the product, composition, or ingredient in a desired manner. As one of skill in the art will recognize, that IVA OR modulating compounds preferably will be used to block malodors, i.e. attributable to IVA and structurally related carboxylic acids.

In one preferred embodiment, high throughput screening methods involve providing a combinatorial chemical or peptide library containing a large number of potential anti-odorant compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual anti-odorant compositions.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.*, 37:487–93 (1991) and Houghton et al., *Nature*, 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS*, 90:6909–13 (1993)), vinylogous polypeptides (Hagihara et al., *J. Amer. Chem. Soc.*, 114:6568 (1992)), nonpeptidal peptidomimetics with glucose scaffolding (Hirschmann et al., *J. Amer. Chem. Soc.*, 114:9217–18 (1992)), analogous organic syntheses of small compound libraries (Chen et al., *J. Amer. Chem. Soc.*, 116:2661 (1994)), oligocarbamates (Cho et al., *Science*, 261:1303 (1993)), peptidyl phosphonates (Campbell et al., *J. Org. Chem.*, 59:658 (1994)), nucleic acid libraries (Ausubel, Berger and Sambrook, all supra), peptide nucleic acid libraries (U.S. Pat. No. 5,539,083), antibody libraries (Vaughn et al., *Nature Biotechnology*, 14(3):309–14 (1996) and PCT/US96/10287), carbohydrate libraries (Liang et al., *Science*, 274:1520–22 (1996) and U.S. Pat. No. 5,593,853), small organic molecule libraries (benzodiazepines, Baum, *C&EN*, Jan 18, page 33 (1993); thiazolidinones and metathiazanones, U.S. Pat. No. 5,549,974; pynrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

Kits

IVA OR genes and their homologs are useful tools for identifying IVA olfactory receptor expressing cells, for forensics and paternity determinations, and for examining olfactory transduction. IVA OR subgenus member-specific reagents that specifically hybridize to IVA OR nucleic acids, and IVA OR subgenus member-specific reagents that specifically bind to an IVA OR protein, e.g., anti-IVA OR antibodies are used to examine olfactory cell expression and olfactory transduction regulation.

Nucleic acid assays for the presence of DNA and RNA for an OR family member in a sample include numerous techniques are known to those skilled in the art, such as southern analysis, northern analysis, dot blots, RNase protection, S1 analysis, amplification techniques such as PCR, and in situ hybridization. In in situ hybridization, for example, the target nucleic acid is liberated from its cellular surroundings in such a form so as to be available for hybridization within the cell, while preserving the cellular morphology for subsequent interpretation and analysis. The following articles provide an overview of the art of in situ hybridization: Singer et al., *Biotechniques*, 4:230–50 (1986); Haase et al., *Methods in Virology*, vol. VII, pp. 189–226 (1984); and *Nucleic Acid Hybridization: A Practical Approach* (Names et al., eds. 1987). In addition, an OR protein can be detected with the various immunoassay techniques described above. The test sample is typically compared to both a positive control (e.g., a sample expressing a recombinant OR protein) and a negative control.

The present invention also provides for kits for screening for modulators of IVA OR subgenus members. Such kits can be prepared from readily available materials and reagents. For example, such kits can comprise any one or more of the following materials: one or more IVA OR nucleic acids or proteins, reaction tubes, and instructions for testing IVA OR activity. Optionally, the kit contains a biologically active IVA OR receptor. A wide variety of kits and components can be prepared according to the present invention, depending upon the intended user of the kit and the particular needs of the user.

The present invention also embraces compositions containing compounds which modulate the activity of at least one IVA OR receptor according to the invention. These compounds based on their activity should inhibit malodor attributable to isovaleric acid and structurally related carboxylic acids such as those identified infra that are comprised in animal and human axillary secretions (sweat).

Compositions wherein such compounds should be useful include by the way of example deodorants, pet deodorizers, carpet fresheners, air deodorizers, fabric deodorizers, and other compositions that are intended to inhibit such odors.

EXAMPLES

Example 1

Isolation and Imaging of Individual Murine Olfactory Neurons

In this example, the details of how the individual murine olfactory neurons were isolated from murine olfactory epithelium and subjected to $Ca^{2+}$ imaging are described.

Olfactory neuroepithelium was dissected from Balb/C mice and placed in a small Petri dish with phosphate-buffered saline (PBS) without $Ca^{2+}$ and $Mg^{2+}$. The tissue was fragmented under the dissecting microscope into pieces as small as possible. The buffer was removed and replaced by 2 ml of fresh PBS without $Ca^{2+}$ and $Mg^{2+}$ supplemented with 0.025% trypsin, 0.75 mM EDTA for 15 min. After dissociation, the tissue was transferred into 5 ml PBS without $Ca^{2+}$ and $Mg^{2+}$ and the tissue was triturated very gently by pipetting up and down 4–5 times with plastic disposable, progress of cell dissociation was monitored under inverted microscope. After dissociation, the tissue was transferred into 10 ml of Dulbecco's modified Eagle medium (DMEM) supplemented with 10% Calf serum, centrifuged 10 min at 2000 g. Supernatant was removed, 5 ml of cold PBS without $Ca^{2+}$ and $Mg^{2+}$ were added and the tissue suspension (kept on ice) was triturated very gently by pipetting up and down 4–5 times with pipettes and pipetman tips of gradually decreasing diameters: 2 ml plastic pipette, 1 ml plastic pipette, then 1 ml followed by 200 μl-tip Pipetman. The isolated cells were then incubated with 10 μM Fura-2 AM for 45 min. Isolated olfactory sensory neurons were identified in an inverted microscope field either by their morphology alone (for random control neurons) or by the morphology and ability to respond to IVA as detected by $Ca^{2+}$-imaging. An example of IVA response of an isolated murine olfactory sensory neuron is represented In FIG. 3. Fluorescence measurements were conducted at room temperature on an inverted microscope (Zeiss Axiovert 100, Carl Zeiss). Fura-2 loaded neurons were illuminated at excitation wavelengths (360 and 380 nm). Emitted fluorescence passed throgh the objective, the dichroic mirrior (DCPL405) and an emission filter (510±40 nm) and was collected by a cooled charge-coupled device (CCD) camera (Quantix, Photomerics) mounted on the microscopy. Metafluro imaging software (Universal Imaging Inc.) were used to acquire the images at 10 seconds intervals. The responsive neurons were then picked with a glass microcapillary pipette.

The pipette contents (~0.5 μl or less) were then ejected by positive pressure (with syringe) into a PCR tube with 4 μl of the lysis buffer (0.5% Nonidet NP-40, 10 μM of each dNTP, 5 units/μl of Prime RNAse inhibitor (3'-5', Inc.), 324 units/ml RNAguard (Pharmacia), 1×MMLV reverse transcriptase buffer (GIBCO-BRL), 0.005 $OD_{260}$/ml pd(T)19–24 primer in DEPC-treated water). The collection tubes were briefly centrifuged immediately to make sure the cell is indeed in the lysis buffer. Sample tubes were stored on ice for up to 2 hours before starting the next step.

FIG. 3 shows response of a single olfactory neuron to IVA indicated by changes in fura-2 fluorescence intensity ratios (340/380 nm). Either high $K^+$ solution or IVA at either 100 μM or 10 μM were applied. The neuron was washed continuously between applications of high $K^+$ and IVA.

Example 2

Single-cell cDNA Synthesis and PCR Amplification of OR cDNA Fragments

The single neurons collected in lysis buffer were heated to 65° C. in a water bath for 1 min to lyse the cells, then kept at room temperature for 1–2 min to allow the oligo (dT) primer to anneal to the RNA and put back on ice. The tube was centrifuged briefly and 0.5 μl of a 1:1 mix of AMV- and MMLV-reverse transcriptases (Gibco-BRL) were added followed by incubation for 15 min at 37° C. For control experiments, the reaction mixture was divided into two equal aliquots—one for reverse transcriptase reaction (cDNA synthesis) and another for a negative control without reverse transcriptase. After incubation, the reverse transcriptases were inactivated by incubation for 10 min at 65° C., the tubes were put back on ice, then briefly centrifuged (2 min at 4° C.). 4.5 μl of 2× tailing buffer (stock tailing buffer: 800 μl of 5× Gibco-BRL terminal transferase buffer, 30 μl of 100 mM dATP, 1.17 ml $H_2O$) containing 10 units of terminal transferase were added and the reaction mix was incubated at 37° C. for 15 min, inactivated for 10 min at 65° C., put back on ice and centrifuged briefly. PCR amplification reactions were done in Perkin Elmer DNA Thermal Cycler 480. Freshly made ice cold PCR buffer (90 μl) was added to the reaction mixture described above. Composition of the PCR buffer (all reagents and PCR mix were kept on ice to avoid primer dimers): 10 μl of 10×PCR buffer II (Perkin Elmer), 10 μl of 25 mM $MgCl_2$, 0.5 μl of 20 mg/ml BSA, 1 μl of each 100 mM dNTP, 1 μl of 5% Triton X-100, 5 μg of AL1 oligonucleotide primer dATTGGATCCAGGC-CGCTTGGACAAAAATGAA $TC(T)_{24}$ (SEQ ID NO: 86), 90 μl $H_2O$, 2 μl of AmpliTaq polymerase (Perkin Elmer), 1–2 drops of mineral oil (Sigma M5904). Twenty five cycles of amplification were performed in the following conditions: 94° C. for 1 min, 42° C. for 2 min, 72° C. for 6 min with 10 sec extension time at each cycle. When these 25 cycles were finished, 1 μl of AmpliTaq polymerase were added directly to each tube and 25 more cycles were performed with the same program as above, but without extension time. One μl aliquots of the first PCR reactions supplied with 0.2 mM of each dNTP, 2 μM of each degenerate OR primer in a pair used for a given reaction (primers p41+214, 213+214, TM3D+TM71) and 2.5U of AmpliTaq polymerase in 1×PCR buffer II (Perkin Elmer) were amplified using the following program: 94° C. for 5 min, 45 cycles of PCR (1 min 94° C., 3 min 40° C., 3 min 72° C.), final extension at 72° C. for 7 min. The PCR reaction mixtures were analyzed by 1% agarose gel electrophoresis. DNA fragments from the successful reactions (as judged by the expected size of a fragment and absence of DNA contamination confirmed by negative control reactions) were TA-cloned in pCRII-TOPO vector (Invitrogen) and fully sequenced.

While the foregoing detailed description has described several embodiments of the present invention, it is to be understood that the above description is illustrative only and not limiting of the disclosed invention. The invention is to be limited only by the claims which follow.

What is claimed:

1. A method of screening for a compound that putatively blocks isovaleric acid associated malodor comprising:
   (i) contacting an isovaleric acid olfactory receptor polypeptide that possesses at least 95% sequence identity to the polypeptide contained in SEQ ID NO:24 with at least one compound;
   (ii) assaying whether said at least one compound inhibits the binding of said olfactory receptor polypeptide to isovaleric acid; and
   (iii) identifying a compound that putatively blocks isovaleric associated malodor if it inhibits the said binding of said olfactory receptor polypeptide to isovaleric acid.

2. The screening method of claim 1 wherein said identified compound is assessed in a smell test to determine whether said identified compound blocks or inhibits isovaleric acid associated malodor.

3. The screening method of claim 1 wherein the olfactory receptor polypeptide has the sequence contained in SEQ ID NO:24.

4. The method of claim 1 wherein said olfactory receptor polypeptide is expressed by a cell that also expresses a G protein.

5. The method of claim 4 wherein the G protein is Galpha15 or Galpha16.

6. The screening method of claim 4 wherein the cell is selected from a HEK-293, COS, and a CHO cell.

7. The screening method of claim 4 wherein the cell is bound to a solid phase.

8. A method of identifying a compound that putatively modulates isovaleric acid associated malodor comprising:
   (i) contacting a cell line that expresses an isovaleric acid receptor polypeptide that has a sequence that is at least 95% identical to SEQ ID NO:24 with at least one compound;
   (ii) screening for compounds that block or inhibit the activity of said olfactory receptor polypeptide; and
   (iii) identifying a compound that putatively modulates isovaleric acid associated malodor if it blocks or inhibits the activity of said isovaleric acid receptor polypeptide.

9. The method of claim 8 wherein the receptor is expressed by a cell that additionally expresses a G protein.

10. The method of claim 8 wherein said cell is selected from a Xenopus oocyte, CHO cell, HEK-293 cell and a HeLa cell.

11. The method of claim 9 wherein the G protein is Galpha15 or Galpha16.

12. The method of claim 8 wherein said receptor polypeptide has the sequence contained in SEQ ID NO:24.

13. The method of claim 8 wherein the screening assay selects for compounds that affect receptor internalization.

14. The method of claim 8 wherein the screening assay selects for compounds that affect receptor phosphorylation.

15. The method of claim 8 wherein the screening assay selects for compounds that affect arrestin translocation.

16. The method of claim 8 wherein the assay screens for compounds that affect G protein activation of said receptor.

17. The method of claim 8 wherein the screening assay selects for compounds that affect the conformation of said olfactory receptor polypeptide.

18. The method of claim 17 wherein the screening assay selects for compounds that alter the susceptibility of said receptor polypeptide to proteolysis.

19. The method of claim 17 wherein the screening assay detects any change in conformation using NMR spectroscopy.

20. The method of claim 17 wherein the screening assay detects any conformational change by fluorescence spectroscopy.

21. The method of claim 8 which screens for compounds that displace binding of a radioactively or fluorescently labeled ligand to said olfactory receptor polypeptide.

22. The method of claim 21 which detects the displacement of said labeled compound by fluorescence polarization or FRET assay.

23. The method of claim 8 which is a high throughput screening assay.

24. The method of claim 8 wherein the receptor is attached to a peptide that facilitates surface expression.

25. The method of claim 8 wherein a gene encoding the receptor is operably linked to a reporter gene.

26. The method of claim 25 wherein the reporter is luciferase, beta galactosidase, alkaline phosphatase or beta lactamase.

* * * * *

SEQUENCE LISTING

<160> NUMBER OF SEQ ID NOS: 86

<210> SEQ ID NO 1
<211> LENGTH: 936
<212> TYPE: DNA
<213> ORGANISM: Murine sp.

<400> SEQUENCE: 1

| | | |
|---|---|---|
| atgggaaaag aaaatcacac agaactatca caattcctgc tactgggtct ctcagatgat | 60 |
| cctaaattgc agcctattct tttcgggata ttcttattta tgtacctggt cacagtgctt | 120 |
| ggtaacctgc tcatcatcct ggctgtcagt tctgattccc atctccacaa ccccatgtac | 180 |
| ttcttcctct ccaacctctc atttgtagac atgtgtttca cttctaccac tgtcccaaag | 240 |
| atgctggtga acatccagac aaagaacaaa aatatctcct acatgcagtg cctcactcaa | 300 |
| gtctattttt ttatggtgtt tgctggaatg gataatttct actgactgt aatggccttt | 360 |
| gaccgctttg tggctatttg tcaccccta aactacacag tcatcatgaa ccctcacttc | 420 |
| tgttgcttcc ttgtgctaat gtgctggatt atcattttat cagtctccct gtttcatagt | 480 |
| ctattaatga agcaattaac ttttcc atg ggtactgaaa tcccacattt cttctgtgag | 540 |
| ttggctcaaa ttctcagagt agcaagctct gatattctca tcaataatat cgcattatat | 600 |
| gtggctactg ccctgttatg tgtgtttcct gtcactggaa ttctcttctc ttactcgcag | 660 |
| attgtctcct ccttattgaa tatgtcttca gtagtcagca agtatagagc cttttccacc | 720 |
| tgtggatctc acctctgtgt ggtctgtttg ttttatggta cagcactggg ggtttacctc | 780 |
| agttcagctg ggactgatgt ttctcaagga agcactatag cctcagtgat gtatactgtg | 840 |
| gtcactccta tgctcaaccc attcatctac agcctgagga taaagatgt gaaggggct | 900 |
| ctggtaagaa tccttaaagt atattcttgt ccctga | 936 |

<210> SEQ ID NO 2
<211> LENGTH: 311
<212> TYPE: PRT
<213> ORGANISM: Murine sp.

<400> SEQUENCE: 2

Met Gly Lys Glu Asn His Thr Glu Leu Ser Gln Phe Leu Leu Leu Gly
 1               5                  10                  15

Leu Ser Asp Asp Pro Lys Leu Gln Pro Ile Leu Phe Gly Ile Phe Leu
            20                  25                  30

Phe Met Tyr Leu Val Thr Val Leu Gly Asn Leu Leu Ile Ile Leu Ala
        35                  40                  45

Val Ser Ser Asp Ser His Leu His Asn Pro Met Tyr Phe Phe Leu Ser
    50                  55                  60

Asn Leu Ser Phe Val Asp Met Cys Phe Thr Ser Thr Thr Val Pro Lys
65                  70                  75                  80

Met Leu Val Asn Ile Gln Thr Lys Asn Lys Asn Ile Ser Tyr Met Gln
                85                  90                  95

Cys Leu Thr Gln Val Tyr Phe Phe Met Val Phe Ala Gly Met Asp Asn
            100                 105                 110

Phe Leu Leu Thr Val Met Ala Phe Asp Arg Phe Val Ala Ile Cys His
        115                 120                 125

Pro Leu Asn Tyr Thr Val Ile Met Asn Pro His Phe Cys Cys Phe Leu
    130                 135                 140

```
Val Leu Met Cys Trp Ile Ile Ile Leu Ser Val Ser Leu Phe His Ser
145                 150                 155                 160

Leu Leu Met Lys Gln Leu Thr Phe Ser Met Gly Thr Glu Ile Pro His
            165                 170                 175

Phe Phe Cys Glu Leu Ala Gln Ile Leu Arg Val Ala Ser Ser Asp Ile
        180                 185                 190

Leu Ile Asn Asn Ile Ala Leu Tyr Val Ala Thr Ala Leu Leu Cys Val
            195                 200                 205

Phe Pro Val Thr Gly Ile Leu Phe Ser Tyr Ser Gln Ile Val Ser Ser
        210                 215                 220

Leu Leu Asn Met Ser Ser Val Val Ser Lys Tyr Arg Ala Phe Ser Thr
225                 230                 235                 240

Cys Gly Ser His Leu Cys Val Val Cys Leu Phe Tyr Gly Thr Ala Leu
                245                 250                 255

Gly Val Tyr Leu Ser Ser Ala Gly Thr Asp Val Ser Gln Gly Ser Thr
            260                 265                 270

Ile Ala Ser Val Met Tyr Thr Val Val Thr Pro Met Leu Asn Pro Phe
        275                 280                 285

Ile Tyr Ser Leu Arg Asn Lys Asp Val Lys Gly Ala Leu Val Arg Ile
        290                 295                 300

Leu Lys Val Tyr Ser Cys Pro
305                 310

<210> SEQ ID NO 3
<211> LENGTH: 942
<212> TYPE: DNA
<213> ORGANISM: Murine sp.

<400> SEQUENCE: 3
atggaagaac acaatcttac attaatgact gaattcatcc taatgggtat cagtgaccac    60
tctgaattgc aggccccatt atttgggctg atccttgcca tatacatgac ctcaatggta   120
ggtaatatgg gaatcattgt tttaatcact ttggactcac gcctgctaac acccatgtac   180
ttctttataa acacctggc tattacagat cttggatatt ctacagctgt gggacccaaa   240
atgttggaaa attttgttgt agatcaaaat acaatttcat ttaatctttg tgccacacaa   300
ctagctttct ttcttgtatt cattggtagt gagctattca ttctctctgc gatgtcctat   360
gaccgctatg tggccatctg taagcctctg ctctacactg tcctcatgtc caaaaacta   420 tgttgggttc ttatgtcaat gccttatctc tactgcacat tgtgtctct tctcatcaca   480 gtgaagattt ttacttcatc cttctgtggc tacaatgtca ttaaccattt ctactgtgac   540
tgtatcccct gctgtctct actctgttca catgcagagg aaatcgcatt tattgttatg   600
atctttgcag cttttgattt gattgtgtct cttcttattg ttctggtatc ctacatgttt   660
atcctcatag cagttctcag gatgaactct gcagagggca ggtacaaggc tttctccaca   720
tgtgggtccc acctgacagt ggtgacagtg ttctatggta ctttaatatt tatgtatgta   780
caacctcagt ccagtcattc tgatgacaat gataaggtgt cttcattttt ttacaccctc   840
gttatcccca tgctgaatcc tttgatctat agtttgagga caaggatgt aaaatttgcc   900 ctacatagga cttggagaaa tatttgtaag atcttcctt ag                        942

<210> SEQ ID NO 4
<211> LENGTH: 313
<212> TYPE: PRT
<213> ORGANISM: Murine sp.
```

<400> SEQUENCE: 4

| | | | | | | | | | | | | | | |
|---|---|---|---|---|---|---|---|---|---|---|---|---|---|---|
|Met|Glu|Glu|His|Asn|Leu|Thr|Leu|Met|Thr|Glu|Phe|Ile|Leu|Met|Gly|
|1| | | |5| | | | |10| | | | |15|

Ile Ser Asp His Ser Glu Leu Gln Ala Pro Leu Phe Gly Leu Ile Leu
            20                  25                  30

Ala Ile Tyr Met Thr Ser Met Val Gly Asn Met Gly Ile Ile Val Leu
        35                  40                  45

Ile Thr Leu Asp Ser Arg Leu Leu Thr Pro Met Tyr Phe Phe Ile Lys
    50                  55                  60

His Leu Ala Ile Thr Asp Leu Gly Tyr Ser Thr Ala Val Gly Pro Lys
65                  70                  75                  80

Met Leu Glu Asn Phe Val Val Asp Gln Asn Thr Ile Ser Phe Asn Leu
                85                  90                  95

Cys Ala Thr Gln Leu Ala Phe Phe Leu Val Phe Ile Gly Ser Glu Leu
            100                 105                 110

Phe Ile Leu Ser Ala Met Ser Tyr Asp Arg Tyr Val Ala Ile Cys Lys
        115                 120                 125

Pro Leu Leu Tyr Thr Val Leu Met Ser Gln Lys Leu Cys Trp Val Leu
    130                 135                 140

Met Ser Met Pro Tyr Leu Tyr Cys Thr Phe Val Ser Leu Leu Ile Thr
145                 150                 155                 160

Val Lys Ile Phe Thr Ser Ser Phe Cys Gly Tyr Asn Val Ile Asn His
                165                 170                 175

Phe Tyr Cys Asp Cys Ile Pro Leu Leu Ser Leu Leu Cys Ser His Ala
            180                 185                 190

Glu Glu Ile Ala Phe Ile Val Met Ile Phe Ala Ala Phe Asp Leu Ile
        195                 200                 205

Val Ser Leu Leu Ile Val Leu Val Ser Tyr Met Phe Ile Leu Ile Ala
    210                 215                 220

Val Leu Arg Met Asn Ser Ala Glu Gly Arg Tyr Lys Ala Phe Ser Thr
225                 230                 235                 240

Cys Gly Ser His Leu Thr Val Val Thr Val Phe Tyr Gly Thr Leu Ile
                245                 250                 255

Phe Met Tyr Val Gln Pro Gln Ser Ser His Ser Asp Asp Asn Asp Lys
            260                 265                 270

Val Ser Ser Ile Phe Tyr Thr Leu Val Ile Pro Met Leu Asn Pro Leu
        275                 280                 285

Ile Tyr Ser Leu Arg Asn Lys Asp Val Lys Phe Ala Leu His Arg Thr
    290                 295                 300

Trp Arg Asn Ile Cys Lys Ile Phe Pro
305                 310

<210> SEQ ID NO 5
<211> LENGTH: 930
<212> TYPE: DNA
<213> ORGANISM: Murine sp.

<400> SEQUENCE: 5
atgactgagg acaactactc cttgacaaca gagttcatcc tcataggatt ctcagaccac      60
ccagacttaa agatacttct attcctggtg ttatctacca tctatctggt caccatggtg     120
gggaatcttg gctggtggc cttgatctac atggagcctc gtctccacac acccatgtac     180
atctttctgg caacctggc tctcatggat tcctgttgct cctgtgccat cactcctaag     240
atgctagaga actttttttc tgtgaacaga aggatttctc tctatgaatg catggcacag     300

-continued

```
ttctattttc tctgtcttgc tgaaactgca gactgcttcc ttctggcagc catggcctat    360
gaccgctatg tggccatatg caaccctctg cagtaccaca ccatgatgtc caagaagctc    420
tgccttcaaa tgaccacagg agcctacata gcaggaaacc tgcattccat gattcacata    480
gggttcttgt tcaggttaat tttctgcagg tctcatgtga tcaagcactt cttttgtgat    540
gtcctccccc tatacagact ctcatgtgtt gacccttata tcaatgaact gatgatactc    600
atcttttctg gttcagttca aaccttttcc attattatag tcttgatttc ttatttctgc    660
atcctttta ctatattcac aatgaagtcc agagagggaa gaagcaaagc cttatctact     720
tgtgcatccc actttctgtc tgtgtcaata ttctatgggt ctcttctcta cacatatatt    780
cgaccaagtt cacttaatga agggtataaa gacatacctg ttgctatatt ttatactcta    840
gtaattcctt tattaaaccc gtttatttat agtctgagaa ataaagaagt aattaatgtg    900
atgaaaagag caatgaagaa aagattataa                                     930
```

<210> SEQ ID NO 6
<211> LENGTH: 309
<212> TYPE: PRT
<213> ORGANISM: Murine sp.

<400> SEQUENCE: 6

```
Met Thr Glu Asp Asn Tyr Ser Leu Thr Thr Glu Phe Ile Leu Ile Gly
  1               5                  10                  15

Phe Ser Asp His Pro Asp Leu Lys Ile Leu Leu Phe Leu Val Leu Ser
                 20                  25                  30

Thr Ile Tyr Leu Val Thr Met Val Gly Asn Leu Gly Leu Val Ala Leu
             35                  40                  45

Ile Tyr Met Glu Pro Arg Leu His Thr Pro Met Tyr Ile Phe Leu Gly
         50                  55                  60

Asn Leu Ala Leu Met Asp Ser Cys Cys Ser Cys Ala Ile Thr Pro Lys
 65                  70                  75                  80

Met Leu Glu Asn Phe Phe Ser Val Asn Arg Arg Ile Ser Leu Tyr Glu
                 85                  90                  95

Cys Met Ala Gln Phe Tyr Phe Leu Cys Leu Ala Glu Thr Ala Asp Cys
            100                 105                 110

Phe Leu Leu Ala Ala Met Ala Tyr Asp Arg Tyr Val Ala Ile Cys Asn
        115                 120                 125

Pro Leu Gln Tyr His Thr Met Met Ser Lys Lys Leu Cys Leu Gln Met
    130                 135                 140

Thr Thr Gly Ala Tyr Ile Ala Gly Asn Leu His Ser Met Ile His Ile
145                 150                 155                 160

Gly Phe Leu Phe Arg Leu Ile Phe Cys Arg Ser His Val Ile Lys His
                165                 170                 175

Phe Phe Cys Asp Val Leu Pro Leu Tyr Arg Leu Ser Cys Val Asp Pro
            180                 185                 190

Tyr Ile Asn Glu Leu Met Ile Leu Ile Phe Ser Gly Ser Val Gln Thr
        195                 200                 205

Phe Ser Ile Ile Ile Val Leu Ile Ser Tyr Phe Cys Ile Leu Phe Thr
    210                 215                 220

Ile Phe Thr Met Lys Ser Arg Glu Gly Arg Ser Lys Ala Leu Ser Thr
225                 230                 235                 240

Cys Ala Ser His Phe Leu Ser Val Ser Ile Phe Tyr Gly Ser Leu Leu
                245                 250                 255
```

```
Tyr Thr Tyr Ile Arg Pro Ser Ser Leu Asn Glu Gly Tyr Lys Asp Ile
                260                 265                 270

Pro Val Ala Ile Phe Tyr Thr Leu Val Ile Pro Leu Leu Asn Pro Phe
            275                 280                 285

Ile Tyr Ser Leu Arg Asn Lys Glu Val Ile Asn Val Met Lys Arg Ala
        290                 295                 300

Met Lys Lys Arg Leu
305

<210> SEQ ID NO 7
<211> LENGTH: 933
<212> TYPE: DNA
<213> ORGANISM: Murine sp.

<400> SEQUENCE: 7
atgggcaaat taaccacac ttatctgacg gagttcatct tgctgggcct ctcttcagat      60
catcagactc agatcctgct gtttgtggta tttctcatca tctacctgat cactgtgttt     120
gggaacctgc tcatcatact cctcattcat gttgactccc gacttcatac accaatgtac     180
ttctttctaa aaatcctgtc attcaatgat ctctgtttct ctacaacaat tgttccaaag    240
atgctagtcc actttctagg tgtcagaaag accatttcat ttgctgggtg ctcagtgcaa     300
atgttttctt tcctcataat ggggtgtaca gaaagctctc ttctggcagt catgtcatat     360
gaccgctaca tagctgtctg caaaccctg cactactcca ccatcatgac acataaggtt     420
tgtgttctgc tagttgtagg atcctggact agtggaatat ttgtgtctgt agtagatacc    480
tcatttactt tatgcttgac gtaccgggga ccaaatataa tcaatcatta cttttgtgag     540
cctcctgcac tcttaaagct ggcttcagaa gaaacctaca cagctgaaat ggtcatattt    600
gcaatgggta ataataattct cttaggtcct gtctctctta ccttttctc ctattggaat    660 attatctcca ctgtggttca atacaatca ggtgagggga ggctcaaggt tttctctacc     720
tgcagttccc atttattgt tgttatcttc ttctatggct caacaatatt tacctacatg     780
cagccaaact caaagaaaat gaatgaaaag gataaggtaa tctcggtatt ctactcaata    840
gtaacatcca tgatgaaccc attcatttat agcctaagga caaagatgt gaaggggca      900 ttaaagaaag tacttaaaag agagataaga taa                                 933

<210> SEQ ID NO 8
<211> LENGTH: 310
<212> TYPE: PRT
<213> ORGANISM: Murine sp.

<400> SEQUENCE: 8

Met Gly Lys Leu Asn His Thr Tyr Leu Thr Glu Phe Ile Leu Leu Gly
1               5                   10                  15

Leu Ser Ser Asp His Gln Thr Gln Ile Leu Leu Phe Val Val Phe Leu
            20                  25                  30

Ile Ile Tyr Leu Ile Thr Val Phe Gly Asn Leu Leu Ile Ile Leu Leu
        35                  40                  45

Ile His Val Asp Ser Arg Leu His Thr Pro Met Tyr Phe Phe Leu Lys
    50                  55                  60

Ile Leu Ser Phe Asn Asp Leu Cys Phe Ser Thr Thr Ile Val Pro Lys
65                  70                  75                  80

Met Leu Val His Phe Leu Gly Val Arg Lys Thr Ile Ser Phe Ala Gly
                85                  90                  95

Cys Ser Val Gln Met Phe Ser Phe Leu Ile Met Gly Cys Thr Glu Ser
```

|     |     |     |     | 100 |     |     |     | 105 |     |     |     | 110 |     |     |
| --- | --- | --- | --- | --- | --- | --- | --- | --- | --- | --- | --- | --- | --- | --- |
| Ser | Leu | Leu | Ala | Val | Met | Ser | Tyr | Asp | Arg | Tyr | Ile | Ala | Val | Cys | Lys |
|     |     |     |     | 115 |     |     |     | 120 |     |     |     | 125 |     |     |

Ser Leu Leu Ala Val Met Ser Tyr Asp Arg Tyr Ile Ala Val Cys Lys
                115                 120                 125

Pro Leu His Tyr Ser Thr Ile Met Thr His Lys Val Cys Val Leu Leu
            130                 135                 140

Val Val Gly Ser Trp Thr Ser Gly Ile Phe Val Ser Val Val Asp Thr
145                 150                 155                 160

Ser Phe Thr Leu Cys Leu Thr Tyr Arg Gly Pro Asn Ile Ile Asn His
                165                 170                 175

Tyr Phe Cys Glu Pro Pro Ala Leu Leu Lys Leu Ala Ser Glu Glu Thr
            180                 185                 190

Tyr Thr Ala Glu Met Val Ile Phe Ala Met Gly Ile Ile Ile Leu Leu
                195                 200                 205

Gly Pro Val Ser Leu Ile Leu Phe Ser Tyr Trp Asn Ile Ile Ser Thr
            210                 215                 220

Val Val Gln Ile Gln Ser Gly Glu Gly Arg Leu Lys Val Phe Ser Thr
225                 230                 235                 240

Cys Ser Ser His Phe Ile Val Val Ile Phe Phe Tyr Gly Ser Thr Ile
                245                 250                 255

Phe Thr Tyr Met Gln Pro Asn Ser Lys Lys Met Asn Glu Lys Asp Lys
            260                 265                 270

Val Ile Ser Val Phe Tyr Ser Ile Val Thr Ser Met Met Asn Pro Phe
275                 280                 285

Ile Tyr Ser Leu Arg Asn Lys Asp Val Lys Gly Ala Leu Lys Lys Val
            290                 295                 300

Leu Lys Arg Glu Ile Arg
305                 310

<210> SEQ ID NO 9
<211> LENGTH: 960
<212> TYPE: DNA
<213> ORGANISM: Murine sp.

<400> SEQUENCE: 9

```
atggaaacag gaaatgacac tcagctttca gaattctttc ttctgggatt ttcagagaat      60
caacctcaaa ttcagcctgt catatttgga ctgttcctct tcatgtatat attgactttc     120
actgaaaacc tactcatcat catggccatc attgttgact cccacctgca cacccatg      180
tacctcttcc tctctaatct gtcctttgtg acatctgct tcacttccac cactgttcca     240
cagatgctgg taaacattca cacacaaagc aaggccatca cctatgcagg ctgcatcatc     300
cagatgtact tcttactgct tttttcaggg ttagacatct ttctgctgac tgtgatggcc     360
tatgaccgct atgtggccat ctgtcacccc ctgcattaca tgatcatcat gagcacaaga     420
cgctgtggat tgatgattct ggcatgctgg attataggtg ttataaattc cctgttacac     480
accttttttgg tgttacggct gtcattctgc acaaacttgg aaatcccca ttttttctgt     540
gaacttaatc aagttgtaca ccaggcctgt tctgacacct tcttaatga tatggtaatt     600
tacattacag ctatgctact ggctgttggc cccttctctg gtatccttta ctcttactct     660
aggatagtat cctccatttg tgcaatctcc tcagtgcagg ggaagtacaa agcattttcc     720
acctgtgcat ctcacctctc agttgtctcc ttatttttatt gcaccctcct gggagtgtac     780
ctcagctctg ctgtgaccca aaactcacat gctactgcaa cagcttcatt gatgtacact     840
gtggtcaccc ccatgctgaa tcccttcatc tacagtctga ggaacaaaga cataaagaca     900
```

```
gctctgaaaa tcctgttagg gagtgtaact agaagcagat caatggattc accttcataa      960
```

```
<210> SEQ ID NO 10
<211> LENGTH: 318
<212> TYPE: PRT
<213> ORGANISM: Murine sp.

<400> SEQUENCE: 10

Met Glu Thr Gly Asn Asp Thr Gln Leu Ser Glu Phe Phe Leu Leu Gly
  1               5                  10                  15

Phe Ser Glu Asn Gln Pro Gln Ile Gln Pro Val Ile Phe Gly Leu Phe
                 20                  25                  30

Leu Phe Met Tyr Ile Leu Thr Phe Thr Gly Asn Leu Leu Ile Ile Met
             35                  40                  45

Ala Ile Ile Val Asp Ser His Leu His Thr Pro Met Tyr Leu Phe Leu
         50                  55                  60

Ser Asn Leu Ser Phe Val Asp Ile Cys Phe Thr Ser Thr Thr Val Pro
 65                  70                  75                  80

Gln Met Leu Val Asn Ile His Thr Gln Ser Lys Ala Ile Thr Tyr Ala
                 85                  90                  95

Gly Cys Ile Ile Gln Met Tyr Phe Leu Leu Leu Phe Ser Gly Leu Asp
            100                 105                 110

Ile Phe Leu Leu Thr Val Met Ala Tyr Asp Arg Tyr Val Ala Ile Cys
        115                 120                 125

His Pro Leu His Tyr Met Ile Ile Met Ser Thr Arg Arg Cys Gly Leu
    130                 135                 140

Met Ile Leu Ala Cys Trp Ile Ile Gly Val Ile Asn Ser Leu Leu His
145                 150                 155                 160

Thr Phe Leu Val Leu Arg Leu Ser Phe Cys Thr Asn Leu Glu Ile Pro
                165                 170                 175

His Phe Phe Cys Glu Leu Asn Gln Val Val His Gln Ala Cys Ser Asp
            180                 185                 190

Thr Phe Leu Asn Asp Met Val Ile Tyr Ile Thr Ala Met Leu Leu Ala
        195                 200                 205

Val Gly Pro Phe Ser Gly Ile Leu Tyr Ser Tyr Ser Arg Ile Val Ser
    210                 215                 220

Ser Ile Cys Ala Ile Ser Ser Val Gln Gly Lys Tyr Lys Ala Phe Ser
225                 230                 235                 240

Thr Cys Ala Ser His Leu Ser Val Val Ser Leu Phe Tyr Cys Thr Leu
                245                 250                 255

Leu Gly Val Tyr Leu Ser Ser Ala Val Thr Gln Asn Ser His Ala Thr
            260                 265                 270

Ala Thr Ala Ser Leu Met Tyr Thr Val Val Thr Pro Met Leu Asn Pro
        275                 280                 285

Phe Ile Tyr Ser Leu Arg Asn Lys Asp Ile Lys Thr Ala Leu Lys Ile
    290                 295                 300

Leu Leu Gly Ser Val Thr Arg Ser Arg Ser Met Asp Ser Pro
305                 310                 315

<210> SEQ ID NO 11
<211> LENGTH: 942
<212> TYPE: DNA
<213> ORGANISM: Murine sp.

<400> SEQUENCE: 11
atgagtgtgg ccaatgagag catctcacgg gagttcattc tcttagggtt ttcagatcgg      60
```

```
ccatggctgg agctgccgct ctttgtggtg tttctagtgt cctatattct gaccatcttt    120
ggaaatatga tgatcattct tgtgtcccgc ctggattcca aactccacac ccccatgtac    180 ttttcctca ctaacctgtc cttgctggac ctgtgctaca ccacaagcac ggtcccacag     240
atgctcatca acatctgcag cacccggaag gtgatcagct atggtggctg tgtggcccag    300
cttttcattt tcctggcctt gggttccaca gaatgctttc tgctgggcgt catgtccttt    360
gacaggtttg tagccatctg tcggcctctc cactactcag tcatcatgca ccagaggcgc    420
tgcctccagt tggcggctgc atgttggatc agtggcttca gcaactcagt attacagtct    480
acgtggaccc ttcagatgcc actgtgtgga cacaaggaag tggaccattt cttttgcgaa    540
gtccctgccc tgctcaagtt gtcctgtgtg gatacgacag ctaatgaagc agagctgttc    600
ttcatcagtg tgctgtttct tttaataccc gtgaccctca tcctcatatc atatgctttt    660
attgtccagg cagtgttgag aataagatca gctgaaggtc ggcgaaaggc atttgggaca    720
tgtggctccc acctcatcgt ggtggtcctt ttctatggca ctgccatcta catgtatctg    780
cagccaccat cccctacttc caaggaccgg gggaaaatgg tgtctctctt ttatgggatc    840
atcacaccca tgctgaaccc cctcatctac acactcagga caaagaggt aaagggagcg     900 ttcaagaggt tggtgacaag gatcatcctg agtagaaaat aa                       942
```

<210> SEQ ID NO 12
<211> LENGTH: 313
<212> TYPE: PRT
<213> ORGANISM: Murine sp.

<400> SEQUENCE: 12

```
Met Ser Val Ala Asn Glu Ser Ile Ser Arg Glu Phe Ile Leu Leu Gly
  1               5                  10                  15

Phe Ser Asp Arg Pro Trp Leu Glu Leu Pro Leu Phe Val Val Phe Leu
                 20                  25                  30

Val Ser Tyr Ile Leu Thr Ile Phe Gly Asn Met Met Ile Ile Leu Val
             35                  40                  45

Ser Arg Leu Asp Ser Lys Leu His Thr Pro Met Tyr Phe Phe Leu Thr
 50                  55                  60

Asn Leu Ser Leu Leu Asp Leu Cys Tyr Thr Thr Ser Thr Val Pro Gln
 65                  70                  75                  80

Met Leu Ile Asn Ile Cys Ser Thr Arg Lys Val Ile Ser Tyr Gly Gly
                 85                  90                  95

Cys Val Ala Gln Leu Phe Ile Phe Leu Ala Leu Gly Ser Thr Glu Cys
            100                 105                 110

Phe Leu Leu Gly Val Met Ser Phe Asp Arg Phe Val Ala Ile Cys Arg
            115                 120                 125

Pro Leu His Tyr Ser Val Ile Met His Gln Arg Arg Cys Leu Gln Leu
        130                 135                 140

Ala Ala Ala Cys Trp Ile Ser Gly Phe Ser Asn Ser Val Leu Gln Ser
145                 150                 155                 160

Thr Trp Thr Leu Gln Met Pro Leu Cys Gly His Lys Glu Val Asp His
                165                 170                 175

Phe Phe Cys Glu Val Pro Ala Leu Leu Lys Leu Ser Cys Val Asp Thr
            180                 185                 190

Thr Ala Asn Glu Ala Glu Leu Phe Phe Ile Ser Val Leu Phe Leu Leu
            195                 200                 205

Ile Pro Val Thr Leu Ile Leu Ile Ser Tyr Ala Phe Ile Val Gln Ala
```

```
            210                 215                 220
Val Leu Arg Ile Arg Ser Ala Glu Gly Arg Arg Lys Ala Phe Gly Thr
225                 230                 235                 240

Cys Gly Ser His Leu Ile Val Val Leu Phe Tyr Gly Thr Ala Ile
                245                 250                 255

Tyr Met Tyr Leu Gln Pro Pro Ser Pro Thr Ser Lys Asp Arg Gly Lys
            260                 265                 270

Met Val Ser Leu Phe Tyr Gly Ile Ile Thr Pro Met Leu Asn Pro Leu
        275                 280                 285

Ile Tyr Thr Leu Arg Asn Lys Glu Val Lys Gly Ala Phe Lys Arg Leu
    290                 295                 300

Val Thr Arg Ile Ile Leu Ser Arg Lys
305                 310

<210> SEQ ID NO 13
<211> LENGTH: 945
<212> TYPE: DNA
<213> ORGANISM: Murine sp.

<400> SEQUENCE: 13
atgttccaag gaaatctttc cggagtaact gagttcaatc ttgctggttt aacagacaaa      60
ccagggctgc agctgcccct cttcctcctg ttcctaggaa tctatgtggt cacagtggtg     120
gggaatctca gcatgatcac cctgatacta ttcagttctc aactacacac acccatgtat     180
tattttctca gcagtctgtc cttcattgac ctctgccagt ccattgtcat tattcccaaa     240
atgttggtga actttgtgac agtgcagaac atcatctcct accctgaatg tatgacacag     300
ttttgctttt tgctactttt tactattgca gagtgtcaca tgttagctgt aatggcatat     360
gaccgctatg ttgccatttg taagcccttg ctttacaatg ctgtaatgtc ctatcaagtt     420
tgttcctgga tgatatttgg agtatatatt atggcttttg ttggtgccac aactcaaaca     480
gtcttcatgt taaaagtgca ttttgtaag gccaatgtaa taaatcatta cttctgtgat     540
ctttccccac tcctggaact ctcttgttct gatacttta ttaatgaagt attagctttg     600
tgcttcagtg ttttcaatat ctttattcca actctgacaa ttctaagctc ttacatcttc     660
atcatagcca gcatcctccg gattaaatcc actgaaggca ggtccaaagc cttcagcact     720
tgcagctcac acatatcagc agttgctata ttctttggat cccttgcatt catgtacctg     780
cagccatcat caatcaactc catggaccaa aggaaagtgt cctctgtatt ttataccatt     840
gtcgtgccca tgctgaatcc tttgatctac agcctgagga taaggatgt caaagttgct     900 ctaaataagt tccttgaaag aattttttct tgtgaacaaa actaa                    945

<210> SEQ ID NO 14
<211> LENGTH: 314
<212> TYPE: PRT
<213> ORGANISM: Murine sp.

<400> SEQUENCE: 14

Met Phe Gln Gly Asn Leu Ser Gly Val Thr Glu Phe Asn Leu Ala Gly
1               5                   10                  15

Leu Thr Asp Lys Pro Gly Leu Gln Leu Pro Leu Phe Leu Leu Phe Leu
            20                  25                  30

Gly Ile Tyr Val Val Thr Val Val Gly Asn Leu Ser Met Ile Thr Leu
        35                  40                  45

Ile Leu Phe Ser Ser Gln Leu His Thr Pro Met Tyr Tyr Phe Leu Ser
    50                  55                  60
```

```
Ser Leu Ser Phe Ile Asp Leu Cys Gln Ser Ile Val Ile Pro Lys
 65                  70                  75                  80

Met Leu Val Asn Phe Val Thr Val Gln Asn Ile Ile Ser Tyr Pro Glu
                 85                  90                  95

Cys Met Thr Gln Phe Cys Phe Leu Leu Phe Thr Ile Ala Glu Cys
            100                 105                 110

His Met Leu Ala Val Met Ala Tyr Asp Arg Tyr Val Ala Ile Cys Lys
            115                 120                 125

Pro Leu Leu Tyr Asn Ala Val Met Ser Tyr Gln Val Cys Ser Trp Met
        130                 135                 140

Ile Phe Gly Val Tyr Ile Met Ala Phe Val Gly Ala Thr Thr Gln Thr
145                 150                 155                 160

Val Phe Met Leu Lys Val His Phe Cys Lys Ala Asn Val Ile Asn His
                165                 170                 175

Tyr Phe Cys Asp Leu Ser Pro Leu Leu Glu Leu Ser Cys Ser Asp Thr
            180                 185                 190

Phe Ile Asn Glu Val Leu Ala Leu Cys Phe Ser Val Phe Asn Ile Phe
        195                 200                 205

Ile Pro Thr Leu Thr Ile Leu Ser Ser Tyr Ile Phe Ile Ile Ala Ser
        210                 215                 220

Ile Leu Arg Ile Lys Ser Thr Glu Gly Arg Ser Lys Ala Phe Ser Thr
225                 230                 235                 240

Cys Ser Ser His Ile Ser Ala Val Ala Ile Phe Phe Gly Ser Leu Ala
                245                 250                 255

Phe Met Tyr Leu Gln Pro Ser Ser Ile Asn Ser Met Asp Gln Arg Lys
            260                 265                 270

Val Ser Val Phe Tyr Thr Ile Val Val Pro Met Leu Asn Pro Leu
        275                 280                 285

Ile Tyr Ser Leu Arg Asn Lys Asp Val Lys Val Ala Leu Asn Lys Phe
        290                 295                 300

Leu Glu Arg Ile Phe Ser Cys Glu Gln Asn
305                 310

<210> SEQ ID NO 15
<211> LENGTH: 912
<212> TYPE: DNA
<213> ORGANISM: Murine sp.

<400> SEQUENCE: 15
tctgagttta tcctcttaga gctccccatt cagccagagg atcaagctgt gtactttgcc     60
ctgttcctgg ccatgtacct gacaactgtg ctggggaacc tgctcatcat tcttctcatt    120
aggctggact ctcacctcca cacccccatg tacttcttcc tcagtcactt ggccttcacg    180
gacatctctt tctcatctgt cacagctcca aagatgctca tgaatatgct gacacatagc    240
caatccatct cacatgctgg gtgtgtttcc caaatatatt ttttcttatt gtttgggtgt    300
attgacaact tccttctgac ttccatggcc tatgacaggt atgtggccat ctgccaccct    360
ctgcattata ccactatcat gagtcaaagc ctctgtgttc tgctagtgat ggtgtcctgg    420 gcatttcct cttctaatgg ccttgtgcat actcttctct tgctcgtct ctctcttttt      480 agagacaaca ctgtccacca tttttctgt gatctctctg ctttgctgaa gctgtccagc    540
tcagacacta ctatcaatga actagtaatc ctcactttag cagtggtggt catcactgta    600
ccattcatat gcatcctggt ttcttatggc cacatggggg ccactatcct aagaactcca    660
```

```
tccatcaagg gtatctgcaa agccttgtcc acatgtggtt ctcatctctg tgtagtttct    720
ttatattatg gagccattat tgggttatat tttttcccct cctccaataa tactaatgat    780
aaagatgtca tagtagctgt gttgtacact gtggttacac ccatgctgaa tcccttatc    840 tatagtctga ggaatcggga tataaatgga gcattgagaa agacactcag caggagactg    900
tgttcacact ga                                                        912
```

<210> SEQ ID NO 16
<211> LENGTH: 303
<212> TYPE: PRT
<213> ORGANISM: Murine sp.

<400> SEQUENCE: 16

```
Ser Glu Phe Ile Leu Glu Leu Pro Ile Gln Pro Glu Asp Gln Ala
 1               5                  10                  15

Val Tyr Phe Ala Leu Phe Leu Ala Met Tyr Leu Thr Thr Val Leu Gly
                20                  25                  30

Asn Leu Ile Ile Leu Leu Ile Arg Leu Asp Ser His Leu His Thr
            35                  40                  45

Pro Met Tyr Phe Phe Leu Ser His Leu Ala Phe Thr Asp Ile Ser Phe
        50                  55                  60

Ser Ser Val Thr Ala Pro Lys Met Leu Met Asn Met Leu Thr His Ser
65                  70                  75                  80

Gln Ser Ile Ser His Ala Gly Cys Val Ser Gln Ile Tyr Phe Phe Leu
                85                  90                  95

Leu Phe Gly Cys Ile Asp Asn Phe Leu Leu Thr Ser Met Ala Tyr Asp
               100                 105                 110

Arg Tyr Val Ala Ile Cys His Pro Leu His Tyr Thr Thr Ile Met Ser
           115                 120                 125

Gln Ser Leu Cys Val Leu Leu Val Met Val Ser Trp Ala Phe Ser Ser
       130                 135                 140

Ser Asn Gly Leu Val His Thr Leu Leu Phe Ala Arg Leu Ser Leu Phe
145                 150                 155                 160

Arg Asp Asn Thr Val His His Phe Phe Cys Asp Leu Ser Ala Leu Leu
               165                 170                 175

Lys Leu Ser Ser Ser Asp Thr Thr Ile Asn Glu Leu Val Ile Leu Thr
           180                 185                 190

Leu Ala Val Val Val Ile Thr Val Pro Phe Ile Cys Ile Leu Val Ser
       195                 200                 205

Tyr Gly His Met Gly Ala Thr Ile Leu Arg Thr Pro Ser Ile Lys Gly
   210                 215                 220

Ile Cys Lys Ala Leu Ser Thr Cys Gly Ser His Leu Cys Val Val Ser
225                 230                 235                 240

Leu Tyr Tyr Gly Ala Ile Ile Gly Leu Tyr Phe Phe Pro Ser Ser Asn
               245                 250                 255

Asn Thr Asn Asp Lys Asp Val Ile Val Ala Val Leu Tyr Thr Val Val
           260                 265                 270

Thr Pro Met Leu Asn Pro Phe Ile Tyr Ser Leu Arg Asn Arg Asp Ile
       275                 280                 285

Asn Gly Ala Leu Arg Lys Thr Leu Ser Arg Arg Leu Cys Ser His
   290                 295                 300
```

<210> SEQ ID NO 17
<211> LENGTH: 939
<212> TYPE: DNA

<213> ORGANISM: Murine sp.

<400> SEQUENCE: 17

```
atgcctagaa acaacaacca gactaccatc tctcagttcc tcctcctggg tctgcccatc      60
ccccaagagt ttcagcatct gttctatgcc ctgttcctgg ccatgtacct caccactgtc    120
ttggggaacc tcatcatcat catactcatt cgactggact cccatctcca cacacccatg    180
tacttgtttc tcagcaactt gtccttcact gacctctaat tttcctctgt cacaatgccc    240
aagttgctgc agaacatgca gagccaagtt ccttcaatcc cctatgcagg ctgcctgaca    300
caaatgtact tccttttgtt ttttggagat cttgagagct tcctccttgt ggccatggcc    360
tatgaccgct atgtagccat ctgcttccct cttcattaca ccagcatcat gagccccagg    420
ctctgtgtga gtcttgtgct gctgtcctgg ttgctgacca tgtcccattc catgctgcac    480
actttgctct taactaggtt gtctttctgt gaaaacaatg tgatccccca tttttttctgt   540
gatctgtctg ctctgctgaa gctggcctgc tctgatattc acattaatga attggtgata    600
ttgatcatag gagggcttgt tgttatactt ccatttctac tcatcacagt gtcttatgca    660
cgcatcatct cctccattct caaggtccct tcaactcaag catccacaa ggtcttctcc      720
acttgtggtt ctcacctgtc tgtggtgtca ctgttctatg gacaattat tggcctctac      780
ttatgtccat ctgctaataa ctctactcta aaggacactg tcatgtctat gatgtacacc    840
gtggtaactc ccatgctgaa ccccttcatc tacagcctga ggaacagaga catgaaggaa    900
gccctaaaaa gagtgcttca aagaaaact atctttttga                           939
```

<210> SEQ ID NO 18
<211> LENGTH: 312
<212> TYPE: PRT
<213> ORGANISM: Murine sp.
<220> FEATURE:
<221> NAME/KEY: MOD_RES
<222> LOCATION: (73)
<223> OTHER INFORMATION: Variable amino acid

<400> SEQUENCE: 18

```
Met Pro Arg Asn Asn Asn Gln Thr Thr Ile Ser Gln Phe Leu Leu Leu
  1               5                  10                  15
Gly Leu Pro Ile Pro Gln Glu Phe Gln His Leu Phe Tyr Ala Leu Phe
                 20                  25                  30
Leu Ala Met Tyr Leu Thr Thr Val Leu Gly Asn Leu Ile Ile Ile Ile
             35                  40                  45
Leu Ile Arg Leu Asp Ser His Leu His Thr Pro Met Tyr Leu Phe Leu
         50                  55                  60
Ser Asn Leu Ser Phe Thr Asp Leu Xaa Phe Ser Ser Val Thr Met Pro
 65                  70                  75                  80
Lys Leu Leu Gln Asn Met Gln Ser Gln Val Pro Ser Ile Pro Tyr Ala
                 85                  90                  95
Gly Cys Leu Thr Gln Met Tyr Phe Leu Leu Phe Phe Gly Asp Leu Glu
                100                 105                 110
Ser Phe Leu Leu Val Ala Met Ala Tyr Asp Arg Tyr Val Ala Ile Cys
            115                 120                 125
Phe Pro Leu His Tyr Thr Ser Ile Met Ser Pro Arg Leu Cys Val Ser
        130                 135                 140
Leu Val Leu Leu Ser Trp Leu Leu Thr Met Ser His Ser Met Leu His
145                 150                 155                 160
Thr Leu Leu Leu Thr Arg Leu Ser Phe Cys Glu Asn Asn Val Ile Pro
```

```
                    165                 170                 175
His Phe Phe Cys Asp Leu Ser Ala Leu Leu Lys Leu Ala Cys Ser Asp
                180                 185                 190
Ile His Ile Asn Glu Leu Val Ile Leu Ile Ile Gly Gly Leu Val Val
                195                 200                 205
Ile Leu Pro Phe Leu Leu Ile Thr Val Ser Tyr Ala Arg Ile Ile Ser
            210                 215                 220
Ser Ile Leu Lys Val Pro Ser Thr Gln Gly Ile His Lys Val Phe Ser
225                 230                 235                 240
Thr Cys Gly Ser His Leu Ser Val Val Ser Leu Phe Tyr Gly Thr Ile
                245                 250                 255
Ile Gly Leu Tyr Leu Cys Pro Ser Ala Asn Asn Ser Thr Leu Lys Asp
                260                 265                 270
Thr Val Met Ser Met Met Tyr Thr Val Val Thr Pro Met Leu Asn Pro
                275                 280                 285
Phe Ile Tyr Ser Leu Arg Asn Arg Asp Met Lys Glu Ala Leu Lys Arg
                290                 295                 300
Val Leu Gln Lys Lys Thr Ile Phe
305                 310
```

<210> SEQ ID NO 19
<211> LENGTH: 936
<212> TYPE: DNA
<213> ORGANISM: Murine sp.

<400> SEQUENCE: 19

```
atgcaaaacc agagctttgt cactgagttc atactcttgg ggctttccca gaacccaaaa    60
gttgagaaaa tactgtttgt tgtatttttta ttggtctata ttgcaactat tggggggaaac   120
atgataattg tggtgaccat catctatagc cctgcactgt tgagttcccc catgtacttc   180
ttcttaatat ttctgtcttt cctggatgct tgcacttcct ctactgtcac ccccaagatg   240
attgtagact tcttctatga aggaagacc  atctccttgg aatgttgcat cacacaactg   300
tttactagcc acttctttgc aggagttgag gtgattatct tgacatctat ggcctatgac   360
cgctatgtgg ccatctgcaa gcctcttcac tactcttcca tcatgaccag gaggctctgt   420
ggcactctcg taatggtggc ctggacagga ggattcttac attctatcac acaagttatc   480
ttcacgttgc agctacccct ctgtgggccc aattttattg atcatttcat atgtgacttg   540
ttcccattac tgcagcttgc ctgcactgac acacacattt ttgtcatttt ggtgtttgct   600
aatagtgggt ctttctgcat cattatcttc tccttgttga ttgtttccta tggtgtcatc   660
ctcttctctc taagaggtca cagctcagaa ggacgaagga agctctctc aacctgtgga   720
tcccatatta ctgttatgat attattcttt gtcccatgta tgctaatata tgcacggcct   780
tcatctgcct tttccttttga gaaaaacaca cttatatttg cctctgtcct gacaccattg   840
ttcaatccta tggtttacac tttcagaaat aaagaaatga gaatgccat caggaaaatg   900
tgtaggaaaa tgttagtaga ttctgataac ttttaa                              936
```

<210> SEQ ID NO 20
<211> LENGTH: 311
<212> TYPE: PRT
<213> ORGANISM: Murine sp.

<400> SEQUENCE: 20

```
Met Gln Asn Gln Ser Phe Val Thr Glu Phe Ile Leu Leu Gly Leu Ser
  1               5                  10                  15
```

```
Gln Asn Pro Lys Val Glu Lys Ile Leu Phe Val Phe Leu Leu Val
                20                  25                  30
Tyr Ile Ala Thr Ile Gly Gly Asn Met Ile Val Thr Ile Ile
         35                  40                  45
Tyr Ser Pro Ala Leu Leu Ser Ser Pro Met Tyr Phe Leu Ile Phe
     50                  55                  60
Leu Ser Phe Leu Asp Ala Cys Thr Ser Thr Val Thr Pro Lys Met
 65                  70                  75                  80
Ile Val Asp Phe Phe Tyr Glu Arg Lys Thr Ile Ser Phe Glu Cys Cys
                 85                  90                  95
Ile Thr Gln Leu Phe Thr Ser His Phe Phe Ala Gly Val Glu Val Ile
                100                 105                 110
Ile Leu Thr Ser Met Ala Tyr Asp Arg Tyr Val Ala Ile Cys Lys Pro
                115                 120                 125
Leu His Tyr Ser Ser Ile Met Thr Arg Arg Leu Cys Gly Thr Leu Val
                130                 135                 140
Met Val Ala Trp Thr Gly Gly Phe Leu His Ser Ile Thr Gln Val Ile
145                 150                 155                 160
Phe Thr Leu Gln Leu Pro Phe Cys Gly Pro Asn Phe Ile Asp His Phe
                165                 170                 175
Ile Cys Asp Leu Phe Pro Leu Leu Gln Leu Ala Cys Thr Asp Thr His
                180                 185                 190
Ile Phe Val Ile Leu Val Phe Ala Asn Ser Gly Ser Phe Cys Ile Ile
                195                 200                 205
Ile Phe Ser Leu Leu Ile Val Ser Tyr Gly Val Ile Leu Phe Ser Leu
                210                 215                 220
Arg Gly His Ser Ser Glu Gly Arg Arg Lys Ala Leu Ser Thr Cys Gly
225                 230                 235                 240
Ser His Ile Thr Val Met Ile Leu Phe Phe Val Pro Cys Met Leu Ile
                245                 250                 255
Tyr Ala Arg Pro Ser Ser Ala Phe Ser Phe Glu Lys Asn Thr Leu Ile
                260                 265                 270
Phe Ala Ser Val Leu Thr Pro Leu Phe Asn Pro Met Val Tyr Thr Phe
                275                 280                 285
Arg Asn Lys Glu Met Lys Asn Ala Ile Arg Lys Met Cys Arg Lys Met
                290                 295                 300
Leu Val Asp Ser Asp Asn Phe
305                 310

<210> SEQ ID NO 21
<211> LENGTH: 921
<212> TYPE: DNA
<213> ORGANISM: Murine sp.

<400> SEQUENCE: 21
atgggacaga accacaatgt cacagaattc atttttgtgg gtcttagtca agatcctgct      60
gggcaaaaag tattatttgt cttgttttca ctgacttaca ttgtgacaat gttcggaaac     120
ctgctcattg cacttacagt gattgccagc ccctccttaa actccccaat gtacttcttc     180
cttgcctgtc tgtcagtcct ggatgctctt tattgcaata caatctcacc aaatttgatt     240
atagacttgt tatataataa aaagaatatc tccttcagag cttgcatgct ccagctgttt     300
gtagagcact tatttggagg tgttgaggtc ttccttctgg tattcatggc ctatgatcgc     360
tatgtggcca tctgtaagcc actgcactat ttgaccatca tgaaccagag ggtgtgcatt     420
```

```
cttctattgc tgatagctgg agttggaggc atcttacact cactgattca agttctgact    480
gtgtataaac ttccttttg tggtcccaat gtcattgatc acttcatgtg tgacatgaat     540
caattactcg ggcttgcatg cactgacacc tacttccttg gcatcactgt catggccaat    600
ggtggagtaa tctgtgtggg aattttcacc tttctcttag tctcctatgg aatcattcta    660
aactctctta agacccacag tcgggaagga agacataaag ctctgtttac ctgcagttct    720
cacatcatgg ttgttgtctg cttttttgct ccctgtagtt ttatatatgc tagacctgtc    780
tccaactttc cagtggataa atatattgct gtgttttata cagttgttag tcccatgctg    840
aatccattga tatataccct gagaaattca gagatgaaaa actctattaa aaagctctgg    900
tgtaaaactc taacaacata a                                              921
```

<210> SEQ ID NO 22
<211> LENGTH: 240
<212> TYPE: PRT
<213> ORGANISM: Murine sp.

<400> SEQUENCE: 22

```
Met Gly Gln Asn His Asn Val Thr Glu Phe Ile Phe Val Gly Leu Ser
 1               5                  10                  15

Gln Asp Pro Ala Gly Gln Lys Val Leu Phe Val Leu Phe Ser Leu Thr
            20                  25                  30

Tyr Ile Val Thr Met Phe Gly Asn Leu Leu Ile Ala Leu Thr Val Ile
        35                  40                  45

Ala Ser Pro Ser Leu Asn Ser Pro Met Tyr Phe Phe Leu Ala Cys Leu
    50                  55                  60

Ser Val Leu Asp Ala Leu Tyr Cys Asn Thr Ile Ser Pro Asn Leu Ile
65                  70                  75                  80

Ile Asp Leu Leu Tyr Asn Lys Lys Asn Ile Ser Phe Arg Ala Cys Met
                85                  90                  95

Leu Gln Leu Phe Val Glu His Leu Phe Gly Gly Val Glu Val Phe Leu
            100                 105                 110

Leu Val Phe Met Ala Tyr Asp Arg Tyr Val Ala Ile Cys Lys Pro Leu
        115                 120                 125

His Tyr Leu Thr Ile Met Asn Gln Arg Val Cys Ile Leu Leu Leu Leu
    130                 135                 140

Ile Ala Gly Val Gly Gly Ile Leu His Ser Leu Ile Gln Val Leu Thr
145                 150                 155                 160

Val Tyr Lys Leu Pro Phe Cys Gly Pro Asn Val Ile Asp His Phe Met
                165                 170                 175

Cys Asp Met Asn Gln Leu Leu Gly Leu Ala Cys Thr Asp Thr Tyr Phe
            180                 185                 190

Leu Gly Ile Thr Val Met Ala Asn Gly Gly Val Ile Cys Val Gly Ile
        195                 200                 205

Phe Thr Phe Leu Leu Val Ser Tyr Gly Ile Ile Leu Asn Ser Leu Lys
    210                 215                 220

Thr His Ser Arg Glu Gly Arg His Lys Ala Leu Phe Thr Cys Ser Ser
225                 230                 235                 240
```

<210> SEQ ID NO 23
<211> LENGTH: 993
<212> TYPE: DNA
<213> ORGANISM: Homo sapiens

<400> SEQUENCE: 23

```
atgtgttctt ttttcttgtg ccaaacaggt aaacaggcaa aaatatcaat gggagaagaa      60
aaccaaacct tgtgtccaa gtttatcttc ctgggtcttt cacaggactt gcagacccag     120
atcctgctat ttatccttt cctcatcatt tatctgctga ccgtgcttgg aaaccagctc     180
atcatcattc tcatcttcct ggattctcgc cttcacactc ccatgtattt ttttcttaga     240
aatctctcct ttgcagatct ctgtttctct actagcattg tccctcaagt gttggttcac     300
ttcttggtaa agaggaaaac catttctttt tatgggtgta tgacacagat aattgtcttt     360
cttctggttg ggtgtacaga gtgtgcgctg ctggcagtga tgtcctatga ccggtatgtg     420
gctgtctgca agcccctgta ctactctacc atcatgacac aacgggtgtg tctctggctg     480
tccttcaggt cctgggccag tggggcacta gtgtctttag tagataccag ctttactttc     540
catcttccct actggggaca gaatataatc aatcactact tttgtgaacc tcctgccctc     600
ctgaagctgg cttccataga cacttacagc acagaaatgg ccatcttttc aatgggcgtg     660
gtaatcctcc tggcccctgt ctccctgatt cttggttctt attggaatat tatctccact     720
gttatccaga tgcagtctgg ggaagggaga ctcaaggctt tttccacctg tggctcccat     780
cttattgttg ttgtcctctt ctatgggtca ggaatattca cctacatgcg accaaactcc     840
aagactacaa agaactgga taaaatgata tctgtgttct atacagcggt gactccaatg     900
ttgaacccca taatttatag cttgaggaac aaagatgtca aaggggctct caggaaacta     960
gttgggagaa agtgcttctc tcataggcag tga                                 993
```

<210> SEQ ID NO 24
<211> LENGTH: 330
<212> TYPE: PRT
<213> ORGANISM: Homo sapiens

<400> SEQUENCE: 24

```
Met Cys Ser Phe Phe Leu Cys Gln Thr Gly Lys Gln Ala Lys Ile Ser
  1               5                  10                  15

Met Gly Glu Glu Asn Gln Thr Phe Val Ser Lys Phe Ile Phe Leu Gly
             20                  25                  30

Leu Ser Gln Asp Leu Gln Thr Gln Ile Leu Leu Phe Ile Leu Phe Leu
         35                  40                  45

Ile Ile Tyr Leu Leu Thr Val Leu Gly Asn Gln Leu Ile Ile Ile Leu
     50                  55                  60

Ile Phe Leu Asp Ser Arg Leu His Thr Pro Met Tyr Phe Phe Leu Arg
 65                  70                  75                  80

Asn Leu Ser Phe Ala Asp Leu Cys Phe Ser Thr Ser Ile Val Pro Gln
                 85                  90                  95

Val Leu Val His Phe Leu Val Lys Arg Lys Thr Ile Ser Phe Tyr Gly
            100                 105                 110

Cys Met Thr Gln Ile Ile Val Phe Leu Leu Val Gly Cys Thr Glu Cys
        115                 120                 125

Ala Leu Leu Ala Val Met Ser Tyr Asp Arg Tyr Val Ala Val Cys Lys
    130                 135                 140

Pro Leu Tyr Tyr Ser Thr Ile Met Thr Gln Arg Val Cys Leu Trp Leu
145                 150                 155                 160

Ser Phe Arg Ser Trp Ala Ser Gly Ala Leu Val Ser Leu Val Asp Thr
                165                 170                 175

Ser Phe Thr Phe His Leu Pro Tyr Trp Gly Gln Asn Ile Ile Asn His
            180                 185                 190
```

```
Tyr Phe Cys Glu Pro Pro Ala Leu Leu Lys Leu Ala Ser Ile Asp Thr
            195                 200                 205

Tyr Ser Thr Glu Met Ala Ile Phe Ser Met Gly Val Val Ile Leu Leu
        210                 215                 220

Ala Pro Val Ser Leu Ile Leu Gly Ser Tyr Trp Asn Ile Ile Ser Thr
225                 230                 235                 240

Val Ile Gln Met Gln Ser Gly Glu Gly Arg Leu Lys Ala Phe Ser Thr
                245                 250                 255

Cys Gly Ser His Leu Ile Val Val Leu Phe Tyr Gly Ser Gly Ile
                260                 265                 270

Phe Thr Tyr Met Arg Pro Asn Ser Lys Thr Thr Lys Glu Leu Asp Lys
            275                 280                 285

Met Ile Ser Val Phe Tyr Thr Ala Val Thr Pro Met Leu Asn Pro Ile
        290                 295                 300

Ile Tyr Ser Leu Arg Asn Lys Asp Val Lys Gly Ala Leu Arg Lys Leu
305                 310                 315                 320

Val Gly Arg Lys Cys Phe Ser His Arg Gln
                325                 330

<210> SEQ ID NO 25
<211> LENGTH: 951
<212> TYPE: DNA
<213> ORGANISM: Homo sapiens

<400> SEQUENCE: 25
atggagctct ggaacttcac cttgggaagt ggcttcattt tggtggggat tctgaatgac      60
agtgggtctc ctgaactgct ctgtgctaca attacaatcc tatacttgtt ggccctgatc     120
agcaatggcc tactgctcct ggctatcacc atggaagccc ggctccacat gcccatgtac     180
ctcctgcttg gcagctctc tctcatggac ctcctgttca catctgttgt cactcccaag     240
gcccttgcgg actttctgcg cagagaaaac accatctcct tggaggctg tgcccttcag     300 atgttcctgg cactgacaat gggtggtgct gaggacctcc tactggcctt catggcctat     360
gacaggtatg tggccatttg tcatcctctg acatacatga ccctcatgag ctcaagagcc     420
tgctggctca tggtggccac gtcctggatc ctggcatccc taagtgccct aatatatacc     480
gtgtatacca tgcactatcc cttctgcagg gcccaggaga tcaggcatct ctctctgtgag     540 atcccacact tgctgaaggt ggcctgtgct gatacctcca gatatgagct catggtatat     600
gtgatgggtg tgaccttcct gattccctct cttgctgcta tactggcctc ctatacacaa     660
attctactca ctgtgctcca tatgccatca aatgagggga ggaagaaagc ccttgtcacc     720
tgctcttccc acctgactgt ggttgggatg ttctatggag ctgccacatt catgtatgtc     780
ttgcccagtt ccttccacag caccagacaa gacaacatca tctctgtttt ctacacaatt     840
gtcactccag ccctgaatcc actcatctac agcctgagga taaggaggt catgcgggcc     900 ttgaggaggg tcctgggaaa atacatgctg ccagcacact ccacgctcta g             951

<210> SEQ ID NO 26
<211> LENGTH: 316
<212> TYPE: PRT
<213> ORGANISM: Homo sapiens

<400> SEQUENCE: 26

Met Glu Leu Trp Asn Phe Thr Leu Gly Ser Gly Phe Ile Leu Val Gly
  1               5                  10                  15

Ile Leu Asn Asp Ser Gly Ser Pro Glu Leu Leu Cys Ala Thr Ile Thr
```

-continued

```
                 20                  25                  30

Ile Leu Tyr Leu Leu Ala Leu Ile Ser Asn Gly Leu Leu Leu Ala
         35                  40                  45

Ile Thr Met Glu Ala Arg Leu His Met Pro Met Tyr Leu Leu Gly
 50                  55                  60

Gln Leu Ser Leu Met Asp Leu Leu Phe Thr Ser Val Val Thr Pro Lys
 65                  70                  75                  80

Ala Leu Ala Asp Phe Leu Arg Arg Glu Asn Thr Ile Ser Phe Gly Gly
                 85                  90                  95

Cys Ala Leu Gln Met Phe Leu Ala Leu Thr Met Gly Gly Ala Glu Asp
                100                 105                 110

Leu Leu Leu Ala Phe Met Ala Tyr Asp Arg Tyr Val Ala Ile Cys His
                115                 120                 125

Pro Leu Thr Tyr Met Thr Leu Met Ser Ser Arg Ala Cys Trp Leu Met
                130                 135                 140

Val Ala Thr Ser Trp Ile Leu Ala Ser Leu Ser Ala Leu Ile Tyr Thr
145                 150                 155                 160

Val Tyr Thr Met His Tyr Pro Phe Cys Arg Ala Gln Glu Ile Arg His
                165                 170                 175

Leu Leu Cys Glu Ile Pro His Leu Leu Lys Val Ala Cys Ala Asp Thr
                180                 185                 190

Ser Arg Tyr Glu Leu Met Val Tyr Val Met Gly Val Thr Phe Leu Ile
                195                 200                 205

Pro Ser Leu Ala Ala Ile Leu Ala Ser Tyr Thr Gln Ile Leu Leu Thr
                210                 215                 220

Val Leu His Met Pro Ser Asn Glu Gly Arg Lys Lys Ala Leu Val Thr
225                 230                 235                 240

Cys Ser Ser His Leu Thr Val Val Gly Met Phe Tyr Gly Ala Ala Thr
                245                 250                 255

Phe Met Tyr Val Leu Pro Ser Ser Phe His Ser Thr Arg Gln Asp Asn
                260                 265                 270

Ile Ile Ser Val Phe Tyr Thr Ile Val Thr Pro Ala Leu Asn Pro Leu
                275                 280                 285

Ile Tyr Ser Leu Arg Asn Lys Glu Val Met Arg Ala Leu Arg Arg Val
                290                 295                 300

Leu Gly Lys Tyr Met Leu Pro Ala His Ser Thr Leu
305                 310                 315

<210> SEQ ID NO 27
<211> LENGTH: 948
<212> TYPE: DNA
<213> ORGANISM: Homo sapiens
<220> FEATURE:
<221> NAME/KEY: modified_base
<222> LOCATION: (9)..(12)
<223> OTHER INFORMATION: a, t, c, g, other or unknown
<220> FEATURE:
<221> NAME/KEY: modified_base
<222> LOCATION: (21)
<223> OTHER INFORMATION: a, t, c, g, other or unknown
<220> FEATURE:
<221> NAME/KEY: modified_base
<222> LOCATION: (64)..(66)
<223> OTHER INFORMATION: a, t, c, g, other or unknown
<220> FEATURE:
<221> NAME/KEY: modified_base
<222> LOCATION: (100)..(105)
<223> OTHER INFORMATION: a, t, c, g, other or unknown
<220> FEATURE:
<221> NAME/KEY: modified_base
```

```
<222> LOCATION: (132)
<223> OTHER INFORMATION: a, t, c, g, other or unknown
<220> FEATURE:
<221> NAME/KEY: modified_base
<222> LOCATION: (155)..(156)
<223> OTHER INFORMATION: a, t, c, g, other or unknown
<220> FEATURE:
<221> NAME/KEY: modified_base
<222> LOCATION: (432)..(433)
<223> OTHER INFORMATION: a, t, c, g, other or unknown
<220> FEATURE:
<221> NAME/KEY: modified_base
<222> LOCATION: (435)..(436)
<223> OTHER INFORMATION: a, t, c, g, other or unknown
<220> FEATURE:
<221> NAME/KEY: modified_base
<222> LOCATION: (505)
<223> OTHER INFORMATION: a, t, c, g, other or unknown

<400> SEQUENCE: 27
atgagacann nnaacaatat nacagaattt gtcctcctgg gcttttctca ggatcctggt        60
gtgnnnaaag cattatttgt catgttttta ctcacatacn nnnnnacagt ggtggggaac       120
ctgctcattg tngtggatat tattgccagc ccttnnttgg gttccccaat gtatttcttc       180
cttgcctgcc tgtcatttat agatgctgca tattccacta ccatttctcc caagttaatt       240
gtaggcttat tctgtgataa aaagactatt tccttccaag gttgcatggg ccagctattt       300
atagaccatt tctttggtgg ggctgaggtc ttccttctgg tggtgatggc ctgtgatcgc       360
tatgtggcca tctgtaagcc actgcactat ttgaccatca tgaatcgaca ggtttgcttc       420
cttctgttgg tnntnnccat gattggaggt tttgtacatt ctgcgtttca aattgttgtg       480
tacagtctcc ctttctgtgg tcccnatgtc attgttcatt tcagttgtga catgcaccca       540
ttactggaac tggcatgcac tgacacctac tttataggcc tcactgttgt tgtcaatagt       600
ggagcaatct gtatggtcat tttcaacctt ctgttaatct cctatggagt catcctaagc       660
tcccttaaaa cttacagtca ggaaaagagg ggtaaagcct tgtctacctg cagctccggc       720
agtaccgttg ttgtcctctt ttttgtaccc tgtattttca tatatgttag acctgtttca       780
aactttccta ctgataagtt catgactgtg ttttatacca ttatcacaca catgctgagt       840
cctttaatat atacgttgag aaattcagag atgagaaatg ctatagaaaa actcttgggt       900
aaaaagttaa ctatatttat tataggagga gtgtccgtcc tcatgtag                    948

<210> SEQ ID NO 28
<211> LENGTH: 315
<212> TYPE: PRT
<213> ORGANISM: Homo sapiens
<220> FEATURE:
<221> NAME/KEY: MOD_RES
<222> LOCATION: (3)..(4)
<223> OTHER INFORMATION: Varible amino acid
<220> FEATURE:
<221> NAME/KEY: MOD_RES
<222> LOCATION: (7)
<223> OTHER INFORMATION: Varible amino acid
<220> FEATURE:
<221> NAME/KEY: MOD_RES
<222> LOCATION: (22)
<223> OTHER INFORMATION: Varible amino acid
<220> FEATURE:
<221> NAME/KEY: MOD_RES
<222> LOCATION: (34)..(35)
<223> OTHER INFORMATION: Varible amino acid
<220> FEATURE:
<221> NAME/KEY: MOD_RES
<222> LOCATION: (52)
<223> OTHER INFORMATION: Varible amino acid
<220> FEATURE:
```

<221> NAME/KEY: MOD_RES
<222> LOCATION: (145)..(146)
<223> OTHER INFORMATION: Varible amino acid
<220> FEATURE:
<221> NAME/KEY: MOD_RES
<222> LOCATION: (169)
<223> OTHER INFORMATION: Varible amino acid

<400> SEQUENCE: 28

Met Arg Xaa Xaa Asn Asn Xaa Thr Glu Phe Val Leu Leu Gly Phe Ser
1               5                   10                  15

Gln Asp Pro Gly Val Xaa Lys Ala Leu Phe Val Met Phe Leu Leu Thr
            20                  25                  30

Tyr Xaa Xaa Thr Val Val Gly Asn Leu Leu Ile Val Val Asp Ile Ile
        35                  40                  45

Ala Ser Pro Xaa Leu Gly Ser Pro Met Tyr Phe Leu Ala Cys Leu
    50                  55                  60

Ser Phe Ile Asp Ala Ala Tyr Ser Thr Thr Ile Ser Pro Lys Leu Ile
65                  70                  75                  80

Val Gly Leu Phe Cys Asp Lys Lys Thr Ile Ser Phe Gln Gly Cys Met
                85                  90                  95

Gly Gln Leu Phe Ile Asp His Phe Phe Gly Gly Ala Glu Val Phe Leu
            100                 105                 110

Leu Val Val Met Ala Cys Asp Arg Tyr Val Ala Ile Cys Lys Pro Leu
        115                 120                 125

His Tyr Leu Thr Ile Met Asn Arg Gln Val Cys Phe Leu Leu Leu Val
    130                 135                 140

Xaa Xaa Met Ile Gly Gly Phe Val His Ser Ala Phe Gln Ile Val Val
145                 150                 155                 160

Tyr Ser Leu Pro Phe Cys Gly Pro Xaa Val Ile Val His Phe Ser Cys
                165                 170                 175

Asp Met His Pro Leu Leu Glu Leu Ala Cys Thr Asp Thr Tyr Phe Ile
            180                 185                 190

Gly Leu Thr Val Val Val Asn Ser Gly Ala Ile Cys Met Val Ile Phe
        195                 200                 205

Asn Leu Leu Leu Ile Ser Tyr Gly Val Ile Leu Ser Ser Leu Lys Thr
210                 215                 220

Tyr Ser Gln Glu Lys Arg Gly Lys Ala Leu Ser Thr Cys Ser Ser Gly
225                 230                 235                 240

Ser Thr Val Val Val Leu Phe Phe Val Pro Cys Ile Phe Ile Tyr Val
                245                 250                 255

Arg Pro Val Ser Asn Phe Pro Thr Asp Lys Phe Met Thr Val Phe Tyr
            260                 265                 270

Thr Ile Ile Thr His Met Leu Ser Pro Leu Ile Tyr Thr Leu Arg Asn
        275                 280                 285

Ser Glu Met Arg Asn Ala Ile Glu Lys Leu Leu Gly Lys Lys Leu Thr
    290                 295                 300

Ile Phe Ile Ile Gly Gly Val Ser Val Leu Met
305                 310                 315

<210> SEQ ID NO 29
<211> LENGTH: 939
<212> TYPE: DNA
<213> ORGANISM: Homo sapiens

<400> SEQUENCE: 29
atggaacaac acaatctaac aacggtgaat gaattcattc ttacgggaat cacagatatc      60

```
gctgagctgc aggcaccatt atttgcattg ttcctcatga tctatgtgat ctcagtgatg    120
ggcaatttgg gcatgattgt cctcaccaag ttggactcca ggttgcaaac ccctatgtac    180 tttttttctca gacatctggc tttcatggat cttggttatt caacaactgt gggacccaaa   240
atgttagtaa attttgttgt ggataagaat ataatttctt attattttg tgcaacacag    300 ctagctttct ttcttgtgtt cattggtagt gaactttta ttctctcagc catgtcctac     360
gacctctatg tggccatctg taaccctctg ctatacacag taatcatgtc acgaagggta    420
tgtcaggtgc tggtagcaat cccttacctc tattgcacat tcatttctct tctagtcacc    480
ataaagattt ttactttatc cttctgtggc tacaacgtca ttagtcattt ctactgtgac    540
agtctccctt tgttaccttt gctttgttca aatacacatg aaattgaatt gataattctg    600
atctttgcag ctattgattt gatttcatct cttctgatag ttcttttatc ttacctgctc    660
atccttgtag ccattctcag gatgaattct gctggcagac aaaaggcttt ttctacctgt    720
ggagcccacc tgacagtggt catagtgttc tatgggactt tgcttttcat gtacgtgcag    780
cccaagtcca gtcattcctt tgacactgat aaagtggctt ccatatttta caccctggtt    840
atccccatgt tgaatccctt gatctatagt ttacgaaaca aagatgtaaa atatgccta     900 cgaaggacat ggaataactt atgtaatatt tttgtttaa                           939
```

<210> SEQ ID NO 30
<211> LENGTH: 312
<212> TYPE: PRT
<213> ORGANISM: Homo sapiens

<400> SEQUENCE: 30

```
Met Glu Gln His Asn Leu Thr Thr Val Asn Glu Phe Ile Leu Thr Gly
 1               5                  10                  15

Ile Thr Asp Ile Ala Glu Leu Gln Ala Pro Leu Phe Ala Leu Phe Leu
                20                  25                  30

Met Ile Tyr Val Ile Ser Val Met Gly Asn Leu Gly Met Ile Val Leu
            35                  40                  45

Thr Lys Leu Asp Ser Arg Leu Gln Thr Pro Met Tyr Phe Phe Leu Arg
     50                  55                  60

His Leu Ala Phe Met Asp Leu Gly Tyr Ser Thr Thr Val Gly Pro Lys
 65                  70                  75                  80

Met Leu Val Asn Phe Val Val Asp Lys Asn Ile Ile Ser Tyr Tyr Phe
                 85                  90                  95

Cys Ala Thr Gln Leu Ala Phe Phe Leu Val Phe Ile Gly Ser Glu Leu
            100                 105                 110

Phe Ile Leu Ser Ala Met Ser Tyr Asp Leu Tyr Val Ala Ile Cys Asn
        115                 120                 125

Pro Leu Leu Tyr Thr Val Ile Met Ser Arg Arg Val Cys Gln Val Leu
    130                 135                 140

Val Ala Ile Pro Tyr Leu Tyr Cys Thr Phe Ile Ser Leu Leu Val Thr
145                 150                 155                 160

Ile Lys Ile Phe Thr Leu Ser Phe Cys Gly Tyr Asn Val Ile Ser His
                165                 170                 175

Phe Tyr Cys Asp Ser Leu Pro Leu Leu Pro Leu Leu Cys Ser Asn Thr
            180                 185                 190

His Glu Ile Glu Leu Ile Ile Leu Ile Phe Ala Ala Ile Asp Leu Ile
        195                 200                 205

Ser Ser Leu Leu Ile Val Leu Leu Ser Tyr Leu Leu Ile Leu Val Ala
```

```
                210                 215                 220
Ile Leu Arg Met Asn Ser Ala Gly Arg Gln Lys Ala Phe Ser Thr Cys
225                 230                 235                 240

Gly Ala His Leu Thr Val Val Ile Val Phe Tyr Gly Thr Leu Leu Phe
                245                 250                 255

Met Tyr Val Gln Pro Lys Ser Ser His Ser Phe Asp Thr Asp Lys Val
                260                 265                 270

Ala Ser Ile Phe Tyr Thr Leu Val Ile Pro Met Leu Asn Pro Leu Ile
                275                 280                 285

Tyr Ser Leu Arg Asn Lys Asp Val Lys Tyr Ala Leu Arg Arg Thr Trp
290                 295                 300

Asn Asn Leu Cys Asn Ile Phe Val
305                 310

<210> SEQ ID NO 31
<211> LENGTH: 312
<212> TYPE: PRT
<213> ORGANISM: Homo sapiens

<400> SEQUENCE: 31

Met Glu Ala Glu Asn Leu Thr Glu Leu Ser Lys Phe Leu Leu Leu Gly
  1               5                  10                  15

Leu Ser Asp Asp Pro Glu Leu Gln Pro Val Leu Phe Gly Leu Phe Leu
                 20                  25                  30

Ser Met Tyr Leu Val Thr Val Leu Gly Asn Leu Leu Ile Ile Leu Ala
                 35                  40                  45

Val Ser Ser Asp Ser His Leu His Thr Pro Met Tyr Phe Phe Leu Ser
     50                  55                  60

Asn Leu Ser Phe Val Asp Ile Cys Phe Ile Ser Thr Thr Val Pro Lys
 65                  70                  75                  80

Met Leu Val Ser Ile Gln Ala Arg Ser Lys Asp Ile Ser Tyr Met Gly
                 85                  90                  95

Cys Leu Thr Gln Val Tyr Phe Leu Met Met Phe Ala Gly Met Asp Thr
                100                 105                 110

Phe Leu Leu Ala Val Met Ala Tyr Asp Arg Phe Val Ala Ile Cys His
                115                 120                 125

Pro Leu His Tyr Thr Val Ile Met Asn Pro Cys Leu Cys Gly Leu Leu
                130                 135                 140

Val Leu Ala Ser Trp Phe Ile Phe Trp Phe Ser Leu Val His Ile
145                 150                 155                 160

Leu Leu Met Lys Arg Leu Thr Phe Ser Thr Gly Thr Glu Ile Pro His
                165                 170                 175

Phe Phe Cys Glu Pro Ala Gln Val Leu Lys Val Ala Cys Ser Asn Thr
                180                 185                 190

Leu Leu Asn Asn Ile Val Leu Tyr Val Ala Thr Ala Leu Leu Gly Val
                195                 200                 205

Phe Pro Val Ala Gly Ile Leu Phe Ser Tyr Ser Gln Ile Val Ser Ser
                210                 215                 220

Leu Met Gly Met Ser Ser Thr Lys Gly Lys Tyr Lys Ala Phe Ser Thr
225                 230                 235                 240

Cys Gly Ser His Leu Cys Val Val Ser Leu Phe Tyr Gly Thr Gly Leu
                245                 250                 255

Gly Val Tyr Leu Ser Ser Ala Val Thr His Ser Ser Gln Ser Ser Ser
                260                 265                 270
```

```
Thr Ala Ser Val Met Tyr Ala Met Val Thr Pro Met Leu Asn Pro Phe
            275                 280                 285

Ile Tyr Ser Leu Arg Asn Lys Asp Val Lys Gly Ala Leu Glu Arg Leu
        290                 295                 300

Leu Ser Arg Ala Asp Ser Cys Pro
305                 310

<210> SEQ ID NO 32
<211> LENGTH: 314
<212> TYPE: PRT
<213> ORGANISM: Homo sapiens

<400> SEQUENCE: 32

Met Gly Glu Glu Asn Gln Thr Phe Val Ser Lys Phe Ile Phe Leu Gly
1               5                   10                  15

Leu Ser Gln Asp Leu Gln Thr Gln Ile Leu Leu Phe Ile Leu Phe Leu
            20                  25                  30

Ile Ile Tyr Leu Leu Thr Val Leu Gly Asn Gln Leu Ile Ile Ile Leu
        35                  40                  45

Ile Phe Leu Asp Ser Arg Leu His Thr Pro Met Tyr Phe Phe Leu Arg
    50                  55                  60

Asn Leu Ser Phe Ala Asp Leu Cys Phe Ser Thr Ser Ile Val Pro Gln
65                  70                  75                  80

Val Leu Val His Phe Leu Val Lys Arg Lys Thr Ile Ser Phe Tyr Gly
                85                  90                  95

Cys Met Thr Gln Ile Ile Val Phe Leu Leu Val Gly Cys Thr Glu Cys
            100                 105                 110

Ala Leu Leu Ala Val Met Ser Tyr Asp Arg Tyr Val Ala Val Cys Lys
        115                 120                 125

Pro Leu Tyr Tyr Ser Thr Ile Met Thr Gln Arg Val Cys Leu Trp Leu
    130                 135                 140

Ser Phe Arg Ser Trp Ala Ser Gly Ala Leu Val Ser Leu Val Asp Thr
145                 150                 155                 160

Ser Phe Thr Phe His Leu Pro Tyr Trp Gly Gln Asn Ile Ile Asn His
                165                 170                 175

Tyr Phe Cys Glu Pro Pro Ala Leu Leu Lys Leu Ala Ser Ile Asp Thr
            180                 185                 190

Tyr Ser Thr Glu Met Ala Ile Phe Ser Met Gly Val Val Ile Leu Leu
        195                 200                 205

Ala Pro Val Ser Leu Ile Leu Gly Ser Tyr Trp Asn Ile Ile Ser Thr
    210                 215                 220

Val Ile Gln Met Gln Ser Gly Glu Gly Arg Leu Lys Ala Phe Ser Thr
225                 230                 235                 240

Cys Gly Ser His Leu Ile Val Val Leu Phe Tyr Gly Ser Gly Ile
                245                 250                 255

Phe Thr Tyr Met Arg Pro Asn Ser Lys Thr Thr Lys Glu Leu Asp Lys
            260                 265                 270

Met Ile Ser Val Phe Tyr Thr Ala Val Thr Pro Met Leu Asn Pro Ile
        275                 280                 285

Ile Tyr Ser Leu Arg Asn Lys Asp Val Lys Gly Ala Leu Arg Lys Leu
    290                 295                 300

Val Gly Arg Lys Cys Phe Ser His Arg Gln
305                 310

<210> SEQ ID NO 33
```

```
<211> LENGTH: 318
<212> TYPE: PRT
<213> ORGANISM: Murine sp.

<400> SEQUENCE: 33

Met Glu Thr Gly Asn Asp Thr Gln Leu Ser Glu Phe Phe Leu Leu Gly
1               5                   10                  15

Phe Ser Glu Asn Gln Pro Gln Ile Gln Pro Val Ile Phe Gly Leu Phe
                20                  25                  30

Leu Phe Met Tyr Ile Leu Thr Phe Thr Gly Asn Leu Leu Ile Ile Met
            35                  40                  45

Ala Ile Ile Val Asp Ser His Leu His Thr Pro Met Tyr Leu Phe Phe
        50                  55                  60

Ser Asn Leu Ser Phe Val Asp Ile Cys Phe Thr Ser Thr Thr Val Pro
65                  70                  75                  80

Gln Met Leu Val Asn Ile His Thr Gln Ser Lys Ala Ile Thr Tyr Ala
                85                  90                  95

Gly Cys Ile Ile Gln Met Tyr Phe Leu Leu Leu Phe Ser Gly Leu Asp
            100                 105                 110

Ile Phe Leu Leu Thr Val Met Ala Tyr Asp Arg Tyr Val Ala Ile Cys
        115                 120                 125

His Pro Leu His Tyr Met Ile Met Ser Thr Arg Arg Cys Gly Leu Met
130                 135                 140

Ile Leu Ala Cys Trp Ile Ile Gly Val Ile Asn Ser Leu Leu His Thr
145                 150                 155                 160

Phe Leu Val Leu Arg Leu Ser Phe Cys Thr Asn Leu Glu Ile Pro His
                165                 170                 175

Phe Phe Cys Glu Leu Asn Gln Val Val His Gln Ala Cys Ser Asp Thr
            180                 185                 190

Phe Leu Asn Asp Met Val Ile Tyr Ile Thr Ala Met Leu Leu Ala Val
        195                 200                 205

Gly Pro Phe Ser Gly Ile Leu Tyr Ser Tyr Ser Arg Ile Val Ser Ser
210                 215                 220

Ile Cys Ala Ile Ser Ser Val Gln Gly Lys Tyr Lys Ala Phe Ser Thr
225                 230                 235                 240

Cys Ala Ser His Leu Ser Val Val Ser Leu Phe Tyr Cys Thr Leu Leu
                245                 250                 255

Gly Val Tyr Leu Ser Ser Ala Val Thr Gln Asn Ser His Ala Thr Ala
            260                 265                 270

Thr Ala Ser Leu Met Tyr Thr Val Val Thr Pro Met Leu Asn Pro Phe
        275                 280                 285

Ile Tyr Ser Leu Arg Asn Lys Asp Ile Lys Thr Ala Leu Lys Ile Leu
        290                 295                 300

Leu Gly Ser Val Thr Arg Ser Arg Ser Met Asp Ser Pro Ser
305                 310                 315

<210> SEQ ID NO 34
<211> LENGTH: 310
<212> TYPE: PRT
<213> ORGANISM: Homo sapiens

<400> SEQUENCE: 34

Met Asn Trp Val Asn Lys Ser Val Pro Gln Glu Phe Ile Leu Leu Val
1               5                   10                  15

Phe Ser Asp Gln Pro Trp Leu Glu Ile Pro Pro Phe Val Met Phe Leu
                20                  25                  30
```

```
Phe Ser Tyr Ile Leu Thr Ile Phe Gly Asn Leu Thr Ile Ile Leu Val
            35                  40                  45

Ser His Val Asp Phe Lys Leu His Thr Pro Met Tyr Phe Phe Leu Ser
 50                  55                  60

Asn Leu Ser Leu Leu Asp Leu Cys Tyr Thr Thr Ser Thr Val Pro Gln
 65                  70                  75                  80

Met Leu Val Asn Ile Cys Asn Thr Arg Lys Val Ile Ser Tyr Gly Gly
                 85                  90                  95

Cys Val Ala Gln Leu Phe Ile Phe Leu Ala Leu Gly Ser Thr Glu Cys
                100                 105                 110

Leu Leu Leu Ala Val Met Cys Phe Asp Arg Phe Val Ala Ile Cys Arg
            115                 120                 125

Pro Leu His Tyr Ser Ile Ile Met His Gln Arg Leu Cys Phe Gln Leu
            130                 135                 140

Ala Ala Ala Ser Trp Ile Ser Gly Phe Ser Asn Ser Val Leu Gln Ser
145                 150                 155                 160

Thr Trp Thr Leu Lys Met Pro Leu Cys Gly His Lys Glu Val Asp His
                165                 170                 175

Phe Phe Cys Glu Val Pro Ala Leu Leu Lys Leu Ser Cys Val Asp Thr
                180                 185                 190

Thr Ala Asn Glu Ala Glu Leu Phe Phe Ile Ser Val Leu Phe Leu Leu
            195                 200                 205

Ile Pro Val Thr Leu Ile Leu Ile Ser Tyr Ala Phe Ile Val Gln Ala
            210                 215                 220

Val Leu Arg Ile Gln Ser Ala Glu Gly Gln Arg Lys Ala Phe Gly Thr
225                 230                 235                 240

Cys Gly Ser His Leu Ile Val Val Ser Leu Phe Tyr Gly Thr Ala Ile
                245                 250                 255

Ser Met Tyr Leu Gln Pro Pro Ser Pro Ser Ser Lys Asp Arg Gly Lys
                260                 265                 270

Met Val Ser Leu Phe Cys Gly Ile Ile Ala Pro Met Leu Asn Pro Leu
            275                 280                 285

Ile Tyr Thr Leu Arg Asn Lys Glu Val Lys Glu Ala Phe Lys Arg Leu
            290                 295                 300

Val Ala Lys Ser Leu Leu
305                 310

<210> SEQ ID NO 35
<211> LENGTH: 309
<212> TYPE: PRT
<213> ORGANISM: Homo sapiens

<400> SEQUENCE: 35

Met Lys Ser Trp Asn Asn Thr Ile Ile Leu Glu Phe Leu Leu Leu Gly
  1               5                  10                  15

Ile Ser Glu Glu Pro Glu Leu Gln Ala Phe Leu Phe Gly Leu Phe Leu
                 20                  25                  30

Ser Met Tyr Leu Val Thr Val Leu Gly Asn Leu Leu Ile Ile Leu Ala
            35                  40                  45

Thr Ile Ser Asp Ser His Leu His Thr Pro Met Tyr Phe Phe Leu Ser
 50                  55                  60

Asn Leu Ser Phe Val Asp Ile Cys Phe Ser Thr Thr Val Pro Lys
 65                  70                  75                  80

Met Leu Val Asn Ile Gln Thr His Asn Lys Val Ile Thr Tyr Ala Gly
```

```
                85                  90                  95
Cys Ile Thr Gln Met Cys Phe Phe Leu Leu Phe Val Gly Leu Asp Asn
            100                 105                 110

Phe Leu Leu Thr Val Met Ala Tyr Asp Arg Phe Val Ala Ile Cys His
            115                 120                 125

Pro Leu His Tyr Met Val Ile Met Asn Pro Gln Leu Cys Gly Leu Leu
            130                 135                 140

Val Leu Ala Ser Trp Ile Met Ser Val Leu Asn Ser Met Leu Gln Ser
145                 150                 155                 160

Leu Met Val Leu Pro Leu Pro Phe Cys Thr His Met Glu Ile Pro His
                165                 170                 175

Phe Phe Cys Glu Ile Asn Gln Val Val His Leu Ala Cys Ser Asp Thr
            180                 185                 190

Phe Leu Asn Asp Ile Val Met Tyr Phe Ala Val Ala Leu Leu Gly Gly
            195                 200                 205

Gly Pro Leu Thr Gly Ile Leu Tyr Ser Tyr Ser Lys Ile Val Ser Ser
            210                 215                 220

Ile Arg Ala Ile Ser Ser Ala Gln Gly Lys Tyr Lys Ala Phe Ser Thr
225                 230                 235                 240

Cys Ala Ser His Leu Ser Val Val Ser Leu Phe Tyr Gly Thr Cys Leu
                245                 250                 255

Gly Val Tyr Leu Ser Ser Ala Ala Thr His Asn Ser His Thr Gly Ala
            260                 265                 270

Ala Ala Ser Val Met Tyr Thr Val Thr Pro Met Leu Asn Pro Phe
            275                 280                 285

Ile Tyr Ser Leu Arg Asn Lys His Ile Lys Gly Ala Met Lys Thr Phe
290                 295                 300

Phe Arg Gly Lys Gln
305

<210> SEQ ID NO 36
<211> LENGTH: 313
<212> TYPE: PRT
<213> ORGANISM: Homo sapiens

<400> SEQUENCE: 36

Met Lys Arg Glu Asn Gln Ser Ser Val Ser Glu Phe Leu Leu Leu Asp
  1               5                  10                  15

Leu Pro Ile Trp Pro Glu Gln Gln Ala Val Phe Phe Thr Leu Phe Leu
                 20                  25                  30

Gly Met Tyr Leu Ile Thr Val Leu Gly Asn Leu Leu Ile Ile Leu Leu
             35                  40                  45

Ile Arg Leu Asp Ser His Leu His Thr Pro Met Phe Phe Phe Leu Ser
         50                  55                  60

His Leu Ala Leu Thr Asp Ile Ser Leu Ser Ser Val Thr Val Pro Lys
 65                  70                  75                  80

Met Leu Leu Ser Met Gln Thr Gln Asp Gln Ser Ile Leu Tyr Ala Gly
                 85                  90                  95

Cys Val Thr Gln Met Tyr Phe Phe Ile Phe Phe Thr Asp Leu Asp Asn
            100                 105                 110

Phe Leu Leu Thr Ser Met Ala Tyr Asp Arg Tyr Val Ala Ile Cys His
            115                 120                 125

Pro Leu Arg Tyr Thr Thr Ile Met Lys Glu Gly Leu Cys Asn Leu Leu
            130                 135                 140
```

-continued

```
Val Thr Val Ser Trp Ile Leu Ser Cys Thr Asn Ala Leu Ser His Thr
145                 150                 155                 160

Leu Leu Leu Ala Gln Leu Ser Phe Cys Ala Asp Asn Thr Ile Pro His
                165                 170                 175

Phe Phe Cys Asp Leu Val Ala Leu Leu Lys Leu Ser Cys Ser Asp Ile
            180                 185                 190

Ser Leu Asn Glu Leu Val Ile Phe Thr Val Gly Gln Ala Val Ile Thr
        195                 200                 205

Leu Pro Leu Ile Cys Ile Leu Ile Ser Tyr Gly His Ile Gly Val Thr
    210                 215                 220

Ile Leu Lys Ala Pro Ser Thr Lys Gly Ile Phe Lys Ala Leu Ser Thr
225                 230                 235                 240

Cys Gly Ser His Leu Ser Val Val Ser Leu Tyr Tyr Gly Thr Ile Ile
                245                 250                 255

Gly Leu Tyr Phe Leu Pro Ser Ser Ser Ala Ser Ser Asp Lys Asp Val
                260                 265                 270

Ile Ala Ser Val Met Tyr Thr Val Ile Thr Pro Leu Leu Asn Pro Phe
            275                 280                 285

Ile Tyr Ser Leu Arg Asn Arg Asp Ile Lys Gly Ala Leu Glu Arg Leu
        290                 295                 300

Phe Asn Arg Ala Thr Val Leu Ser Gln
305                 310
```

<210> SEQ ID NO 37
<211> LENGTH: 314
<212> TYPE: PRT
<213> ORGANISM: Homo sapiens

<400> SEQUENCE: 37

```
Met Met Gly Gln Asn Gln Ile Ser Ile Ser Asp Phe Leu Leu Leu Gly
  1               5                  10                  15

Leu Pro Ile Gln Pro Glu Gln Gln Asn Leu Cys Tyr Ala Leu Phe Leu
                 20                  25                  30

Ala Met Tyr Leu Thr Thr Leu Leu Gly Asn Leu Leu Ile Ile Val Leu
             35                  40                  45

Ile Arg Leu Asp Ser His Leu His Thr Pro Met Tyr Leu Phe Leu Ser
 50                  55                  60

Asn Leu Ser Phe Ser Asp Leu Cys Phe Ser Ser Val Thr Ile Pro Lys
 65                  70                  75                  80

Leu Leu Gln Asn Met Gln Asn Gln Asp Pro Ser Ile Pro Tyr Ala Asp
                 85                  90                  95

Cys Leu Thr Gln Met Tyr Phe Phe Leu Leu Phe Gly Asp Leu Glu Ser
            100                 105                 110

Phe Leu Leu Val Ala Met Ala Tyr Asp Arg Tyr Val Ala Ile Cys Phe
        115                 120                 125

Pro Leu His Tyr Thr Ala Ile Met Ser Pro Met Leu Cys Leu Ala Leu
    130                 135                 140

Val Ala Leu Ser Trp Val Leu Thr Thr Phe His Ala Met Leu His Thr
145                 150                 155                 160

Leu Leu Met Ala Arg Leu Cys Phe Cys Ala Asp Asn Val Ile Pro His
                165                 170                 175

Phe Phe Cys Asp Met Ser Ala Leu Leu Lys Leu Ala Phe Ser Asp Thr
            180                 185                 190

Arg Val Asn Glu Trp Val Ile Phe Ile Met Gly Gly Leu Ile Leu Val
        195                 200                 205
```

-continued

Ile Pro Phe Leu Leu Ile Leu Gly Ser Tyr Ala Arg Thr Val Ser Ser
    210                 215                 220

Ile Leu Lys Val Pro Ser Ser Lys Gly Ile Cys Lys Ala Phe Ser Thr
225                 230                 235                 240

Cys Gly Ser His Leu Ser Val Val Ser Leu Phe Tyr Gly Thr Val Ile
                245                 250                 255

Gly Leu Tyr Leu Cys Ser Ser Ala Asn Ser Ser Thr Leu Lys Asp Thr
                260                 265                 270

Val Met Ala Met Met Tyr Thr Val Val Thr Pro Met Leu Asn Pro Phe
            275                 280                 285

Ile Tyr Ser Leu Arg Asn Arg Asp Met Lys Gly Ala Leu Ser Arg Val
    290                 295                 300

Ile His Gln Lys Lys Thr Phe Phe Ser Leu
305                 310

<210> SEQ ID NO 38
<211> LENGTH: 316
<212> TYPE: PRT
<213> ORGANISM: Homo sapiens

<400> SEQUENCE: 38

Met Gln Asn Gln Ser Phe Val Thr Glu Phe Val Leu Leu Gly Leu Ser
1               5                   10                  15

Gln Asn Pro Asn Val Gln Glu Ile Val Phe Val Val Phe Leu Phe Val
                20                  25                  30

Tyr Ile Ala Thr Val Gly Gly Asn Met Leu Ile Val Thr Ile Leu
            35                  40                  45

Ser Ser Pro Ala Leu Leu Val Ser Pro Met Tyr Phe Phe Leu Gly Phe
    50                  55                  60

Leu Ser Phe Leu Asp Ala Cys Phe Ser Ser Val Ile Thr Pro Lys Met
65                  70                  75                  80

Ile Val Asp Ser Leu Tyr Val Thr Lys Thr Ile Ser Phe Glu Gly Cys
                85                  90                  95

Met Val Gln Leu Phe Ala Glu His Phe Ala Gly Val Glu Val Ile
            100                 105                 110

Val Leu Thr Ala Met Ala Tyr Asp Arg Tyr Val Ala Ile Cys Lys Pro
            115                 120                 125

Leu His Tyr Ser Ser Ile Met Asn Arg Arg Leu Cys Gly Ile Leu Met
    130                 135                 140

Gly Val Ala Trp Thr Gly Gly Leu Leu His Ser Met Ile Gln Ile Leu
145                 150                 155                 160

Phe Thr Phe Gln Leu Pro Phe Cys Gly Pro Asn Val Ile Asn His Phe
                165                 170                 175

Met Cys Asp Leu Tyr Pro Leu Leu Glu Leu Ala Cys Thr Asp Thr His
            180                 185                 190

Ile Phe Gly Leu Met Val Val Ile Asn Ser Gly Phe Ile Cys Ile Ile
    195                 200                 205

Asn Phe Ser Leu Leu Leu Val Ser Tyr Ala Val Ile Leu Leu Ser Leu
    210                 215                 220

Arg Thr His Ser Ser Glu Gly Arg Trp Lys Ala Leu Ser Thr Cys Gly
225                 230                 235                 240

Ser His Ile Ala Val Val Ile Leu Phe Phe Val Pro Cys Ile Phe Val
                245                 250                 255

Tyr Thr Arg Pro Pro Ser Ala Phe Ser Leu Asp Lys Met Ala Ala Ile 260                 265                 270
Phe Tyr Ile Ile Leu Asn Pro Leu Leu Asn Pro Leu Ile Tyr Thr Phe
                275                 280                 285

Arg Asn Lys Glu Val Lys Gln Ala Met Arg Ile Trp Asn Arg Leu
            290                 295                 300

Met Val Val Ser Asp Glu Lys Glu Asn Ile Lys Leu
305                 310                 315

<210> SEQ ID NO 39
<211> LENGTH: 315
<212> TYPE: PRT
<213> ORGANISM: Homo sapiens

<400> SEQUENCE: 39

Met Arg Gln Asn Asn Asn Ile Thr Phe Phe Val Leu Leu Gly Phe Ser
  1               5                  10                  15

Gln Asp Pro Gly Val Gln Lys Ala Leu Phe Val Met Phe Leu Leu Thr
             20                  25                  30

Tyr Leu Val Thr Val Val Gly Asn Leu Leu Ile Val Val Asp Ile Ile
         35                  40                  45

Ala Ser Pro Ser Leu Gly Ser Pro Met Tyr Phe Phe Leu Ala Cys Leu
     50                  55                  60

Ser Phe Ile Asp Ala Ala Tyr Ser Thr Thr Ile Ser Pro Lys Leu Ile
 65                  70                  75                  80

Val Gly Leu Phe Cys Asp Lys Lys Thr Ile Ser Phe Gln Gly Cys Met
                 85                  90                  95

Gly Gln Leu Phe Ile Asp His Phe Phe Gly Gly Ala Glu Val Phe Leu
            100                 105                 110

Leu Val Val Met Ala Cys Asp Arg Tyr Val Ala Ile Cys Lys Pro Leu
        115                 120                 125

His Tyr Leu Thr Ile Met Asn Arg Gln Val Cys Phe Leu Leu Leu Val
    130                 135                 140

Val Ala Met Ile Gly Gly Phe Val His Ser Ala Phe Gln Ile Val Val
145                 150                 155                 160

Tyr Ser Leu Pro Phe Cys Gly Pro Asn Val Ile Val His Phe Ser Cys
                165                 170                 175

Asp Met His Pro Leu Leu Glu Leu Ala Cys Thr Asp Thr Tyr Phe Ile
            180                 185                 190

Gly Leu Thr Val Val Val Asn Ser Gly Ala Ile Cys Met Val Ile Phe
        195                 200                 205

Asn Leu Leu Leu Ile Ser Tyr Gly Val Ile Leu Ser Ser Leu Lys Thr
    210                 215                 220

Tyr Ser Gln Glu Lys Arg Gly Lys Ala Leu Ser Thr Cys Ser Ser Gly
225                 230                 235                 240

Ser Thr Val Val Val Leu Phe Phe Val Pro Cys Ile Phe Ile Tyr Val
                245                 250                 255

Arg Pro Val Ser Asn Phe Pro Thr Asp Lys Phe Met Thr Val Phe Tyr
            260                 265                 270

Thr Ile Ile Thr His Met Leu Ser Pro Leu Ile Tyr Thr Leu Arg Asn
        275                 280                 285

Ser Glu Met Arg Asn Ala Ile Glu Lys Leu Leu Gly Lys Lys Leu Thr
    290                 295                 300

Ile Phe Ile Ile Gly Gly Val Ser Val Leu Met
305                 310                 315

```
<210> SEQ ID NO 40
<211> LENGTH: 17
<212> TYPE: PRT
<213> ORGANISM: Murine sp.

<400> SEQUENCE: 40

Val Met Ala Gly Asn Met Ile Val Phe His Leu Leu Ala Thr Leu Cys
  1               5                  10                  15

Phe

<210> SEQ ID NO 41
<211> LENGTH: 17
<212> TYPE: PRT
<213> ORGANISM: Homo sapiens

<400> SEQUENCE: 41

Val Met Ala Gly Thr Ala Ile Phe Val His Leu Leu Ala Thr Leu Gly
  1               5                  10                  15

Phe

<210> SEQ ID NO 42
<211> LENGTH: 311
<212> TYPE: PRT
<213> ORGANISM: Homo sapiens

<400> SEQUENCE: 42

Met Ala Ala Glu Asn His Ser Phe Val Thr Lys Phe Ile Leu Val Gly
  1               5                  10                  15

Leu Thr Glu Lys Ser Glu Leu Gln Leu Pro Leu Phe Leu Val Phe Leu
                 20                  25                  30

Gly Ile Tyr Val Val Thr Val Leu Gly Asn Leu Gly Met Ile Thr Leu
             35                  40                  45

Ile Gly Leu Ser Ser His Leu His Thr Pro Met Tyr Cys Phe Leu Ser
         50                  55                  60

Ser Leu Ser Phe Ile Asp Phe Cys His Ser Thr Val Ile Thr Pro Lys
 65                  70                  75                  80

Met Leu Val Asn Phe Val Thr Glu Lys Asn Ile Ile Ser Tyr Pro Glu
                 85                  90                  95

Cys Met Thr Gln Leu Tyr Phe Phe Leu Val Phe Ala Ile Ala Glu Cys
            100                 105                 110

His Met Leu Ala Ala Met Ala Tyr Asp Gly Tyr Val Ala Ile Cys Ser
        115                 120                 125

Pro Leu Leu Tyr Ser Ile Ile Ile Ser Asn Lys Ala Cys Phe Ser Leu
    130                 135                 140

Ile Leu Val Val Tyr Val Gly Leu Ile Cys Ala Ser Ala His Ile
145                 150                 155                 160

Gly Cys Met Phe Arg Val Gln Phe Cys Lys Phe Asp Val Ile Asn His
                165                 170                 175

Tyr Phe Cys Asp Leu Ile Ser Ile Leu Lys Leu Ser Cys Ser Ser Thr
            180                 185                 190

Tyr Ile Asn Glu Leu Leu Ile Leu Ile Phe Ser Gly Ile Asn Ile Leu
        195                 200                 205

Val Pro Ser Leu Thr Ile Leu Ser Ser Tyr Ile Phe Ile Ile Ala Ser
    210                 215                 220

Ile Leu Arg Ile Arg Tyr Thr Glu Gly Arg Ser Lys Ala Phe Ser Thr
225                 230                 235                 240
```

-continued

```
Cys Ser Ser His Ile Ser Ala Val Ser Val Phe Phe Gly Ser Ala Ala
                245                 250                 255

Phe Met Tyr Leu Gln Pro Ser Ser Val Ser Ser Met Asp Gln Gly Lys
                260                 265                 270

Val Ser Ser Val Phe Tyr Thr Ile Val Val Pro Met Leu Asn Pro Leu
            275                 280                 285

Ile Tyr Ser Leu Arg Asn Lys Asp Val His Val Ala Leu Lys Lys Thr
290                 295                 300

Leu Gly Lys Arg Thr Phe Leu
305                 310
```

<210> SEQ ID NO 43
<211> LENGTH: 17
<212> TYPE: PRT
<213> ORGANISM: Murine sp.

<400> SEQUENCE: 43

```
Leu Leu Ile Gly Leu Met Tyr Val Leu Ile Lys Val Phe Ala Asp Leu
  1               5                  10                  15

Val
```

<210> SEQ ID NO 44
<211> LENGTH: 316
<212> TYPE: PRT
<213> ORGANISM: Homo sapiens

<400> SEQUENCE: 44

```
Met Ala Glu Glu Asn His Thr Met Lys Asn Glu Phe Ile Leu Thr Gly
  1               5                  10                  15

Phe Thr Asp His Pro Glu Leu Lys Thr Leu Leu Phe Val Val Phe Phe
                 20                  25                  30

Ala Ile Tyr Leu Ile Thr Val Val Gly Asn Ile Ser Leu Val Ala Leu
             35                  40                  45

Ile Phe Thr His Arg Arg Leu His Thr Pro Met Tyr Ile Phe Leu Gly
         50                  55                  60

Asn Leu Ala Leu Val Asp Ser Cys Cys Ala Cys Ala Ile Thr Pro Lys
 65                  70                  75                  80

Met Leu Glu Asn Phe Phe Ser Glu Asn Lys Arg Ile Ser Leu Tyr Glu
                 85                  90                  95

Cys Ala Val Gln Phe Tyr Phe Leu Cys Thr Val Glu Thr Ala Asp Cys
            100                 105                 110

Phe Leu Leu Ala Ala Met Ala Tyr Asp Arg Tyr Val Ala Ile Cys Asn
        115                 120                 125

Pro Leu Gln Tyr His Thr Met Met Ser Lys Lys Leu Cys Ile Gln Met
130                 135                 140

Thr Thr Gly Ala Phe Ile Ala Gly Asn Leu His Ser Met Ile His Val
145                 150                 155                 160

Gly Leu Val Phe Arg Leu Val Phe Cys Gly Ser Asn His Ile Asn His
                165                 170                 175

Phe Tyr Cys Asp Ile Leu Pro Leu Tyr Arg Leu Ser Cys Val Asp Pro
            180                 185                 190

Tyr Ile Asn Glu Leu Val Leu Phe Ile Phe Ser Gly Ser Val Gln Val
        195                 200                 205

Phe Thr Ile Gly Ser Val Leu Ile Ser Tyr Leu Tyr Ile Leu Leu Thr
    210                 215                 220

Ile Phe Lys Met Lys Ser Lys Glu Gly Arg Ala Lys Ala Phe Ser Thr
```

```
                225                 230                 235                 240
Cys Ala Ser His Phe Leu Ser Val Ser Leu Phe Tyr Gly Ser Leu Phe
                    245                 250                 255

Phe Met Tyr Val Arg Pro Asn Leu Leu Glu Glu Gly Asp Lys Asp Ile
            260                 265                 270

Pro Ala Ala Ile Leu Phe Thr Ile Val Val Pro Leu Leu Asn Pro Phe
        275                 280                 285

Ile Tyr Ser Leu Arg Asn Arg Glu Val Ile Ser Val Leu Arg Lys Ile
    290                 295                 300

Leu Met Lys Glu Ile Ile Ser Arg Arg Trp Lys Gln
305                 310                 315

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus amino acid motif

<400> SEQUENCE: 45

Glu Phe Ile Leu Leu
  1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus amino acid motif

<400> SEQUENCE: 46

Leu His Thr Pro Met Tyr
  1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus amino acid motif

<400> SEQUENCE: 47

Met Ala Tyr Asp Arg Tyr Val Ala Ile Cys
  1               5                  10

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus amino acid motif

<400> SEQUENCE: 48

Phe Ser Thr Cys Ser Ser His
  1               5

<210> SEQ ID NO 49
<211> LENGTH: 6
<212> TYPE: PRT
<213> ORGANISM: Artificial Sequence
<220> FEATURE:
```

<223> OTHER INFORMATION: Description of Artificial Sequence: Synthetic
      consensus amino acid motif

<400> SEQUENCE: 49

Pro Met Leu Asn Pro Phe
  1               5

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      translocation domain sequence

<400> SEQUENCE: 50

Met Asn Gly Thr Glu Gly Pro Asn Phe Tyr Val Pro Phe Ser Asn Lys
  1               5                  10                  15

Thr Gly Val Val
         20

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Glu or Asp

<400> SEQUENCE: 51

Xaa Phe Ile Leu Leu Gly
  1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Ala or Gly
<220> FEATURE:
<221> NAME/KEY: MOD_RES
<222> LOCATION: (3)
<223> OTHER INFORMATION: Tyr or Phe

<400> SEQUENCE: 52

Met Xaa Xaa Asp Arg Tyr Val Ala Ile
  1               5

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 53
atggsctwtg accghtwygt                                              20

<210> SEQ ID NO 54

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gly or Ala

<400> SEQUENCE: 54

Thr Cys Xaa Ser His Leu
 1               5

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: a, t, c. g, other or unknown
<220> FEATURE:
<221> NAME/KEY: modified_base
<222> LOCATION: (9)
<223> OTHER INFORMATION: a, t, c. g, other or unknown
<220> FEATURE:
<221> NAME/KEY: modified_base
<222> LOCATION: (15)
<223> OTHER INFORMATION: a, t, c. g, other or unknown

<400> SEQUENCE: 55
agrtgnswns crcangt                                                  17

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 56
ggggtccgga grsrtadatv avvgg                                         25

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (16)
<223> OTHER INFORMATION: a, c, g or t
<220> FEATURE:
<221> NAME/KEY: modified_base
<222> LOCATION: (25)
<223> OTHER INFORMATION: a, c, g or t

<400> SEQUENCE: 57
ggggctgcag acaccnatgt ayytnttyyt                                    30

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Primer
```

<400> SEQUENCE: 58
ggggtccgga grstradatv avvgg                                      25

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (16)
<223> OTHER INFORMATION: a, c, g or t
<220> FEATURE:
<221> NAME/KEY: modified_base
<222> LOCATION: (25)
<223> OTHER INFORMATION: a, c, g or t

<400> SEQUENCE: 59
ggggctgcag acaccnatgt ayytnttyyt                                 30

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (20)
<223> OTHER INFORMATION: a, c, g or t
<220> FEATURE:
<221> NAME/KEY: modified_base
<222> LOCATION: (22)..(23)
<223> OTHER INFORMATION: a, c, g or t

<400> SEQUENCE: 60
ggggtccgga grstradatn anngg                                      25

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (16)
<223> OTHER INFORMATION: a, c, g or t
<220> FEATURE:
<221> NAME/KEY: modified_base
<222> LOCATION: (25)
<223> OTHER INFORMATION: a, c, g or t

<400> SEQUENCE: 61
ggggctgcag acaccnatgt ayytnttyyt                                 30

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: 2'-deoxyinosine
<220> FEATURE:
<221> NAME/KEY: modified_base
<222> LOCATION: (12)

```
<223> OTHER INFORMATION: 2'-deoxyinosine
<220> FEATURE:
<221> NAME/KEY: modified_base
<222> LOCATION: (18)
<223> OTHER INFORMATION: 2'-deoxyinosine

<400> SEQUENCE: 62
atraanggrt tnarcatngg                                            20

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: 2'-deoxyinosine
<220> FEATURE:
<221> NAME/KEY: modified_base
<222> LOCATION: (15)
<223> OTHER INFORMATION: 2'-deoxycytidine phosphorothioate

<400> SEQUENCE: 63
atggcntayg aymgctaygt ngc                                        23

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (10)
<223> OTHER INFORMATION: 2'-deoxyinosine
<220> FEATURE:
<221> NAME/KEY: modified_base
<222> LOCATION: (19)
<223> OTHER INFORMATION: 2'-deoxyinosine
<220> FEATURE:
<221> NAME/KEY: modified_base
<222> LOCATION: (25)
<223> OTHER INFORMATION: 2'-deoxyinosine
<220> FEATURE:
<221> NAME/KEY: modified_base
<222> LOCATION: (28)
<223> OTHER INFORMATION: a, c, g or t

<400> SEQUENCE: 64
cggatccgcn tasgaygcnt aygtngcnat htg                             33

<210> SEQ ID NO 65
<211> LENGTH: 31
<212> TYPE: DNA
<213> ORGANISM: Artificial Sequence
<220> FEATURE:
<221> NAME/KEY: modified_base
<222> LOCATION: (17)
<223> OTHER INFORMATION: 2'-deoxyinosine
<220> FEATURE:
<221> NAME/KEY: modified_base
<222> LOCATION: (23)
<223> OTHER INFORMATION: 2'-deoxyinosine
<220> FEATURE:
<221> NAME/KEY: modified_base
<222> LOCATION: (29)
<223> OTHER INFORMATION: a, c, g or t
<220> FEATURE:
<223> OTHER INFORMATION: Description of Artificial Sequence: Primer

<400> SEQUENCE: 65
```

```
cctgcagrta datraanggr ttnarcatng g                                      31
```

```
<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (6)
<223> OTHER INFORMATION: 2'-deoxyinosine
<220> FEATURE:
<221> NAME/KEY: modified_base
<222> LOCATION: (9)
<223> OTHER INFORMATION: 2'-deoxyinosine
<220> FEATURE:
<221> NAME/KEY: modified_base
<222> LOCATION: (12)
<223> OTHER INFORMATION: 2'-deoxyinosine
<220> FEATURE:
<221> NAME/KEY: modified_base
<222> LOCATION: (15)
<223> OTHER INFORMATION: 2'-deoxyinosine
<220> FEATURE:
<221> NAME/KEY: modified_base
<222> LOCATION: (21)
<223> OTHER INFORMATION: 2'-deoxyinosine
<220> FEATURE:
<221> NAME/KEY: modified_base
<222> LOCATION: (24)
<223> OTHER INFORMATION: 2'-deoxyinosine

<400> SEQUENCE: 66
aarkcnttnb mnacntgygs ntcnca                                            26
```

```
<210> SEQ ID NO 67
<211> LENGTH: 17
<212> TYPE: PRT
<213> ORGANISM: Homo sapiens

<400> SEQUENCE: 67

Leu Leu Ile Gly Leu Ile Tyr Ile Leu Val Lys Ile Phe Ala Asp Leu
 1               5                  10                  15

Ser
```

```
<210> SEQ ID NO 68
<211> LENGTH: 17
<212> TYPE: PRT
<213> ORGANISM: Murine sp.

<400> SEQUENCE: 68

Phe Cys Glu Thr Cys Gly Ala His Ile His Phe Ile Phe Ser Val Gln
 1               5                  10                  15

Phe
```

```
<210> SEQ ID NO 69
<211> LENGTH: 17
<212> TYPE: PRT
<213> ORGANISM: Homo sapiens

<400> SEQUENCE: 69

Phe Cys Glu Thr Cys Gly Ala His Ile His Leu Leu Phe Ser Val Gln
 1               5                  10                  15

Phe
```

```
<210> SEQ ID NO 70
<211> LENGTH: 17
<212> TYPE: PRT
<213> ORGANISM: Murine sp.

<400> SEQUENCE: 70

Met Leu Gly Cys Ser Gly Ser Val Val Asp Phe Ile Met Gly Ile Leu
 1               5                  10                  15

Gly

<210> SEQ ID NO 71
<211> LENGTH: 17
<212> TYPE: PRT
<213> ORGANISM: Homo sapiens

<400> SEQUENCE: 71

Ile Leu Gly Cys Cys Arg Ser Val Val Asp Phe Ile Met Gly Ile Leu
 1               5                  10                  15

Ala

<210> SEQ ID NO 72
<211> LENGTH: 17
<212> TYPE: PRT
<213> ORGANISM: Murine sp.

<400> SEQUENCE: 72

Met Leu Ser Gly Ile Ala Ile Asn Leu His Leu Ile Thr Ala Leu Ala
 1               5                  10                  15

Gly

<210> SEQ ID NO 73
<211> LENGTH: 17
<212> TYPE: PRT
<213> ORGANISM: Homo sapiens

<400> SEQUENCE: 73

Met Leu Val Gly Asn Ala Met Asn Leu Gln Met Met Ala Val Leu Gly
 1               5                  10                  15

Gly

<210> SEQ ID NO 74
<211> LENGTH: 17
<212> TYPE: PRT
<213> ORGANISM: Murine sp.

<400> SEQUENCE: 74

Leu Leu Gly Ser Cys Ala Ser Asn Leu Gln Trp Leu Ile Ser Phe Leu
 1               5                  10                  15

Ile

<210> SEQ ID NO 75
<211> LENGTH: 17
<212> TYPE: PRT
<213> ORGANISM: Homo sapiens

<400> SEQUENCE: 75

Leu Leu Gly Ser Cys Ala Ser Asn Leu Gln Trp Leu Ile Ser Phe Leu
 1               5                  10                  15

Ile

<210> SEQ ID NO 76
```

```
<211> LENGTH: 17
<212> TYPE: PRT
<213> ORGANISM: Murine sp.

<400> SEQUENCE: 76

Phe Leu Thr Ile Cys Gly Met Gly Thr Gln Phe Ala Phe Ser Asn Ile
 1               5                  10                  15

Ile

<210> SEQ ID NO 77
<211> LENGTH: 17
<212> TYPE: PRT
<213> ORGANISM: Homo sapiens

<400> SEQUENCE: 77

Leu Leu Ala Ile Cys Val Ile Cys Ala His Cys Ile Phe Ser Asn Ile
 1               5                  10                  15

Val

<210> SEQ ID NO 78
<211> LENGTH: 17
<212> TYPE: PRT
<213> ORGANISM: Murine sp.

<400> SEQUENCE: 78

Ile Leu Gly Cys Asn Val Phe Asn Val His Leu Ile Leu Ala Val Ile
 1               5                  10                  15

Val

<210> SEQ ID NO 79
<211> LENGTH: 17
<212> TYPE: PRT
<213> ORGANISM: Homo sapiens

<400> SEQUENCE: 79

Met Ile Thr Asp Asn Val Leu Asn Ser His Leu Ile Val Gly Val Ile
 1               5                  10                  15

Leu

<210> SEQ ID NO 80
<211> LENGTH: 17
<212> TYPE: PRT
<213> ORGANISM: Murine sp.

<400> SEQUENCE: 80

Met Leu Gly Asp Ser Leu Leu His Leu His Leu Ile Ile Gly Val Val
 1               5                  10                  15

Leu

<210> SEQ ID NO 81
<211> LENGTH: 17
<212> TYPE: PRT
<213> ORGANISM: Homo sapiens

<400> SEQUENCE: 81

Met Leu Gly Asp Ser Leu Leu His Leu His Leu Ile Met Gly Ile Leu
 1               5                  10                  15

Ile

<210> SEQ ID NO 82
<211> LENGTH: 17
```

```
<212> TYPE: PRT
<213> ORGANISM: Murine sp.

<400> SEQUENCE: 82

Leu His Ala Gly Val Val Gly His Thr Gln Phe Val Asn Ser Phe Cys
 1               5                  10                  15

Ile

<210> SEQ ID NO 83
<211> LENGTH: 17
<212> TYPE: PRT
<213> ORGANISM: Homo sapiens

<400> SEQUENCE: 83

Leu His Ala Gly Val Val Gly His Ile Gln Phe Val Asn Ser Ile Cys
 1               5                  10                  15

Ile

<210> SEQ ID NO 84
<211> LENGTH: 17
<212> TYPE: PRT
<213> ORGANISM: Murine sp.

<400> SEQUENCE: 84

Leu His Gly Gly Val Ile Gly His Ile Gln Thr Val Asn Gly Ile Cys
 1               5                  10                  15

Gly

<210> SEQ ID NO 85
<211> LENGTH: 17
<212> TYPE: PRT
<213> ORGANISM: Homo sapiens

<400> SEQUENCE: 85

Leu His Gly Gly Val Val Gly His Phe Gln Val Val Asn Ser Ile Cys
 1               5                  10                  15

Val

<210> SEQ ID NO 86
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
attggatcca ggccgcttgg acaaaaatga atctttttt tttttttttt tttttt        57
```